(12) United States Patent
Jakob et al.

(10) Patent No.: US 9,688,683 B2
(45) Date of Patent: Jun. 27, 2017

(54) SUBSTITUTED CONDENSED PYRIMIDINE COMPOUNDS

(71) Applicant: GRÜNENTHAL GMBH, Aachen (DE)

(72) Inventors: Florian Jakob, Aachen (DE); Ingo Konetzki, Aachen (DE); Tobias Craan, Aachen (DE); Antonio Nardi, Herzogenrath (DE); Christian Hesslinger, Zoznegg (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 15/018,968

(22) Filed: Feb. 9, 2016

(65) Prior Publication Data

US 2016/0152624 A1 Jun. 2, 2016

Related U.S. Application Data

(63) Continuation of application No. PCT/EP2014/002192, filed on Aug. 8, 2014.

(30) Foreign Application Priority Data

Aug. 9, 2013 (EP) .................................. 13003992
Jul. 16, 2014 (EP) .................................. 14002453

(51) Int. Cl.
  *C07D 487/04* (2006.01)
(52) U.S. Cl.
  CPC ................................ *C07D 487/04* (2013.01)
(58) Field of Classification Search
  None
  See application file for complete search history.

(56) References Cited

U.S. PATENT DOCUMENTS

| 2004/0102460 A1 | 5/2004 | Hopper et al. |
| 2005/0059686 A1 | 3/2005 | Eggenweiler et al. |
| 2006/0293343 A1 | 12/2006 | Naganuma et al. |

FOREIGN PATENT DOCUMENTS

| WO | 95/01338 A1 | 1/1995 |
| WO | 03 087064 A1 | 10/2003 |

OTHER PUBLICATIONS

Azam et al., Selective Phosphodiesterase 4B inhibitors: A review. Scientia Phamaceutica, 2014, 82, 453-381.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Chemical Abstract Registry No. 1007340-68-2, indexed in the Registry File on STN CAS Online Mar. 10, 2008.*
Schudt et al., "PDE Isoenzymes as Targets for Anti-Asthma Drugs"; European Respiratory Journal, 1995, vol. 8, pp. 1179-1183.
Mori, et al., "The human area postrema and other nuclei related to the emetic reflex express cAMP phosphodiesterases 4B and 4D"; Journal of Chemical Neuroanatomy, vol. 40, 2010, pp. 36-42.
Press, et al., "2 PDE4 Inhibitors—A review of the current field"; Progress in Medicinal Chemistry, vol. 47, 2009, pp. 37-74.
Robichaud, et al., "Deletion of phosphodiesterase 4D in mice shortens alpha2-adrenoceptor-mediated anesthesia, a behavioral correlate of emesis"; Journal of Clinical Investigation, vol. 110, No. 7, 2002, pp. 1045-1052.
Lee, et al., "Dynamic Regulation of Cystic Fibrosis Transmembrane Conductance Regulator by Competitive Interactions of Molecular Adaptors"; the Journal of Biological Chemistry, vol. 282, No. 14, Apr. 6, 2007, pp. 10414-10422.
Giembycz, "4D or not 4D—the emetogenic basis of PDE4 inhibitors uncovered?"; Trends in Pharmacological Sciences, vol. 23, No. 12, Dec. 2002, pp. 548.
Naganuma, et al., "Discovery of selective PDE4B inhibitors"; Bioorganic & Medicinal Chemistry Letters 19, 2009, pp. 3174-3176.
S. Tumkevicius et al., "Synthesis and photophysical properties of oligoarylenes with a pyrrolo[2,3-d]pyrimidine core" Tetrahedron Letters 51, 2010, p. 3902-3906.
Liu et al., "Synthesis and Herbicidal Activity of 2-(3-(Trifluoromethyl)-5-(alkoxy)-1H-pyrazol-1-yl)-4-aryloxypyrimidine Derivatives"; J. of Heterocyclic Chem., 2007, 44, p. 967-971.
"Remington's Pharmaceutical Sciences", Ed. A.R. Gennaro, 17th edition, Mack Publishing Company, Easton PA (1985), chapters 76.
"Remington's Pharmaceutical Sciences", Ed. A.R. Gennaro, 17th edition, Mack Publishing Company, Easton PA (1985), chapters 77.
"Remington's Pharmaceutical Sciences", Ed. A.R. Gennaro, 17th edition, Mack Publishing Company, Easton PA (1985), chapters 78.
"Remington's Pharmaceutical Sciences", Ed. A.R. Gennaro, 17th edition, Mack Publishing Company, Easton PA (1985), chapters 79.
"Remington's Pharmaceutical Sciences", Ed. A.R. Gennaro, 17th edition, Mack Publishing Company, Easton PA (1985), chapters 80.
"Remington's Pharmaceutical Sciences", Ed. A.R. Gennaro, 17th edition, Mack Publishing Company, Easton PA (1985), chapters 81.
"Remington's Pharmaceutical Sciences", Ed. A.R. Gennaro, 17th edition, Mack Publishing Company, Easton PA (1985), chapters 82.
"Remington's Pharmaceutical Sciences", Ed. A.R. Gennaro, 17th edition, Mack Publishing Company, Easton PA (1985), chapters 83.
"Remington's Pharmaceutical Sciences", Ed. A.R. Gennaro, 17th edition, Mack Publishing Company, Easton PA (1985), chapters 84.

(Continued)

*Primary Examiner* — Matthew Coughlin
*Assistant Examiner* — Po-Chih Chen
(74) *Attorney, Agent, or Firm* — Norris McLaughlin & Marcus, P.A.

(57) ABSTRACT

Novel substituted condensed pyrimidine compounds of general formula (I)

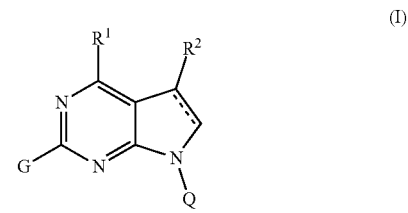

in which the chemical groupings, substituents and indices are as defined in the description, and to their use as medicaments, in particular as medicaments for the treatment of conditions and diseases that can be treated by inhibition of the PDE4 enzyme.

10 Claims, No Drawings

(56) References Cited

OTHER PUBLICATIONS

"Remington's Pharmaceutical Sciences", Ed. A.R. Gennaro, 17th edition, Mack Publishing Company, Easton PA (1985), chapters 85.
"Remington's Pharmaceutical Sciences", Ed. A.R. Gennaro, 17th edition, Mack Publishing Company, Easton PA (1985), chapters 86.
"Remington's Pharmaceutical Sciences", Ed. A.R. Gennaro, 17th edition, Mack Publishing Company, Easton PA (1985), chapters 87.
"Remington's Pharmaceutical Sciences", Ed. A.R. Gennaro, 17th edition, Mack Publishing Company, Easton PA (1985), chapters 88.
"Remington's Pharmaceutical Sciences", Ed. A.R. Gennaro, 17th edition, Mack Publishing Company, Easton PA (1985), chapters 89.
"Remington's Pharmaceutical Sciences", Ed. A.R. Gennaro, 17th edition, Mack Publishing Company, Easton PA (1985), chapters 90.
"Remington's Pharmaceutical Sciences", Ed. A.R. Gennaro, 17th edition, Mack Publishing Company, Easton PA (1985), chapters 91.
"Remington's Pharmaceutical Sciences", Ed. A.R. Gennaro, 17th edition, Mack Publishing Company, Easton PA (1985), chapters 92.
"Remington's Pharmaceutical Sciences", Ed. A.R. Gennaro, 17th edition, Mack Publishing Company, Easton PA (1985), chapters 93.
Miyaura et al., "Palladium-Catalyzed Cross-Coupling Reactions of Organoboron Compounds"; Chem. Rev., 1995, 95, p. 2457-2483.
Green et al.; "Protective Groups in Organic Synthesis"; A Wiley-Interscience Publication, New York, 1999, p. 518-525.
Provins, et al.; "First dual M3 antagonists-PDE4 inhibitors: Synthesis and SAR of 4,6-diaminopyrimidine derivatives"; Bioorganic & Medicinal Chemistry Letters 16 (2006) 1834-1839.
Jana et al.; "Advances in Transition Metal (Pd, Ni, Fe)-Catalyzed Cross-Coupling Reactions Using Alkyl-organometallics as Reaction Partners"; Chem. Rev., 2011, 111, p. 1417-1492.
Qiao, et al., "Copper-Promoted Carbon—Heteroatom Bond Cross-Coupling with Boronic Acids and Derivatives"; Synthesis 2011, No. 6, pp. 0829-0856.
Surry et al., "Dialkylbiaryl phosphines in Pd-catalyzed amination: a user's guide"; Chem. Sci., 2011, 2, p. 27-50.
Podesva et al., "Structures of Cyclohexaptone-Urea Condensation Products"; Canadian Journal of Chemistry. vol. 40 (1962).
Fissekisa, et al.; "Synthesis of 5-Hydroxyalkylpyrimidines from Lactones"; JOC, 1964, 29, p. 1670-2673.
Greene, et al., "Protection for the Amino Group"; Protective Groups in Organic Synthesis, Third Edition, 1999, p. 494-653.
Beletskaya et al., "Copper in cross-coupling reactions the post-Ullmann chemistry"; Coordination Chemistry Reviews 248 (2004) 2337-2364.
Hudlický; "Oxidations in Organic Chemistry"; American Chemical Society, Washington, DC 1990, Table of Contents.
Arotsky et al.; "Iodination and Iodo-compounds. Part IV.I The Effect of Substituents and Solvent Composition on the Rate of Aromatic Iodination by Means of the Tri-iodine Cation"; J. Chem. Soc., Perkin Trans. 2, 1973, p. 595-599.
Greene et al., "Protective Groups in Organic Synthesis", Third Edition, John Wiley & Sons, Inc., 1999, p. 154-155.
Klumpp, et al.; "Pyrrolo[2,3-d]Pyrimidines as Inhibitors of cAMP-Phosphodiesterase"; Biochemical Pharmacology, 1989, vol. 38, No. 6, pp. 949-953.
Kawada et al.; "Lead optimization of a dihydropyrrolopyrimidine inhibitor against phosphoinositide 3-kinase (PI3K) to improve the phenol glucuronic acid conjugation"; Bioorganic & Medicinal Chemistry Letters 23 (2013), pp. 673-678.
Martin; "PDEA inhibitors—A review of the recent patent literature"; IDrugs 2001, 4 (3), pp. 312-338.

* cited by examiner

SUBSTITUTED CONDENSED PYRIMIDINE COMPOUNDS

This application is a continuation of International Patent Application No. PCT/EP2014/002192, filed Aug. 8, 2014, which claims priority of European Patent Application Nos. 14002453.0, filed Jul. 16, 2014, and Ser. No. 13/003,992.8, filed Aug. 9, 2013, the disclosures of which patent applications are incorporated herein by reference.

The present invention relates to novel substituted condensed pyrimidine compounds, and to their use as pharmaceuticals (medicaments).

It is known that certain pyrimidine compounds are suitable for inhibiting specific phosphodiesterases (abbreviated as PDEs). Phosphodiesterases, or more accurately 3',5'-cyclonucleotide phosphodiesterases, are enzymes that catalyse the hydrolysis of the second messengers cAMP (cyclic adenosine monophosphate)- and cGMP (cyclic guanosine monophosphate) to 5'-AMP (5'-adenosine monophosphate)- and 5'-GMP (5'-guanosine monophosphate). Inhibition of phosphodiesterases thus represents a mechanism for modulating cellular processes and can be used to alleviate or cure disease conditions.

WO 95/01338 A1, for example, describes how suitable PDE inhibitors can be used to treat inflammatory respiratory diseases, dermatoses, and other proliferative, inflammatory and allergic skin diseases. WO 95/01338 A1 proposes, moreover, that such PDE inhibitors can find application in the treatment of diseases that are based on an excess release of TNF and leukotrienes, for example diseases from the arthritis spectrum (rheumatoid arthritis, rheumatoid spondylitis, osteoarthritis and other arthritic conditions). The international publication proposes, furthermore, the use of suitable PDE inhibitors as medicaments for diseases of the immune system (e.g. AIDS), symptoms of shock, as well as generalised inflammations in the gastrointestinal system (e.g. Crohn's disease and ulcerative colitis), diseases based on allergic and/or chronic, immunological adverse reactions in the upper respiratory tract (lateral pharyngeal space, nose)- and adjacent regions (sinuses, eyes), such as for example allergic rhinitis/sinusitis, chronic rhinitis/sinusitis, allergic conjunctivitis and nasal polyps, but also diseases of the heart that can be treated by PDE inhibitors, such as for example heart failure, or diseases that can be treated because of the tissue-relaxing effect of PDE inhibitors, such as for example renal and ureteric colic in conjunction with kidney stones.

Phosphodiesterases are a group of enzymes encompassing 11 gene families (PDE1-11), which differ inter alia through their affinity to cAMP and cGMP.

The inhibition of the individual gene families with suitable substances is the subject of wide-ranging research. A known PDE5 inhibitor is sildenafil, which is commercially available under the trade name Viagra™—and which is used primarily for the treatment of erectile dysfunction.

The discovery that the second messenger cAMP plays an important role in many inflammatory processes and that PDE4 is strongly expressed in cells that control inflammation processes (see inter alia Schudt, C. et al. (1995). PDE isoenzymes as targets for anti-asthma drugs. *European Respiratory Journal* 8, 1179-1183), has led to the development of PDE4 inhibitors having an anti-inflammatory effect. One such PDE4 inhibitor having an anti-inflammatory effect is roflumilast for example (known under the trade name Daxas®), which was approved as a medicament for the treatment of COPD (chronic obstructive pulmonary disease). In addition to the desired anti-inflammatory effect of roflumilast, however, side-effects such as for example nausea, diarrhoea and headaches are observed, which limit the dose in humans.

Undesired side-effects in humans were observed with other PDE4 inhibitors too, so the therapeutic range (therapeutic window) of such medicaments is relatively narrow. The provision of PDE4 inhibitors having side-effects and a better therapeutic window would therefore be desirable.

Phosphodiesterase 4 (PDE4) is cAMP-specific and encompasses 4 different subtypes (PDE4A, PDE4B, PDE4C and PDE4D). As is described below, efforts are being made to find subtype-selective PDE4 inhibitors, above all PDE4B-selective inhibitors, that have less severe or no side-effects, such that the therapeutic range of these compounds is increased significantly.

The inhibition of PDE4D is associated with the occurrence of undesired side-effects, such as for example diarrhoea, vomiting and nausea (see in this regard Mori, F. et al. (2010). The human area postrema and other nuclei related to the emetic reflex express cAMP phosphodiesterases 4B and 4D. *Journal of Chemical Neuroanatomy* 40, 36-42; Press, N.J.; Banner K. H (2009). PDE4 inhibitors—A review of the current field. *Progress in Medicinal Chemistry* 47, 37-74; Robichaud, A. et al. (2002). Deletion of phosphodiesterase 4D in mice shortens α2-adrenoceptor-mediated anesthesia, a behavioral correlate of emesis. *The Journal of Clinical Investigation* 110, 1045-52; or Lee et al., (2007). Dynamic regulation of CFTR by competitive interactions of molecular adaptors. *Journal of Biological Chemistry* 282, 10414-10422); or Giembycz, M. A. (2002). 4D or not 4D—the emetogenic basis of PDE4 inhibitors uncovered? *Trends in Pharmacological Sciences* 23, 548).

In an article entitled "Discovery of selective PDE4B inhibitors" published in Bioorganic & Medicinal Chemistry Letters 19 (2009) p. 3174-3176, Kenji et al. disclose thirty-five pyrimidine compounds that exhibit PDE4B selectivity. Some of the compounds listed are said to show a 10-times higher inhibitory activity against PDE4B than against PDE4D.

The compounds examined by Kenji et al. are substantially encompassed by the general formula described in US 2006/0293343A1. US 2006/0293343A1 discloses specific pharmaceutically effective PDE4-inhibiting pyrimidine compounds having an anti-inflammatory effect.

WO 03/087064 discloses certain substituted pyrimidine compounds having an affinity for the human m3 muscarinic receptor at concentrations ranging from 100 nM to almost 1 nM and incorporate activity as selective PDE4 inhibitors at concentrations ranging from 2.5 µM to almost 50 nM.

Based on this prior art the object was now to find compounds that are preferably PDE4B-selective (i.e. to find active compounds that with a particular amount of active ingredient inhibit PDE4B but without inhibiting or only weakly inhibiting the PDE4D subtype). The advantage of such a PDE4B selectivity, as mentioned above, is that various side-effects do not (should not) occur or occur only to a small extent and that therefore a greater therapeutic range (=therapeutic window) of the pharmaceutical active ingredient is (should be) obtained. The therapeutic range of a pharmaceutical active ingredient or medicament describes the gap between its therapeutic dose and a dose that would lead to a toxic or undesired effect. The greater the therapeutic range, the rarer or more unlikely the occurrence of certain toxic or undesired side-effects and hence the safer and more tolerable the pharmaceutical active ingredient or medicament. The therapeutic range is often also referred to as the therapeutic window or therapeutic index. These names are used synonymously in the present application.

The inventors have now found pyrimidine compounds that display the desired inhibiting and PDE4B-selective property and are superior to the corresponding pyrimidine compounds of the prior art. They are therefore particularly suitable for the treatment of diseases and conditions in which inhibition of the PDE4 enzyme, in particular the PDE4B enzyme, is advantageous.

Therefore, in a first aspect, the invention relates to condensed pyrimidine compounds of the following general formula (I)

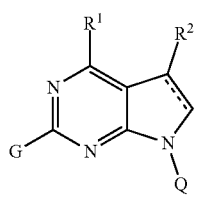

(I)

in which

G is a phenyl optionally substituted with at least one substituent Z or a 5- to 10-membered heteroaryl optionally substituted with at least one substituent Z; G preferably is phenyl, thienyl, furanyl, thiazolyl, isothiazolyl, oxazolyl, isoxazolyl, pyridiyl, pyrimidinyl, benzofuranyl, benzodioxazolyl, benzothiazolyl, quinolinyl, benzodioxazolyl; more preferably G is selected from the following groups G1 to G39

G1

G2
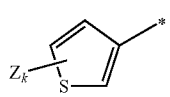

G3
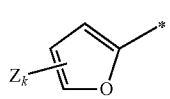

G4
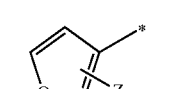

G5
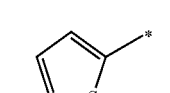

G6
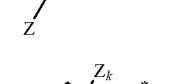

G7
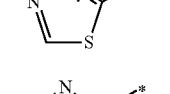

G8
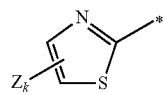

G9
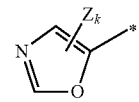

G10
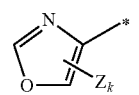

G11
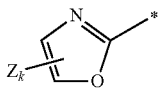

G12
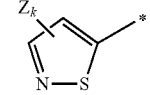

G13
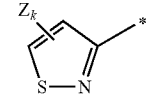

G14
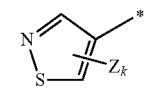

G15
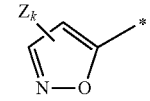

G16
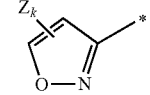

G17
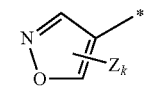

G18
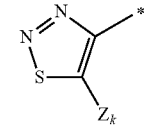

G19
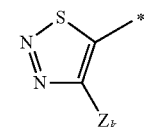

G20
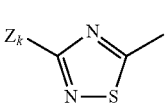

G21
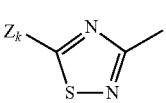

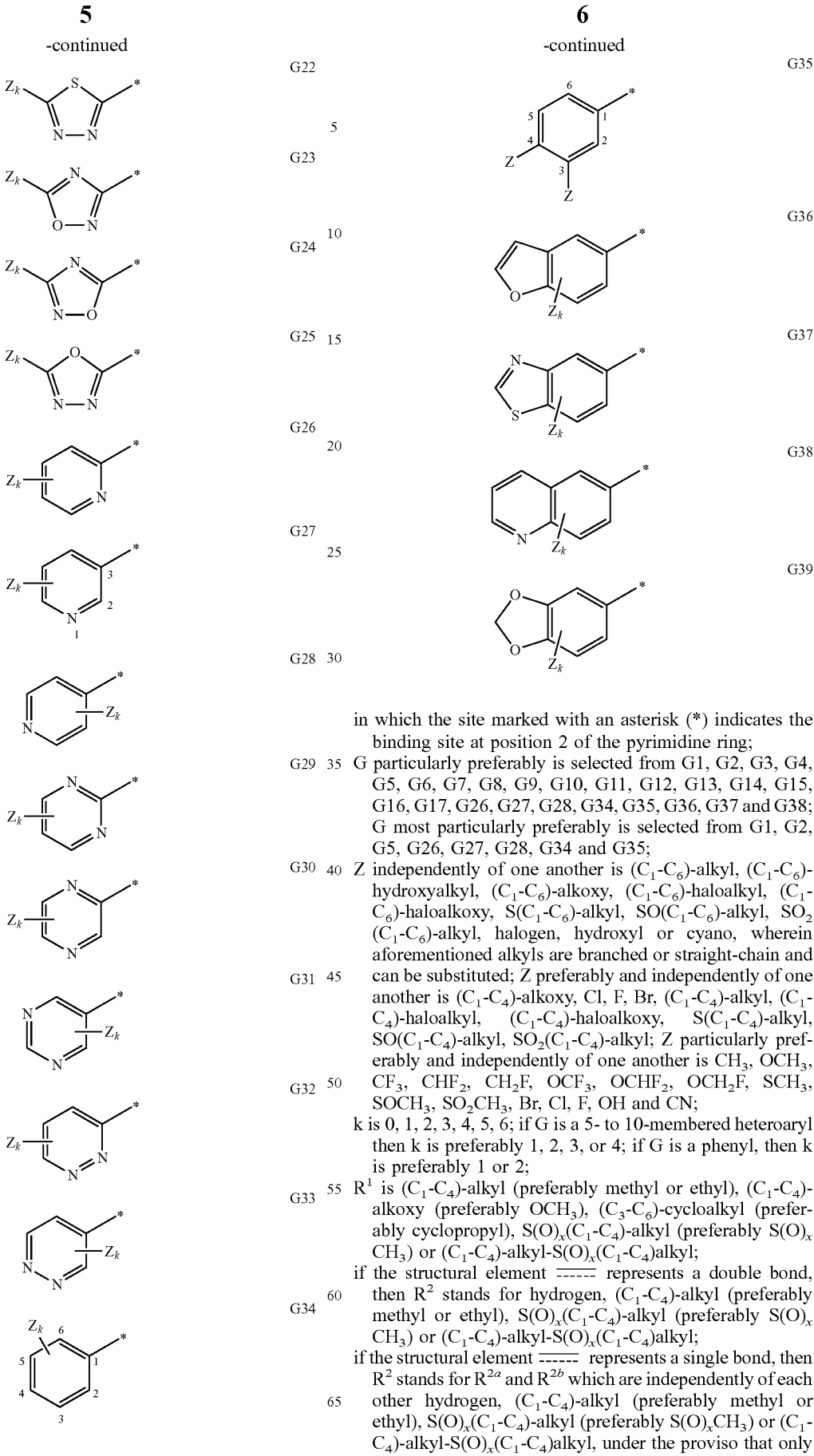

in which the site marked with an asterisk (*) indicates the binding site at position 2 of the pyrimidine ring;

G particularly preferably is selected from G1, G2, G3, G4, G5, G6, G7, G8, G9, G10, G11, G12, G13, G14, G15, G16, G17, G26, G27, G28, G34, G35, G36, G37 and G38; G most particularly preferably is selected from G1, G2, G5, G26, G27, G28, G34 and G35;

Z independently of one another is $(C_1-C_6)$-alkyl, $(C_1-C_6)$-hydroxyalkyl, $(C_1-C_6)$-alkoxy, $(C_1-C_6)$-haloalkyl, $(C_1-C_6)$-haloalkoxy, $S(C_1-C_6)$-alkyl, $SO(C_1-C_6)$-alkyl, $SO_2(C_1-C_6)$-alkyl, halogen, hydroxyl or cyano, wherein aforementioned alkyls are branched or straight-chain and can be substituted; Z preferably and independently of one another is $(C_1-C_4)$-alkoxy, Cl, F, Br, $(C_1-C_4)$-alkyl, $(C_1-C_4)$-haloalkyl, $(C_1-C_4)$-haloalkoxy, $S(C_1-C_4)$-alkyl, $SO(C_1-C_4)$-alkyl, $SO_2(C_1-C_4)$-alkyl; Z particularly preferably and independently of one another is $CH_3$, $OCH_3$, $CF_3$, $CHF_2$, $CH_2F$, $OCF_3$, $OCHF_2$, $OCH_2F$, $SCH_3$, $SOCH_3$, $SO_2CH_3$, Br, Cl, F, OH and CN;

k is 0, 1, 2, 3, 4, 5, 6; if G is a 5- to 10-membered heteroaryl then k is preferably 1, 2, 3, or 4; if G is a phenyl, then k is preferably 1 or 2;

$R^1$ is $(C_1-C_4)$-alkyl (preferably methyl or ethyl), $(C_1-C_4)$-alkoxy (preferably $OCH_3$), $(C_3-C_6)$-cycloalkyl (preferably cyclopropyl), $S(O)_x(C_1-C_4)$-alkyl (preferably $S(O)_x CH_3$) or $(C_1-C_4)$-alkyl-$S(O)_x(C_1-C_4)$alkyl;

if the structural element ----- represents a double bond, then $R^2$ stands for hydrogen, $(C_1-C_4)$-alkyl (preferably methyl or ethyl), $S(O)_x(C_1-C_4)$-alkyl (preferably $S(O)_x CH_3$) or $(C_1-C_4)$-alkyl-$S(O)_x(C_1-C_4)$alkyl;

if the structural element ----- represents a single bond, then $R^2$ stands for $R^{2a}$ and $R^{2b}$ which are independently of each other hydrogen, $(C_1-C_4)$-alkyl (preferably methyl or ethyl), $S(O)_x(C_1-C_4)$-alkyl (preferably $S(O)_x CH_3$) or $(C_1-C_4)$-alkyl-$S(O)_x(C_1-C_4)$alkyl, under the proviso that only one of $R^{2a}$ and $R^{2b}$ is $S(O)_x(C_1-C_4)$-alkyl or $(C_1-C_4)$-alkyl-$S(O)_x(C_1-C_4)$alkyl at the same time, or wherein $R^{2a}$ and $R^{2b}$ together with the carbon atom to which they are bound form a 3- to 6-membered saturated or unsaturated carbocycle (preferably a 3- or 4-membered ring) or a 3- to 6-membered heterocycle (preferably a 3- or 4-membered ring) containing at least one heteroatom selected from O, N and S wherein the sulphur atom may be oxidized to form a chemical grouping SO or $SO_2$;

x is 0, 1, or 2;

Q is pyrimidyl, pyrazinyl, pyridyl which groups are optionally substituted with at least one substituent $X^1$ and/or optionally with at least one substituent X, or is phenyl substituted with a substituent $X^1$ and optionally with at least one substituent X;

$X^1$ is selected from the following chemical groupings $L-CO_2R^3$, $O-L-CO_2R^3$, $O-L-COR^4$, $NH-L-CO_2R^3$, and $N((C_1-C_4)$-alkyl$)-L-CO_2R^3$; $X^1$ preferably stands for $CO_2R^3$, $CH_2-CO_2R^3$, $(CH_2)_2-CO_2R^3$, $CH=CH-CO_2R^3$, $CHCH_3-CO_2R^3$, $C(CH_2CH_3)_2-CO_2R^3$, $C(CH_3)_2-CO_2R^3$, $CHF-CO_2R^3$, $CF_2-CO_2R^3$, $O-CH_2-CO_2R^3$, $O-CH_2-COR^4$, $NH-CH_2-CO_2R^3$, $N(CH_3)-CH_2-CO_2R^3$, $O-CON(CH_3)_2$, or $O-CH_2-CON(CH_3)_2$; $X^1$ particularly preferably stands for $CO_2H$, $CH_2-CO_2H$, $(CH_2)_2-CO_2H$, $CH=CH-CO_2H$, $CHCH_3-CO_2H$, $C(CH_2CH_3)_2-CO_2H$, $C(CH_3)_2-CO_2H$, $CHF-CO_2H$, $CF_2-CO_2H$, $O-CH_2-CO_2H$, $O-CH_2-CONMe_2$, $NH-CH_2-CO_2H$, $N(CH_3)-CH_2-CO_2H$, or $O-CH_2-CON(CH_3)_2$;

Q preferably is selected from the following groups Q1 to Q15, in which the site marked with an asterisk indicates the binding site at the nitrogen atom; particularly preferably Q stands for Q2, Q3, Q8, Q9, or Q14; most particularly preferably Q stands for Q2, Q3 or Q14;

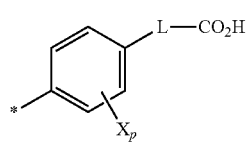
Q1

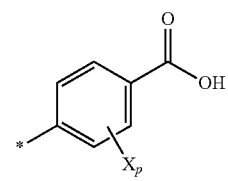
Q2

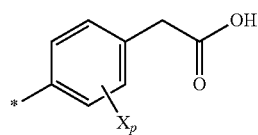
Q3

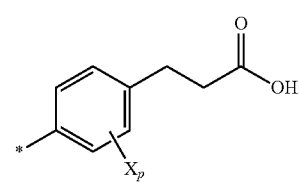
Q4

-continued

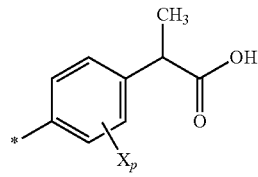
Q5

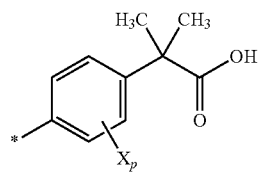
Q6

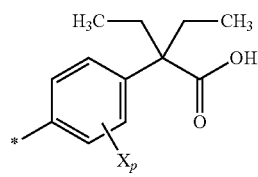
Q7

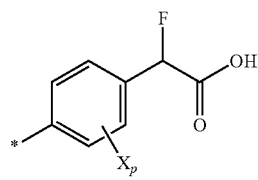
Q8

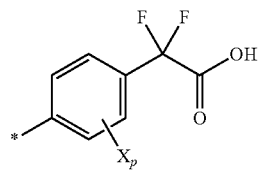
Q9

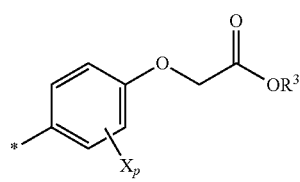
Q10

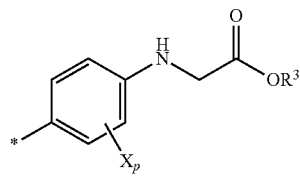
Q11

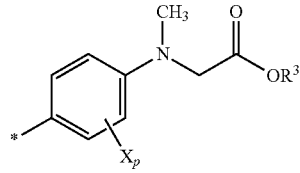
Q12

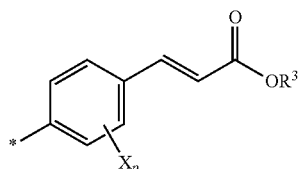 Q13

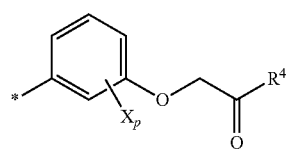 Q14

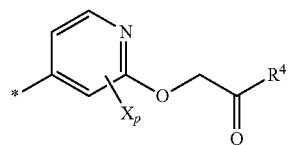 Q15

R³ is hydrogen or (C₁-C₆)-alkyl (preferably methyl or ethyl); preferably R³ is hydrogen or methyl;

R⁴ is NH₂, NHR⁵, NR⁵R⁶, whereas

R⁵ and R⁶ independently of one another is (C₁-C₆)-alkyl, (C₁-C₆)-hydroxyalkyl (preferably hydroxymethyl, hydroxyethyl, or hydroxypropyl), (C₃-C₆)-cycloalkyl (preferably cyclopropyl or cyclobutyl), (C₁-C₄)-alkyl-(C₃-C₆)-cycloalkyl (preferably CH₂-cyclopropyl), 3- to 6-membered heterocycle having at least one heteroatom selected from nitrogen, oxygen or sulphur (preferred heterocycles are oxetanyl, tetrahydrofuranyl, piperazinyl), or R⁵ and R⁶, together with the nitrogen atom to which they are bound, form a saturated 3- to 6-membered heterocycle, which optionally contains at least one further heteroatom selected from nitrogen, oxygen or sulphur, and which heterocycle can be substituted with at least one substituent selected from branched or straight-chain (C₁-C₆)-alkyl or hydroxyl; preferably R⁵ and R⁶, together with the nitrogen atom to which they are bound, form azetidinyl, piperazinyl, morpholinyl;

R⁴ is preferably NH₂, NHCH₃, N(CH₃)₂, NHC₂H₅, NHCH (CH₃)₂, NHCH₂CH₂OH or one of the following groups R⁴-1 to R⁴-9

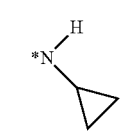 R⁴-1

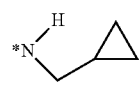 R⁴-2

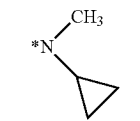 R⁴-3

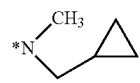 R⁴-4

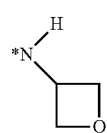 R⁴-5

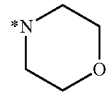 R⁴-6

 R⁴-7

 R⁴-8

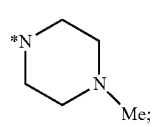 R⁴-9

L is a bond, a branched or straight-chain (C₁-C₄)-alkylene or (C₂-C₄)-alkenylene group, which alkylene or alkenylene groups may be substituted with at least one substituent selected from (C₁-C₆)-alkyl, (C₃-C₆)-cycloalkyl, (C₁-C₆)-alkoxy, (C₃-C₆)-cycloalkoxy, (C₁-C₆)-haloalkyl, (C₁-C₆)-haloalkoxy, halogen, hydroxyl, amino or cyano; preferably L is a bond, or —CH₂—, —CHCH₃—, —CHF—, —CF₂—, —C(CH₃)₂—, C(CH₂CH₃)₂, —CH═CH—, or —CH₂—CH₂—; particularly preferably L is a bond or —CH₂— (methylene);

X independently of one another is (C₁-C₆)-alkyl, (C₃-C₆)-cycloalkyl, (C₁-C₆)-alkoxy, (C₃-C₆)-cycloalkoxy, (C₁-C₆)-haloalkyl, (C₁-C₆)-haloalkoxy, halogen, hydroxyl, cyano, carboxyl, —NH₂, —NH(C₁-C₆)-alkyl, —N((C₁-C₆)-alkyl)₂, N-pyrrolidinyl, N-piperidinyl, N-morpholinyl, —NH—C(O)—(C₁-C₆)-alkyl, —C(O)—NH₂, —C(O)—NH(C₁-C₆)-alkyl, —C(O)—N((C₁-C₆)-alkyl)₂, —S(O)₂—NH₂, —S(C₁-C₆)-alkyl, —S(O)—(C₁-C₆)-alkyl, or —S(O)₂—(C₁-C₆)-alkyl, wherein the aforementioned alkyl chains are branched or straight-chain and can be substituted; and p is 0, 1, 2, 3 or 4; preferably p is 0 or 1;

as well as pharmacologically tolerable salts, diastereomers, enantiomers, racemates, hydrates or solvates thereof.

Preferred compounds according to the invention have the following general formula (I-A), (I-B), (I-B-1), (I-B-2) or (I-B-3)

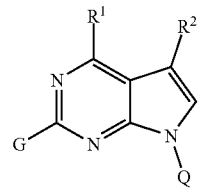 (I-A)

(I-B)

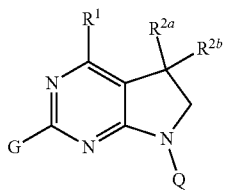

(I-B-1)

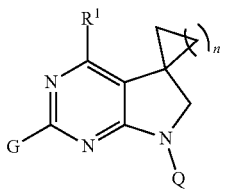

(I-B-2)

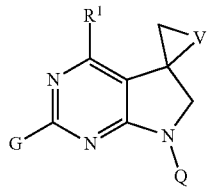

(I-B-3)

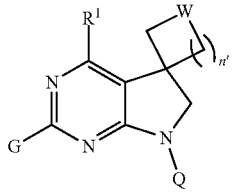

wherein n stands for 1, 2, 3, or 4; preferably n stands for 1 or 2; most preferably n stands for 1;

n' stands for 1, 2, or 3; preferably n stands for 1 or 2;

V stands for N or S(O)x';

W stands for O, N, or S(O)x'; when W stands for O, n' preferably is 1 x' is 0, 1, or 2; and all other substituents, chemical groupings and indices are as defined in the context of compounds of formula (I).

If the structural element ═══ represents a double bond and Q stands for a substituted phenyl having as substituent $X^1CO_2H$, then $R^2$ is preferably H (hydrogen) and all other substituents and chemical groupings are as defined for the compounds of general formula (I).

Further preferred compounds according to the invention have the following general formula (I-C) or (I-D) wherein all substituents, chemical groupings and indices are as defined in the context of the compounds of formula (I)

(I-C)

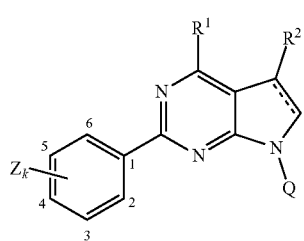

(I-D)

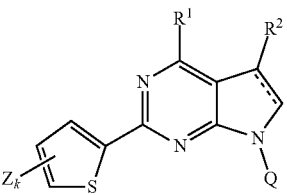

In an [embodiment A] the invention is directed to compounds having the general formula (I-C), wherein k stands for 2, and at least one Z is a halogen atom (preferably F or Cl), which is preferably bound on the 3-position at the phenyl ring and the other Z is a halogen (preferably F or Cl) or a $(C_1-C_6)$-alkoxy group (preferably methoxy), which is preferably bound on the 4-position at the phenyl ring, and wherein $R^1$ is an $(C_1-C_6)$-alkyl group (preferably methyl, ethyl, propyl or cyclopropyl) or a $S(O)_x(C_1-C_4)$-alkyl group (preferably $SCH_3$, $SOCH_3$, and $SO_2CH_3$) or a $(C_1-C_4)$-alkyl-$S(O)_x(C_1-C_4)$-alkyl group (preferably $CH_2-SCH_3$, $CH_2-SOCH_3$, and $CH_2-SO_2CH_3$), and $R^2$ or $R^{2a}$ and $R^{2b}$ each are hydrogen, and wherein Q is a phenyl group substituted with the substituent $X^1$ and optionally with at least one substituent X.

In an [embodiment B] the invention is directed to compounds having the general formula (I-D), wherein k stands for 1, and Z is a halogen atom (preferably F or Cl), which is preferably bound on the 5-position at the thienyl ring, and wherein $R^1$ is an $(C_1-C_6)$-alkyl group (preferably methyl, ethyl, propyl or cyclopropyl) or a $S(O)_x(C_1-C_4)$-alkyl group (preferably $SCH_3$, $SOCH_3$, and $SO_2CH_3$) or a $(C_1-C_4)$-alkyl-$S(O)_x(C_1-C_4)$-alkyl group (preferably $CH_2-SCH_3$, $CH_2-SOCH_3$, and $CH_2-SO_2CH_3$), and $R^2$ or $R^{2a}$ and $R^{2b}$ each are hydrogen, and wherein Q is a phenyl group substituted with a substituent $X^1$ and optionally with at least one substituent X.

In an [embodiment C] the invention is directed to compounds according to general formula (I-A), wherein G stands for a substituted phenyl ring G34 wherein k stands for 2, and at least one Z is a halogen atom (preferably F or Cl), which is preferably bound on the 3-position at the phenyl ring and the other Z is a halogen (preferably F or Cl) or a $(C_1-C_6)$-alkoxy group (preferably methoxy), which is preferably bound on the 4-position at the phenyl ring, and wherein $R^1$ is an $(C_1-C_6)$-alkyl group (preferably methyl, ethyl, propyl or cyclopropyl) or a $S(O)_x(C_1-C_4)$-alkyl group (preferably $SCH_3$, $SOCH_3$, and $SO_2CH_3$) or a $(C_1-C_4)$-alkyl-$S(O)_x(C_1-C_4)$-alkyl group (preferably $CH_2-SCH_3$, $CH_2-SOCH_3$, and $CH_2-SO_2CH_3$), and $R^2$ stands for hydrogen, $(C_1-C_4)$-alkyl (preferably methyl and ethyl), $S(O)_x(C_1-C_4)$-alkyl (preferably $SCH_3$, $SOCH_3$, and $SO_2CH_3$) or a $(C_1-C_4)$-alkyl-$S(O)_x(C_1-C_4)$-alkyl group (preferably $CH_2-SCH_3$, $CH_2-SOCH_3$, and $CH_2-SO_2CH_3$), and wherein Q is a phenyl group substituted with a substituent $X^1$ and optionally with at least one substituent X.

In an [embodiment D] the invention is directed to compounds according to general formula (I-A), wherein G stands for the thienyl group G1 wherein k stands for 1, and Z is a halogen atom (preferably F or Cl), which is preferably bound on the 5-position at the thienyl ring, and wherein $R^1$ is an $(C_1-C_6)$-alkyl group (preferably methyl, ethyl, propyl or cyclopropyl) or a $S(O)_x(C_1-C_4)$-alkyl group (preferably $SCH_3$, $SOCH_3$, and $SO_2CH_3$) or a $(C_1-C_4)$-alkyl-$S(O)_x(C_1-C_4)$-alkyl group (preferably $CH_2-SCH_3$, $CH_2-SOCH_3$, and $CH_2-SO_2CH_3$), and $R^2$ stands for hydrogen, $(C_1-C_4)$- alkyl (preferably methyl and ethyl), $S(O)_x(C_1\text{-}C_4)$-alkyl (preferably $SCH_3$, $SOCH_3$, and $SO_2CH_3$) or a $(C_1\text{-}C_4)$-alkyl-$S(O)_x(C_1\text{-}C_4)$-alkyl group (preferably $CH_2\text{—}SCH_3$, $CH_2\text{—}SOCH_3$, and $CH_2\text{—}SO_2CH_3$), and wherein Q is a phenyl group substituted with a substituent $X^1$ and optionally with at least one substituent X.

In an [embodiment E] the invention is directed to compounds according to general formula (I-B), wherein G stands for a substituted phenyl ring G34 wherein k stands for 2, and at least one Z is a halogen atom (preferably F or Cl), which is preferably bound on the 3-position at the phenyl ring and the other Z is a halogen (preferably F or Cl) or a $(C_1\text{-}C_6)$-alkoxy group (preferably methoxy), which is preferably bound on the 4-position at the phenyl ring, and wherein $R^1$ is an $(C_1\text{-}C_6)$-alkyl group (preferably methyl, ethyl, propyl or cyclopropyl) or a $S(O)_x(C_1\text{-}C_4)$-alkyl group (preferably $SCH_3$, $SOCH_3$, and $SO_2CH_3$) or a $(C_1\text{-}C_4)$-alkyl-$S(O)_x(C_1\text{-}C_4)$-alkyl group (preferably $CH_2\text{—}SCH_3$, $CH_2\text{—}SOCH_3$, and $CH_2\text{—}SO_2CH_3$), and $R^2$ stands for $R^{2a}$ and $R^{2b}$ which are independently of each other hydrogen, $(C_1\text{-}C_4)$-alkyl (preferably methyl or ethyl), $S(O)_x(C_1\text{-}C_4)$-alkyl (preferably $SCH_3$, $SOCH_3$, and $SO_2CH_3$ or a $(C_1\text{-}C_4)$-alkyl-$S(O)_x(C_1\text{-}C_4)$-alkyl group (preferably $CH_2\text{—}SCH_3$, $CH_2\text{—}SOCH_3$, and $CH_2\text{—}SO_2CH_3$), under the proviso that only one of $R^{2a}$ and $R^{2b}$ is $S(O)_x(C_1\text{-}C_4)$-alkyl or $(C_1\text{-}C_4)$-alkyl-$S(O)_x(C_1\text{-}C_4)$alkyl at the same time, and wherein Q is a phenyl group substituted with a substituent $X^1$ and optionally with at least one substituent X.

In an [embodiment F] the invention is directed to compounds according to general formula (I-B), wherein G stands for the thienyl group G1 wherein k stands for 1, and Z is a halogen atom (preferably F or Cl), which is preferably bound on the 5-position at the thienyl ring, and wherein $R^1$ is an $(C_1\text{-}C_6)$-alkyl group (preferably methyl, ethyl, propyl or cyclopropyl) or a $S(O)_x(C_1\text{-}C_4)$-alkyl group (preferably $SCH_3$, $SOCH_3$, and $SO_2CH_3$) or a $(C_1\text{-}C_4)$-alkyl-$S(O)_x(C_1\text{-}C_4)$-alkyl group (preferably $CH_2\text{—}SCH_3$, $CH_2\text{—}SOCH_3$, and $CH_2\text{—}SO_2CH_3$), and $R^2$ stands for $R^{2a}$ and $R^{2b}$ which are independently of each other hydrogen, $(C_1\text{-}C_4)$-alkyl (preferably methyl or ethyl), $S(O)_x(C_1\text{-}C_4)$-alkyl (preferably $SCH_3$, $SOCH_3$, and $SO_2CH_3$ or a $(C_1\text{-}C_4)$-alkyl-$S(O)_x(C_1\text{-}C_4)$-alkyl group (preferably $CH_2\text{—}SCH_3$, $CH_2\text{—}SOCH_3$, and $CH_2\text{—}SO_2CH_3$), under the proviso that only one of $R^{2a}$ and $R^{2b}$ is $S(O)_x(C_1\text{-}C_4)$-alkyl or $(C_1\text{-}C_4)$-alkyl-$S(O)_x(C_1\text{-}C_4)$alkyl at the same time, and wherein Q is a phenyl group substituted with a substituent $X^1$ and optionally with at least one substituent X.

In an [embodiment G] the invention is directed to compounds according to general formula (I-B-1), (I-B-2), (I-B-3), wherein G stands for a substituted phenyl ring G34 wherein k stands for 2, and at least one Z is a halogen atom (preferably F or Cl), which is preferably bound on the 3-position at the phenyl ring and the other Z is a halogen (preferably F or Cl) or a $(C_1\text{-}C_6)$-alkoxy group (preferably methoxy), which is preferably bound on the 4-position at the phenyl ring, and wherein $R^1$ is an $(C_1\text{-}C_6)$-alkyl group (preferably methyl, ethyl, propyl or cyclopropyl) or a $S(O)_x(C_1\text{-}C_4)$-alkyl group (preferably $SCH_3$, $SOCH_3$, and $SO_2CH_3$) or a $(C_1\text{-}C_4)$-alkyl-$S(O)_x(C_1\text{-}C_4)$-alkyl group (preferably $CH_2\text{—}SCH_3$, $CH_2\text{—}SOCH_3$, and $CH_2\text{—}SO_2CH_3$), and wherein Q is a phenyl group substituted with a substituent $X^1$ and optionally with at least one substituent X.

In an [embodiment H] the invention is directed to compounds according to general formula (I-B-1), (I-B-2), (I-B-3), wherein G stands for the thienyl group G1 wherein k stands for 1, and Z is a halogen atom (preferably F or Cl), which is preferably bound on the 5-position at the thienyl ring, and wherein $R^1$ is an $(C_1\text{-}C_6)$-alkyl group (preferably methyl, ethyl, propyl or cyclopropyl) or a $S(O)_x(C_1\text{-}C_4)$-alkyl group (preferably $SCH_3$, $SOCH_3$, and $SO_2CH_3$) or a $(C_1\text{-}C_4)$-alkyl-$S(O)_x(C_1\text{-}C_4)$-alkyl group (preferably $CH_2\text{—}SCH_3$, $CH_2\text{—}SOCH_3$, and $CH_2\text{—}SO_2CH_3$), and wherein Q is a phenyl group substituted with a substituent $X^1$ and optionally with at least one substituent X.

In the context of the present invention, and unless otherwise specified herein, the term "halogen" preferably represents the radicals F, Cl, Br and I, in particular the radicals F and Cl.

Unless otherwise specified, the term $(C_1\text{-}C_6)$-alkyl is understood to mean branched and unbranched alkyl groups consisting of 1 to 6 hydrocarbon atoms. Examples of $(C_1\text{-}C_6)$-alkyl radicals are methyl, ethyl, n-propyl, 1-methylethyl (isopropyl), n-butyl, 1-methylpropyl, 2-methylpropyl, 1,1-dimethylethyl (tert-butyl), n-pentyl, 1-methyl butyl, 2-methyl butyl, 3-methylbutyl, 1,1-dimethylpropyl, 1,2-dimethylpropyl, 2,2-dimethylpropyl, n-hexyl, 1-methylpentyl, 2-methylpentyl, 3-methylpentyl, 4-methylpentyl. $(C_1\text{-}C_4)$-alkyl radicals are preferred, $(C_1\text{-}C_3)$-alkyl radicals being particularly preferred, in particular methyl, ethyl and propyl or propyl. Unless otherwise stated, the definitions of propyl, butyl, pentyl and hexyl encompass all possible isomeric forms of the individual radicals.

Unless otherwise specified, a haloalkyl radical is understood to be an alkyl radical in which at least one hydrogen is exchanged for a halogen atom, preferably fluorine, chlorine, bromine, particularly preferably fluorine. The haloalkyl radicals can be branched or unbranched and optionally mono- or polysubstituted. Preferred haloalkyl radicals are $CHF_2$, $CH_2F$, $CF_3$, $CH_2\text{—}CH_2F$, $CH_2\text{—}CHF_2$, $CH_2CF_3$. $(C_1\text{-}C_6$-haloalkyl radicals are preferred, with $(C_1\text{-}C_4)$-haloalkyl radicals being particularly preferred and $(C_1\text{-}C_3)$-haloalkyl radicals most particularly preferred, in particular $CHF_2$, $CH_2F$, $CF_3$, $CH_2\text{—}CH_2F$, $CH_2\text{—}CHF_2$ and $CH_2CF_3$.

Unless otherwise specified, a haloalkoxy radical is understood to be an alkoxy radical in which at least one hydrogen is exchanged for a halogen atom, preferably fluorine, chlorine, bromine, particularly preferably fluorine. The haloalkoxy radicals can be branched or unbranched and optionally mono- or polysubstituted. Preferred haloalkoxy radicals are $OCHF_2$, $OCH_2F$, $OCF_3$, $OCH_2\text{—}CFH_2$, $OCH_2\text{—}CF_2H$, $OCH_2CF_3$. $(C_1\text{-}C_6)$-haloalkoxy radicals are preferred, with $(C_1\text{-}C_4)$-haloalkoxy radicals being particularly preferred and $(C_1\text{-}C_3)$-haloalkoxy radicals most particularly preferred, in particular $OCHF_2$, $OCH_2F$, $OCF_3$, $OCH_2\text{—}CFH_2$, $OCH_2\text{—}CF_2H$, $OCH_2CF_3$.

Unless otherwise specified, the term $(C_2\text{-}C_6)$-alkenyl is understood to mean branched and unbranched alkyl groups consisting of 2 to 6 hydrocarbon atoms and having at least one double bond. Examples of $(C_2\text{-}C_6)$-alkenyls are ethenyl (also referred to as vinyl), prop-1-enyl, prop-2-enyl (also referred to as allyl), but-1-enyl, but-2-enyl, but-3-enyl, pent-1-enyl and hex-1-enyl. The designation $(C_2\text{-}C_6)$ alkenyl includes all possible isomers, i.e. structural isomers (constitutional isomers) and stereoisomers ((Z) and (E) isomers). Unless otherwise specified, the term "$(C_2\text{-}C_6)$-alkinyl" is understood to mean branched and unbranched unsaturated alkyl groups consisting of 2 to 6 hydrocarbon atoms and having at least one triple bond. Examples of $(C_2\text{-}C_6)$-alkinyls are ethinyl.

Unless otherwise specified, the term carbocycle is understood to mean preferably 3- to 7-membered rings consisting of hydrocarbon groups, which rings can be saturated or unsaturated. Saturated rings are for example cyclopropyl, cyclobutyl, cyclopentyl, cyclohexyl, or cycl heptyl.

Unless otherwise specified, the term heterocycle is understood to mean preferably 3- to 10-membered (preferably 3- to 6-membered) rings consisting of hydrocarbon groups, which rings contain one or more heteroatoms selected from the group comprising nitrogen, oxygen and sulfur, preferably nitrogen and/or oxygen, and which can be saturated or unsaturated. Examples of saturated heterocycles are 1,4-dioxane, tetrahydrofuran, 1,4-oxathiane, azetidinyl, morpholinyl, piperazinyl oxethanyl.

Unless otherwise specified, the term "5- to 10-membered heteroaryl" is understood to represent a 5- to 10-membered cyclic aromatic (condensed) residue containing at least 1, if appropriate also 2, 3, 4 or 5 heteroatoms, wherein the heteroatoms are each preferably selected independently of one another from the group S, N and O, whereas the sulfur atom may exist in oxidized form as SO or $SO_2$ group, and the heteroaryl residue can be unsubstituted or mono- or poly-substituted; e.g. substituted by 2, 3, 4 or 5 substituents, whereby the substituents can be the same or different and be in any desired and possible position of the heteroaryl. Preferred heteroaryls are 5- or 6-membered heteroaryl such as furyl (furanyl), imidazolyl, indazolyl, indolizinyl, indolyl, isoquinolinyl, isoxazoyl, isothiazolyl, indolyl, oxazolyl, oxadiazolyl, phenazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl. The binding to the superordinate general structure can be carried out via any desired and possible ring member of the heteroaryl residue if not indicated otherwise. The heteroaryl may be unsubstituted or mono- or polysubstituted; e.g. substituted by 2, 3, 4 or 5 substituents, whereby the substituents can be the same or different and be in any desired and possible position.

Owing to their excellent pharmacological activity, the compounds according to the first aspect of the invention, in particular according to the general structure of formulae (I), (I-A), (I-B), (I-B-1) (I-B-2), (I-B-3), (I-C) and (I-D) are suitable for the treatment of various diseases or conditions in which inhibition of the PDE4 enzyme is advantageous.

Such conditions and diseases are inter alia
inflammatory diseases of the joints, in particular rheumatoid arthritis, psoriatic arthritis, ankylosing spondylitis (Bechterew's disease), gout, osteoarthritis;
inflammatory diseases of the skin, in particular psoriasis, atopic dermatitis, lichen planus;
inflammatory diseases of the eyes, in particular uveitis;
gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps;
inflammatory diseases of the internal organs, in particular SLE (systemic lupus erythematosus) including lupus nephritis, chronic prostatitis, interstitial cystitis;
hyperplastic diseases, in particular benign prostatic hyperplasia;
respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia;
diseases of the fibrotic spectrum, in particular hepatic fibrosis, systemic sclerosis, scleroderma;
cancers, in particular haematopoietic cancers, inter alia B-cell lymphoma, T-cell lymphoma, in particular CLL and CML (chronic lymphatic and chronic myeloid leukaemia), ALL and AML (acute lymphatic and acute myeloid leukaemia), and gliomas;
metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension);
psychological disorders, in particular schizophrenia, depression, in particular bipolar or manic depression, dementia, memory loss, generalised anxiety disorder (GAD); and
diseases of the peripheral or central nervous system, in particular Parkinson's disease, multiple sclerosis, Alzheimer's disease, stroke, ALS (amyotrophic lateral sclerosis).

One of the advantages of the compounds according to the first aspect of the invention is that they are selective PDE4B inhibitors. The advantage of this selectivity lies in the fact that the PDE4D enzyme for example is not inhibited or is only partly inhibited, and hence the use of such selective PDE4B inhibitors gives rise to no side-effects or to markedly reduced side-effects. Undesired side-effects are for example emesis and nausea, in particular indisposition, vomiting and sickness. The therapeutic range of the compounds according to the invention is therefore advantageous.

In a second aspect of the invention, the invention therefore also provides a pharmaceutical composition (medicament) containing at least one compound according to the first aspect of the invention, in particular according to the general structure of formulae (I), (I-A), (I-B), (I-B-1) (I-B-2), (I-B-3), (I-C) and (I-D) in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio.

In a third aspect of the invention, the invention therefore also provides a compound according to the first aspect of the invention, in particular according to formulae (I), (I-A), (I-B), (I-B-1) (I-B-2), (I-B-3), (I-C) and (I-D) in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio for use as a medicament, in particular for the treatment of conditions or diseases that can be treated by inhibition of the PDE4 enzyme, in particular the PDE4B enzyme.

In a fourth aspect of the invention, the invention therefore also provides a compound according to the first aspect of the invention, in particular according to formulae (I), (I-A), (I-B), (I-B-1) (I-B-2), (I-B-3), (I-C) and (I-D) in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio for the treatment of inflammatory diseases of the joints, in particular rheumatoid arthritis, psoriatic arthritis, ankylosing spondylitis (Bechterew's disease), gout, osteoarthritis; and/or inflammatory diseases of the skin, in particular psoriasis, atopic dermatitis, lichen planus; and/or inflammatory diseases of the eyes, in particular uveitis; gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps; inflammatory diseases of the internal organs, in particular SLE (systemic lupus erythematosus) including lupus nephritis, chronic prostatitis, interstitial cystitis; and/or hyperplastic diseases, in particular benign prostatic hyperplasia; respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; diseases of the fibrotic spectrum, in particular hepatic fibrosis, systemic sclerosis, scleroderma; cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas; metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension); psychological disorders, in particular schizophrenia, depression, in particular bipolar or manic depression, dementia, memory loss, generalised anxiety disorder (GAD); and/or diseases of the peripheral or central nervous system, in particular Parkinson's disease, multiple sclerosis, Alzheimer's disease, stroke, ALS (amyotrophic lateral sclerosis).

In a preferred embodiment of the fourth aspect of the invention, the invention therefore provides a compound according to the first aspect of the invention, in particular of formulae (I), (I-A), (I-B), (I-B-1) (I-B-2), (I-B-3), (I-C) and (I-D) in the presented form or in the form of its acids or bases or in the form of the pharmaceutically safe, in particular physiologically acceptable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio for the treatment of inflammatory diseases of the joints (in particular rheumatoid arthritis, psoriatic arthritis, ankylosing spondylitis (Bechterew's disease), gout, osteoarthritis), the skin (in particular psoriasis, atopic dermatitis, lichen planus) or the eyes (in particular uveitis), of respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; of metabolic diseases, in particular type 2 diabetes, metabolic syndrome, obesity/adiposity, fatty liver disease (not alcohol-induced), and/or cardiovascular diseases, in particular arteriosclerosis, PAH (pulmonary arterial hypertension).

In another aspect of the invention, the invention also provides the use of a compound according to the first aspect of the invention, in particular according to the general structure of formulae (I), (I-A), (I-B), (I-B-1) (I-B-2), (I-B-3), (I-C) and (I-D) in the presented form or in the form of its acids or bases or in the form of the pharmaceutically safe, in particular physiologically acceptable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of diseases and conditions according to the fourth aspect of the invention.

In yet another aspect of the invention, the invention also provides a method for the treatment of the diseases and conditions according to the fourth aspect of the invention in a human, which is characterised in that a therapeutically effective amount of at least one compound according to the first aspect of the invention, in particular according to the general structure of formulae (I), (I-A), (I-B), (I-B-1) (I-B-2), (I-B-3), (I-C) and (I-D) in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio, is administered.

The amount of active ingredient to be administered to the person or patient varies and is dependent on the patient's weight, age and medical history and on the type of administration, the indication and the severity of the illness. Generally 0.01 to 500 mg/kg, in particular 0.05 to 50 mg/kg, preferably 0.1 to 25 mg/kg of body weight of at least one compound according to the first aspect of the invention, in particular according to the general structure of formula (I), (I-A), (I-B), (I-B-1) (I-B-2), (I-B-3), (I-C) and (I-D) in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio, are administered.

All embodiments, in particular the preferred embodiments, of the first aspect of the invention apply mutatis mutandis to all other aspects of the invention.

The medicaments, drugs and pharmaceutical compositions according to the invention can take the form of and be administered as liquid, semi-solid or solid dosage forms and as for example injection solutions, drops, juices, syrups, sprays, suspensions, granules, tablets, pellets, transdermal therapeutic systems, capsules, plasters, suppositories, ointments, creams, lotions, gels, emulsions or aerosols and contain, in addition to at least one compound according to the first aspect of the invention, in particular according to the general structure of formula (I), (I-A), (I-B), (I-B-1) (I-B-2), (I-B-3), (I-C) and (I-D) in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio, according to the pharmaceutical form and depending on the administration route, pharmaceutical auxiliary substances such as for example carrier materials, fillers, solvents, diluting agents, surface-active substances, dyes, preservatives, disintegrants, slip additives, lubricants, flavourings and/or binders.

The choice of auxiliary substances and the amounts thereof to use depends on whether the medicament/drug is to be administered by oral, subcutaneous, parenteral, intravenous, vaginal, pulmonary, intraperitoneal, transdermal, intramuscular, nasal, buccal or rectal means or locally, for example for infections of the skin, mucous membranes and eyes. Preparations in the form of inter alia tablets, pastilles, capsules, granules, drops, juices and syrups are suitable for oral administration; solutions, suspensions, easily reconstitutable powders for inhalation and sprays are suitable for parenteral, topical and inhalative administration. Compounds according to the first aspect of the invention in a depot formulation, in dissolved form or in a plaster, optionally with addition of agents promoting skin penetration, are suitable preparations for percutaneous administration. Preparation forms that are suitable for rectal, transmucosal, parenteral, oral or percutaneous administration can deliver the compounds according to the first aspect of the invention, on a delayed release basis.

Preparation of the medicaments and pharmaceutical compositions according to the invention takes place using agents, equipment, methods and procedures that are well-known from the prior art of pharmaceutical formulation, such as are described for example in "Remington's Pharmaceutical Sciences", Ed. A. R. Gennaro, 17th edition, Mack Publishing Company, Easton PD (1985), in particular in part 8, chapters 76 to 93.

The compounds according to the invention can be produced in the manner described here or in an analogous manner.

Unless indicated otherwise, the compounds according to the first aspect of invention can be synthesized according to general knowledge in the field of organic chemistry or in a manner as described here (cf. reaction schemes below) or analogously. The reaction conditions in the synthesis routes described herein are known to the skilled person and are for some cases exemplified in the synthesis examples herein.

The compounds according to the invention can be synthesized according to general knowledge in the field of organic chemistry or in a manner as described here (cf. reaction schemes below) or analogously. The reaction conditions in the synthesis routes described herein are known to the skilled person and are for some cases exemplified in the synthesis examples herein.

In the reaction schemes the following abbreviations are used: Tf=trifluoromethanesulfonyl; Boc=tert-butoxycarbonyl, DMAP=4-(Dimethylamino)-pyridin, DIPEA=Diisopropylethylamine.

If not stated otherwise, all chemical groupings and indices in the compounds shown in the following reaction schemes are as defined in the context of the compound of formula (I).

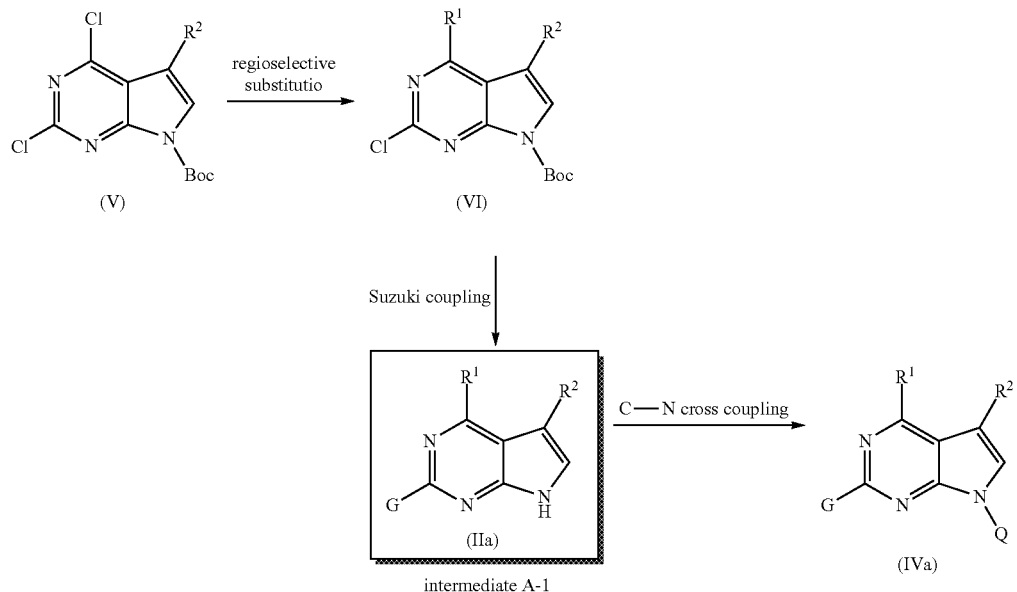

Intermediate A-1 of general formula (IIa) can be prepared by subjecting a compound of formula (V) to a regioselective substitution to produce a compound of formula (VI) which is then subjected to a Suzuki coupling to yield the desired intermediate A-1.

Regioselective C—C coupling reactions for compounds such as (V) are generally known in the art. [cf. S. Turnkevicius at al, *Tetrahedron Lett.*, 2010, 3902]. Regioselective substitutions with nucleophiles such as MeSNa are also known in the art [cf. H. Z. Yang et al, *Journal of Heterocyclic Chemistry*, 2007, 44, 967].

The Suzuki coupling is known in the art [cf. A. Suzuki, N. Miyaura, *Chem. Rev.*, 1995, 95, 2457].

Compound of formula (V) can be synthesized from commercially available 2,4-dichloro-7H-pyrrolo[2,3-d]pyrimidine (X) using BOC-anhydride, DIPEA and catalytic amounts of DMAP in dichloromethane [cf. T. W. Green, P. G. M. Wuts, *Protective Groups in Organic Synthesis*, Wiley-Interscience, New York, 1999, 518-525].

Reaction scheme 2:

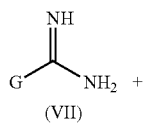
(VII)

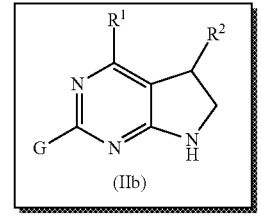
intermediate A-2

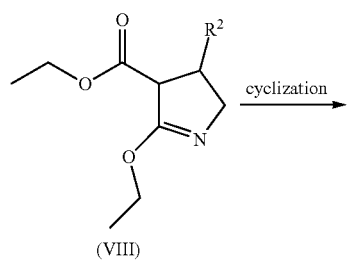
(VIII)

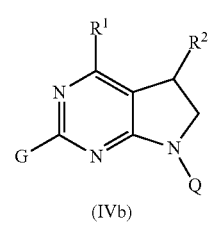
(IVb)

Intermediate A-2 of general formula (IIb) can be prepared by subjecting compound of formula (VII) and a compound of formula (VIII) to a cyclization reaction which yields a compound of formula (IX). The conditions for such a cyclization reaction are known in the art [cf. L. Provins et al, Bioorg. Med. Chem. Lett., 2006, 16, 1834] and are for example stirring compounds (VII) and (VIII) in toluene at 100° C. for 16 hours. The cyclized precursor can be modified using trifluormethansulfonic acid and catalytic amounts of DMAP followed by addition of BOC-anhydride and DIPEA in dichloromethane to give access to compound of formula (IX).

The compound of formula (IX) is then subjected to a C—C coupling reaction which yields intermediate A-2 of formula (IIb). C—C coupling reactions are generally known in the art. Favorable C—C coupling reactions are either palladium or iron catalyzed cross coupling reactions [cf. M. S. Sigman et al, Chem. Rev. 2011, 111, 1417].

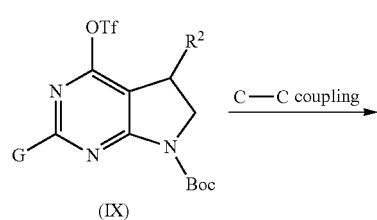
(IX)

Reaction scheme 3:

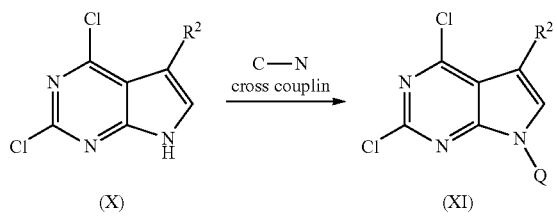

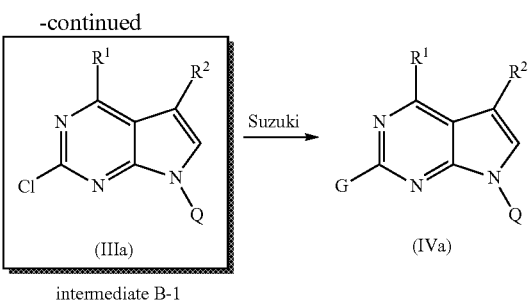

intermediate B-1

Intermediate B-1 of formula (IIIa) can be prepared by a C—N cross coupling reaction from commercially available compound of formula (X).

Suitable C—N cross coupling reactions are known in the art [cf. P. Y. S. Lam et al, *Synthesis*, 2011, 829; S. L. Buchwald et al, *Chem. Sci.*, 2011, 2, 27] and can be conducted by adding a boronic acid, $Cu(OAc)_2$ and triethylamine to a stirred solution of commercially available compound (X) in THF.

The thus prepared compound of formula (XI) is then subjected to a regioselective substitution which can be a C—C cross coupling but also a S—C coupling using NaSMe to yield intermediate B-1 of formula (IIIa) (see corresponding reaction given in reaction scheme 1).

*Journal of Chemistry*, 1962, 40, 1403] and can be conducted for example using concentrated hydrochloric acid in ethanol at increased temperature.

The thus prepared compound of formula (XIV) is then subjected to a cyclization reaction to give the compound of formula (XV). Cyclization reactions are generally known [cf. J. D. Fissekis et al, *JOC*, 1964, 29, 2670]. A suitable cyclization reaction can be done by addition of a base such as sodium methylate.

The compound of formula (XV) is then subjected to a chlorination reaction giving a compound of formula (XVI).

Reaction scheme 4:

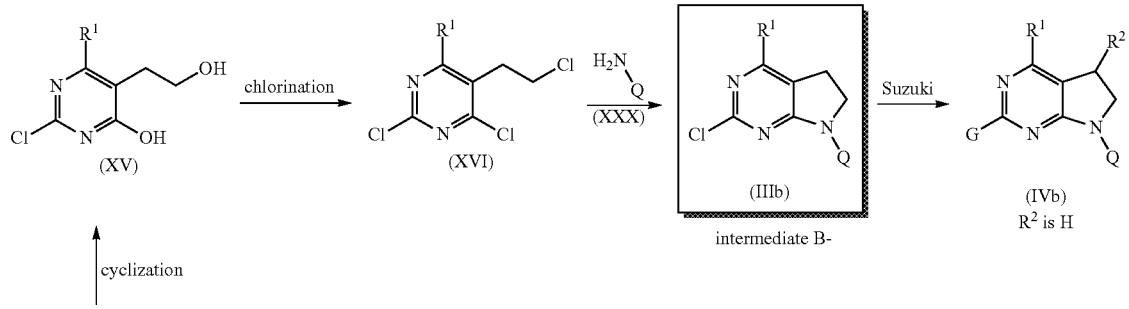

intermediate B-

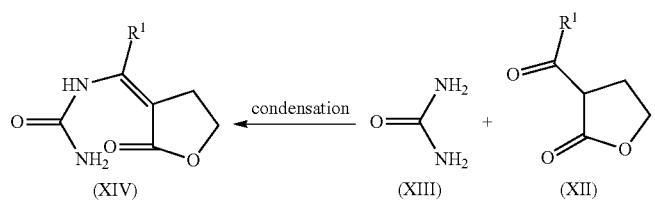

Intermediate B-2 of formula (IIIb) can be prepared by subjecting a compound of formula (XII) and a compound of formula (XIII) to a condensation reaction to produce a compound of formula (XIV). Condensation reactions with urea are known in the art [cf. C. Podesva et al, *Canadian*

The chlorination can be done by using phosphoryl trichloride.

Then the compound of formula (XVI) is reacted with a compound of formula (XXX) which yields the intermediate B-2. This reaction represents another cyclization reaction.

This cyclization can take place at increased temperature after addition of Na$_2$CO$_3$ to a solution of a compound of formula (XVI) in DMF.

Compounds of formula (XXX) are commercially available or can be prepared according to methods known in the art.

The thus prepared compound of formula (XXII) is then subjected to a C—N cross coupling reaction. C—N cross coupling reactions are known in the art and can be performed with CuI, K$_3$PO$_4$ and cyclohexa-1,2-diamine in 1,4-dioxane at increased temperature [cf. I. P. Beletskaya et al., *Coordination Chemistry Reviews*, 2004, 2337].

Reaction scheme 5:

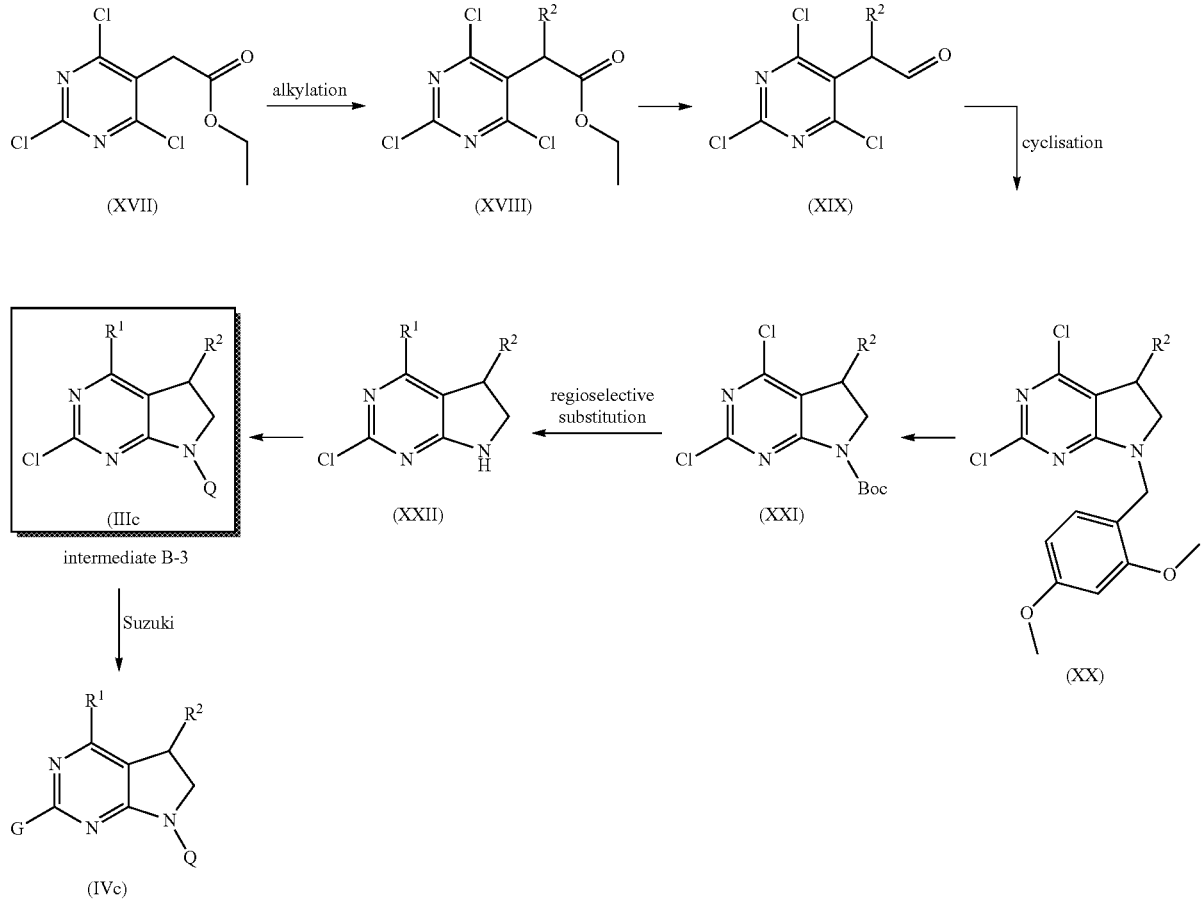

Intermediate B-3, wherein R$^2$ is not hydrogen can alternatively be synthesized starting from commercially available compound of formula (XVII). R$^2$ can be introduced via alkylation of the preformed ester enolate to give (XVIII). Alkylation of ester enolates are known in the art [cf. R. Brückner: *Reaktionsmechanismen*. 3. Auflage, Spektrum Akademischer Verlag, München, 2004, 516]. Compound of formula (XVIII) is reduced to give compound (XIX). The compound of formula (XIX) is then reacted with (2,4-dimethoxyphenyl)methanamine which yields compound (XX). This reaction represents another cyclization reaction which is similar to the reaction of (XVI) to (IIIb) and is described above.

Modification of the N-protecting group of compound (XX) gives compound (XXI) which can undergo a regioselective substitution. Protection of amino groups is known in the art [cf. T. W. Green, P. G. M. Wuts, *Protective Groups in Organic Synthesis*, Wiley-Interscience, New York, 1999, 494-653]. Regioselective substitutions can be performed under reaction conditions that are described above in the reaction starting with the compound of formula (V) to yield the compound of formula (VI).

Reaction scheme 6:

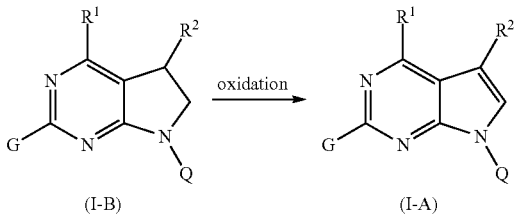

If desired, a compound of formula (I-B) can be oxidized to give a compound of formula (I-A) by subjecting the compound of formula (I-B) to a oxidation reaction in the presence of an oxidation agent. Oxidation reactions are known in the art [cf. Hudlicky, M., *Oxidations in Organic Chemistry*, ACS Monograph Series; American Chemical Society:Washington D.C., 1990]. Suitable oxidation agents are for example MnO$_2$ (see also reaction scheme 3).

Reaction scheme 7:

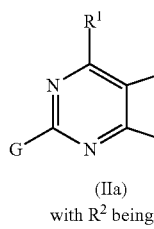

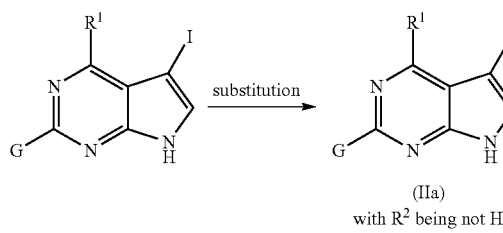

Reaction scheme 8:

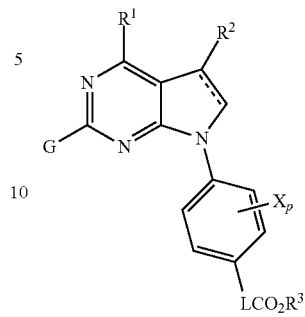

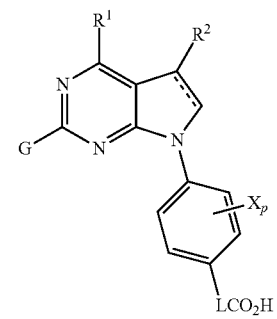

The compound of formula (IIa) wherein $R^2$ is hydrogen can be converted to the compound of the same general structure wherein $R^2$ is defined as above in the context of the compound of formula (I), however without hydrogen, via a iodination followed by nucleophilic substitution with nucleophiles like NaSMe or MeSO$_2$Na.

Iodinations are known in the art (cf. J. Arotsky et al., *J. Chem. Soc., Perkin Trans.* 2, 1973, 595-599). Nucleophilic substitution can be conducted as described above in the context the reaction of compound (V) to compound (VI).

Compounds of formula (I) wherein Q stands for Q1 and wherein $R^3$ stands for $CH_3$, $CH_2CH_3$ or $C(CH_3)_3$ can be converted to compounds of formula (I) wherein Q stands for Q1 and and $R^3$ stands for hydrogen by an acid or basic ester cleavage according to known methods [cf. T. W. Green, P. G. M. Wuts, *Protective Groups in Organic Synthesis*, Wiley-Interscience, New York, 1999, 154-155].

The compounds according to the invention can be produced in the manner described here or in an analogous manner.

The compounds according to the invention are specified in the tables below, without limiting the invention thereto.

TABLE 1

| Cpd-No. | structure according to formula | G | Z | R1 | R2 or R2a, R2b | Q | X | p |
|---|---|---|---|---|---|---|---|---|
| 1 | I-A | G35 | 3-F, 4-OMe | Me | H | Q2 | — | 0 |
| 2 | I-A | G35 | 3-F, 4-OMe | Et | H | Q2 | — | 0 |
| 3 | I-A | G35 | 3-F, 4-OMe | Me | H | Q3 | — | 0 |
| 4 | I-A | G35 | 3-F, 4-OMe | Et | H | Q3 | — | 0 |
| 5 | I-B | G35 | 3-F, 4-OMe | Me | H, H | Q2 | — | 0 |
| 6 | I-B | G35 | 3-F, 4-OMe | Et | H, H | Q2 | — | 0 |
| 7 | I-B | G35 | 3-F, 4-OMe | Me | H, H | Q3 | — | 0 |
| 8 | I-B | G35 | 3-F, 4-OMe | Et | H, H | Q3 | — | 0 |
| 10 | I-B | G35 | 3-F, 4-OMe | Me | Me, H | Q2 | — | 0 |
| 11 | I-B | G35 | 3-F, 4-OMe | Et | Me, H | Q2 | — | 0 |
| 12 | I-B | G35 | 3-F, 4-OMe | Me | Me, H | Q3 | — | 0 |
| 13 | I-B | G35 | 3-F, 4-OMe | Et | Me, H | Q3 | — | 0 |
| 14 | I-A | G35 | 3-Cl, 4-OMe | Me | H | Q2 | — | 0 |
| 15 | I-A | G35 | 3-Cl, 4-OMe | Et | H | Q2 | — | 0 |
| 16 | I-A | G35 | 3-Cl, 4-OMe | Me | H | Q3 | — | 0 |
| 17 | I-A | G35 | 3-Cl, 4-OMe | Et | H | Q3 | — | 0 |
| 18 | I-B | G35 | 3-Cl, 4-OMe | Me | H, H | Q2 | — | 0 |
| 19 | I-B | G35 | 3-Cl, 4-OMe | Et | H, H | Q2 | — | 0 |
| 20 | I-B | G35 | 3-Cl, 4-OMe | Me | H, H | Q3 | — | 0 |
| 21 | I-B | G35 | 3-Cl, 4-OMe | Et | H, H | Q3 | — | 0 |
| 22 | I-B | G35 | 3-Cl, 4-OMe | Me | Me, H | Q2 | — | 0 |
| 23 | I-B | G35 | 3-Cl, 4-OMe | Et | Me, H | Q2 | — | 0 |
| 24 | I-B | G35 | 3-Cl, 4-OMe | Me | Me, H | Q3 | — | 0 |
| 25 | I-B | G35 | 3-Cl, 4-OMe | Et | Me, H | Q3 | — | 0 |
| 26 | I-A | G35 | 3-F, 4-F | Me | H | Q2 | — | 0 |
| 27 | I-A | G35 | 3-F, 4-F | Et | H | Q2 | — | 0 |

TABLE 1-continued

| Cpd-No. | structure according to formula | G | Z | R1 | R2 or R2a, R2b | Q | X | p |
|---|---|---|---|---|---|---|---|---|
| 28 | I-A | G35 | 3-F, 4-F | Me | H | Q3 | — | 0 |
| 29 | I-A | G35 | 3-F, 4-F | Et | H | Q3 | — | 0 |
| 30 | I-B | G35 | 3-F, 4-F | Me | H, H | Q2 | — | 0 |
| 31 | I-B | G35 | 3-F, 4-F | Et | H, H | Q2 | — | 0 |
| 32 | I-B | G35 | 3-F, 4-F | Me | H, H | Q3 | — | 0 |
| 33 | I-B | G35 | 3-F, 4-F | Et | H, H | Q3 | — | 0 |
| 34 | I-B | G35 | 3-F, 4-F | Me | Me, H | Q2 | — | 0 |
| 35 | I-B | G35 | 3-F, 4-F | Et | Me, H | Q2 | — | 0 |
| 36 | I-B | G35 | 3-F, 4-F | Me | Me, H | Q3 | — | 0 |
| 37 | I-B | G35 | 3-F, 4-F | Et | Me, H | Q3 | — | 0 |
| 38 | I-A | G5 | 3-Cl | Me | H | Q2 | — | 0 |
| 39 | I-B | G5 | 3-Cl | Me | H, H | Q3 | — | 0 |
| 41 | I-A | G5 | 3-Cl | OMe | H | Q2 | — | 0 |
| 42 | I-A | G35 | 3-F, 4-Me | Me | $SO_2Me$ | Q2 | — | 0 |
| 43 | I-A | G35 | 3-F, 4-Me | $SO_2Me$ | H | Q2 | — | 0 |
| 44 | I-A | G35 | 3-F, 4-Me | $CH_2SO_2Me$ | H | Q2 | — | 0 |
| 45 | I-A | G35 | 3-Cl, 4-OMe | OMe | H | Q2 | — | 0 |
| 46 | I-B | G5 | 3-Cl | Et | H, H | Q2 | — | 0 |
| 57 | I-A | G35 | 3-F, 4-OMe | $SO_2Me$ | H | Q3 | — | 0 |
| 69 | I-A | G35 | 3-F, 4-OMe | SMe | H | Q3 | — | 0 |
| 71 | I-A | G35 | 3-F, 4-OMe | Me | $SO_2Me$ | Q3 | — | 0 |
| 84 | I-B | G36 | — | Et | H, H | Q2 | — | 0 |
| 86 | I-B | G35 | 3-OMe, 4-F | Et | H, H | Q3 | — | 0 |
| 89 | I-B | G36 | — | Et | H, H | Q3 | — | 0 |
| 90 | I-B | G35 | 4-$OCHF_2$ | Et | H, H | Q3 | — | 0 |
| 93 | I-B | G37 | — | Et | H, H | Q3 | — | 0 |
| 96 | I-B | G34 | 4-OEt | Et | H, H | Q3 | — | 0 |
| 98 | I-B | G34 | 3-OEt | Et | H, H | Q2 | — | 0 |
| 99 | I-B | G35 | 3-Cl, 4-F | Et | H, H | Q3 | — | 0 |

TABLE 2

| Cpd-No. | structure according to formula | G | Z | R1 | R2 or R2a, R2b | Q | R4 |
|---|---|---|---|---|---|---|---|
| 9 | I-B | G35 | 3-F, 4-OMe | Et | H, H | Q14 | $NMe_2$ |
| 40 | I-B | G5 | 3-Cl | Et | H, H | Q14 | $NMe_2$ |
| 47 | I-B | G35 | 3-F, 4-OMe | Et | H, H | Q14 | 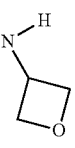 |
| 48 | I-B | G35 | 3-F, 4-OMe | Et | H, H | Q14 |  |
| 49 | I-A | G35 | 3-F, 4-OMe | Et | H | Q14 | 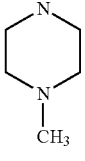 |
| 50 | I-A | G35 | 3-F, 4-OMe | $SO_2Me$ | H | Q14 | $NMe_2$ |
| 51 | I-B | G35 | 3F, 4-OMe | Et | H, H | Q14 |  |
| 52 | I-A | G35 | 3-F, 4-OMe | Et | H | Q14 | $NHCHMe_2$ |
| 53 | I-A | G35 | 3-F, 4-OMe | Et | H | Q14 |  |

TABLE 2-continued

| Cpd-No. | structure according to formula G | Z | R1 | R2 or R2a, R2b | Q | R4 |
|---|---|---|---|---|---|---|
| 54 | I-A | G35 | 3-F, 4-OMe | Et | H | Q14 |  |
| 55 | I-A | G35 | 3F, 4-OMe | Et | H | Q14 | 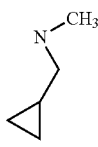 |
| 56 | I-B | G35 | 3-F, 4-OMe | Et | H, H | Q14 | NH(CH$_2$)$_2$OH |
| 58 | I-A | G35 | 3-F, 4-OMe | SMe | H | Q14 | NMe$_2$ |
| 59 | I-A | G35 | 3-F, 4-OMe | Et | H | Q14 |  |
| 60 | I-B | G35 | 3-F, 4-OMe | Et | H, H | Q14 | NHEt |
| 61 | I-A | G35 | 3-F, 4-OMe | Et | H | Q14 |  |
| 62 | I-A | G35 | 3-F, 4- OMe | Et | H | Q14 | NH$_2$ |
| 63 | I-A | G35 | 3-F, 4-OMe | Et | H | Q14 | NHEt |
| 64 | I-B | G35 | 3-F, 4-OMe | Et | H, H | Q14 | NH$_2$ |
| 65 | I-B | G35 | 3-F, 4-OMe | Et | H, H | Q14 | NHMe |
| 66 | I-A | G35 | 3-F, 4-OMe | Et | H | Q14 | NHMe |
| 67 | I-A | G35 | 3-F, 4-OMe | Et | H | Q14 | NH(CH$_2$)$_2$OH |
| 68 | I-B | G35 | 3-F, 4-OMe | Et | H, H | Q14 | 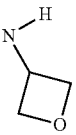 |
| 70 | I-A | G35 | 3-F, 4-OMe | Me | SO$_2$Me | Q14 | NMe$_2$ |
| 72 | I-A | G35 | 3-F, 4-OMe | Me | SMe | Q14 | NMe$_2$ |
| 73 | I-B | G35 | 3-F, 4-OMe | Et | H, H | Q15 | NMe$_2$ |
| 74 | I-B | G5 | 3-Cl | Et | H, H | Q15 | NMe$_2$ |
| 75 | I-A | G35 | 3-F, 4-OMe | Et | H | Q15 | NMe$_2$ |
| 76 | I-A | G35 | 3-F, 4-OMe | cyclpropyl | H | Q14 | NMe$_2$ |
| 77 | I-A | G27 | 4-OMe | Et | H | Q14 | NMe$_2$ |
| 78 | I-B-1 (n = 1) | G35 | 3-F, 4-OMe | H | — | Q14 | NMe$_2$ |
| 79 | I-B-1 (n = 1) | G35 | 3-F, 4-OMe | Me | — | Q14 | NMe$_2$ |
| 80 | I-A | G27 | 2-OMe | Et | H | Q14 | NMe$_2$ |
| 81 | I-A | G34 | 3-SO$_2$Me | Et | H | Q14 | NMe$_2$ |
| 82 | I-A | G28 | — | Et | H | Q14 | NMe$_2$ |
| 83 | I-A | G27 | | Et | H | Q14 | NMe$_2$ |
| 85 | I-A | G35 | 3-F, 4-OMe | Et | H | Q14 | NMe$_2$ |
| 87 | I-A | G39 | — | Et | H | Q14 | NMe$_2$ |
| 88 | I-A | G37 | — | Et | H | Q14 | NMe$_2$ |
| 91 | I-A | G34 | 4-SO$_2$Me | Et | H | Q14 | NMe$_2$ |
| 92 | I-A | G35 | 3-Cl, 4-OMe | Et | H | Q14 | NMe$_2$ |
| 94 | I-A | G34 | 4-OMe | Et | H | Q14 | NMe2 |
| 95 | I-A | G34 | 4-OEt | Et | H | Q14 | NMe$_2$ |
| 97 | I-A | G31 | — | Et | H | Q14 | NMe$_2$ |

The following abbreviations are used in the descriptions of the experiments:
DMF=N,N-dimethylformamid; DMSO=dimethylsulfoxid; h=hour; min=minute; Rt=retention time; tert=tertiary; THF=tetrahydrofuran; LiHMDS=lithium bis(trimethylsilyl) amide; RT=room temperature; DCM=dichloromethane; DMAP=4-(dimethylamino)-pyridine; DIPEA=N,N-diisopropylethylamine; dppf=1,1'-bis(diphenylphosphanyl)ferrocene; TMSCl=trimethylsilyl chloride; BINAP=2,2'-bis(diphenylphosphino)-1,1'-binaphthyl; Et=ethyl; dba=dibenzylideneacetone; Boc=tert-butyloxycarbonyl; Bu=butyl; Tf=triflate The following analytical HPLC/MS methods were used:
Method 1:
Column: Agilent Zorbax Extend, 1.8 μm, 4.6×30 mm; Detection: 254 nm (or 215 nm)
Mobile phase A: water/0.1% formic acid; Mobile phase B: acetonitrile/0.1% formic acid
Gradient:

| Time in min | % A | % B | Flow rate in ml/min |
| --- | --- | --- | --- |
| 0.0 | 95.0 | 5.0 | 2.5 |
| 3.0 | 5.0 | 95.0 | 2.5 |
| 3.01 | 5.0 | 95.0 | 4.5 |
| 3.6 | 5.0 | 95.0 | 4.5 |
| 3.7 | 95.0 | 5.0 | 2.5 |
| 4.0 | 95.0 | 5.0 | 2.5 |

Synthesis Example No. 1 preparation of 4-(2-(3-Fluoro-4-methoxyphenyl)-4-methyl-7H-pyrrolo[2,3-d]pyrimidin-7-yl)benzoic acid (compound No. 1)

1a): Methyl 4-(2-chloro-4-methyl-7H-pyrrolo[2,3-d]pyrimidin-7-yl)benzoate 4-(Methoxycarbonyl)phenylboronic acid (2.88 g, 16 mmol), triethylamine (2.22 ml, 16 mmol), Cu(OAc)$_2$ and powdered 4 Å molecular sieve (4.18 g) were subsequently added to a solution of 2,4-dichloro-7H-pyrrolo[2,3-d]pyrimidine (1.5 g, 8 mmol) in 1,2-dichloroethane (30 ml). The reaction mixture was stirred for 120 h at 23° C. THF (75 ml) was added and the solution was filtered over Celite® to remove solids. The filtrate was concentrated under reduced pressure and the residue was purified by flash chromatography to give methyl 4-(2,4-dichloro-7H-pyrrolo[2,3-d]pyrimidin-7-yl)benzoate (1.67 g, 64%) as a white solid (purity 65% according to $^1$H NMR) which was used for the next step without further purification. To a suspension of methyl 4-(2,4-dichloro-7H-pyrrolo[2,3-d]pyrimidin-7-yl)benzoate (1.50 g, purity 65%, 4.66 mmol) in THF (15 ml) ferric acetylacetonate (350 mg, 0.99 mmol), 1-methyl-2-pyrrolidone (750 μl, 7.33 mmol) and methylmagnesium bromide (3.5 ml, 4.90 mmol, 1.4M solution in toluene:THF=3:1) were subsequently added and the reaction mixture was stirred for 66 h at 23° C. Saturated aqueous ammonium chloride solution (50 ml) was added and the crude product was extracted with ethyl acetate (3×40 ml). The combined organic layers were dried over MgSO$_4$, filtered and concentrated in vacuo. The residue was purified by flash chromatography to give methyl 4-(2-chloro-4-methyl-7H-pyrrolo[2,3-d]pyrimidin-7-yl)benzoate (705 mg, 77%) as a white solid (705 mg, 77%).

$^{13}$C-NMR (101 MHz, DMSO-d$_6$, δ ppm): 21.5, 52.3, 102.0, 117.8, 122.9, 127.5, 128.6, 131.1, 140.7, 151.3, 154.2, 166.2, 166.2

1b): Methyl 4-(2-(3-fluoro-4-methoxyphenyl)-4-methyl-7H-pyrrolo[2,3-d]pyrimidin-7-yl)benzoate Under an argon atmosphere 3-fluoro-4-methoxyphenylboronic acid (110 mg, 0.65 mmol) and [1,1'-bis(diphenylphosphino)ferrocene]dichloropalladium(II) complex with dichloromethane (45 mg, 0.06 mmol, 1:1) were added to a suspension of methyl 4-(2-chloro-4-methyl-7H-pyrrolo[2,3-d]pyrimidin-7-yl)benzoate (150 mg, 0.50 mmol) and Cs$_2$CO$_3$ (492 mg, 1.51 mmol) in dry 1,4-dioxane (1.5 ml). The reaction mixture was heated up to 100° C. for 1.5 h. The crude product was purified by flash chromatography to give methyl 4-(2-(3-fluoro-4-methoxyphenyl)-4-methyl-7H-pyrrolo[2,3-d]pyrimidin-7-yl)benzoate (143 mg, 73%) as a colorless solid.

$^{13}$C-NMR (101 MHz, DMSO-d$_6$, δ ppm): 21.4, 52.1, 56.0, 102.3, 113.5, 114.4, 114.6, 117.0, 122.3, 124.1, 124.2, 126.8, 127.8, 130.4, 131.0, 131.1, 141.2, 148.6, 148.7, 150.2, 150.7, 152.6, 155.9, 156.0, 160.0, 165.6
LC-MS (method 1): m/z: [M+H]$^+$=392.2, R$_t$=4.25 min 1c): 4-(2-(3-Fluoro-4-methoxyphenyl)-4-methyl-7H-pyrrolo[2,3-d]pyrimidin-7-yl)benzoic acid To a suspension of methyl 4-(2-(3-fluoro-4-methoxyphenyl)-4-methyl-7H-pyrrolo[2,3-d]pyrimidin-7-yl)benzoate (138 mg, 0.35 mmol) in methanol (3 ml) and 1,4-dioxane (3 ml) was added 1N NaOH (0.71 ml, 0.71 mmol) and the reaction mixture was stirred for 15 min at 80° C. The solution was filtered and the filtrate was neutralized by addition of 1N HCl (0.71 ml, 0.71 mmol). The precipitate was filtered and washed with water (3×5 ml) and methanol (3×2 ml). The obtained colorless crystals were dried under vacuo to give of 4-(2-(3-fluoro-4-methoxyphenyl)-4-methyl-7H-pyrrolo[2,3-d]pyrimidin-7-yl)benzoic acid (99 mg; 75%).

$^{13}$C-NMR (101 MHz, DMSO-d$_6$, δ ppm): 21.4, 56.0, 102.2, 113.5, 114.5, 114.6, 114.6, 117.0, 122.4, 124.1, 127.9, 128.2, 130.5, 131.0, 131.1, 140.9, 148.6, 148.7, 150.2, 150.5, 152.6, 155.9, 156.0, 160.0, 166.7

Synthesis Example No. 2 preparation of: 4-(2-(3-Chloro-4-methoxyphenyl)-4-methyl-7H-pyrrolo[2,3-d]pyrimidin-7-yl)benzoic acid (compound No. 14)

2a): Methyl 4-(2-(3-chloro-4-methoxyphenyl)-4-methyl-7H-pyrrolo[2,3-d]pyrimidin-7-yl)benzoate Under an argon atmosphere 3-chloro-4-methoxyphenylboronic acid (120 mg, 0.64 mmol) and [1,1'-bis(diphenylphosphino)ferrocene]dichloropalladium(II) complex with dichloromethane (45 mg, 0.06 mmol, 1:1) were added to a suspension of methyl 4-(2-chloro-4-methyl-7H-pyrrolo[2,3-d]pyrimidin-7-yl)benzoate (150 mg, 0.50 mmol) and Cs$_2$CO$_3$ (570 mg, 1.75 mmol) in dry 1,4-dioxane (1.6 ml). The reaction mixture was heated up to 100° C. for 1 h. The crude product was purified by flash chromatography to give methyl 4-(2-(3-chloro-4-methoxyphenyl)-4-methyl-7H-pyrrolo[2,3-d]pyrimidin-7-yl)benzoate (162 mg, 68%) as a white solid.

$^{13}$C-NMR (101 MHz, CDCl$_3$, δ ppm): 21.8, 52.2, 56.2, 102.1, 111.6, 117.2, 122.5, 126.4, 127.67, 127.72, 130.0, 130.9, 132.2, 141.6, 151.3, 156.3, 157.3, 160.1, 166.4

2b): 4-(2-(3-Chloro-4-methoxyphenyl)-4-methyl-7H-pyrrolo[2,3-d]pyrimidin-7-yl)benzoic acid To a suspension of methyl 4-(2-(3-chloro-4-methoxyphenyl)-4-methyl-7H-pyrrolo[2,3-d]pyrimidin-7-yl)benzoate (140 mg, 0.34 mmol) in methanol (3 ml) and 1,4-dioxane (3 ml) was added 1N NaOH (0.70 ml, 0.70 mmol) and the reaction mixture was stirred for 15 min at 80° C. The solution was filtered and the filtrate was neutralized by addition of 1N HCl (0.70 ml, 0.70 mmol). The precipitate was filtered and washed with water (3×2 ml) and methanol (2×0.5 ml). The obtained colorless crystals were dried under vacuo to give 4-(2-(3-chloro-4-methoxyphenyl)-4-methyl-7H-pyrrolo[2,3-d]pyrimidin-7-yl)benzoic acid (120 mg; 89%). M.p. 265° C.

$^{13}$C-NMR (101 MHz, DMSO-d$_6$, δ ppm): 21.4, 56.2, 102.2, 112.6, 117.0, 121.1, 122.4, 127.6, 127.9, 128.2, 128.7, 130.5, 131.4, 140.8, 150.5, 155.7, 155.8, 159.9, 166.7

Synthesis Example No. 3 preparation of 4-(2-(3,4-Difluorophenyl)-4-methyl-7H-pyrrolo[2,3-d]pyrimidin-7-yl)benzoic acid (compound No. 26)

3a): Methyl 4-(2-(3,4-difluorophenyl)-4-methyl-7H-pyrrolo[2,3-d]pyrimidin-7-yl)benzoate Under an argon atmosphere 3,4-difluorophenylboronic acid (103 mg, 0.65 mmol) and [1,1'-bis(diphenylphosphino)ferrocen]dichloropalladium(II) complex with dichloromethane (45 mg, 0.06 mmol, 1:1) were added to a suspension of methyl 4-(2-chloro-4-methyl-7H-pyrrolo[2,3-d]pyrimidin-7-yl)benzoate (150 mg, 0.50 mmol) and Cs$_2$CO$_3$ (492 mg, 1.51 mmol) in dry 1,4-dioxane (1.6 ml). The reaction mixture was heated up to 100° C. for 3 h. The crude product was purified by flash chromatography to give methyl 4-(2-(3-chloro-4-methoxyphenyl)-4-methyl-7H-pyrrolo[2,3-d]pyrimidin-7-yl)benzoate (85 mg, 45%) as a colorless solid.

LC-MS (method 1): m/z: [M+H]$^+$=380.2, R$_t$=4.4 min $^{13}$C-NMR (101 MHz, CDCl$_3$, δ ppm): 21.8, 52.3, 102.1, 117.0, 117.1, 117.2, 117.6, 122.7, 124.2, 124.3, 124.3, 124.3, 127.0, 128.0, 131.0, 135.8, 135.9, 141.5, 149.2, 149.3, 150.4, 150.5, 151.2, 151.6, 151.7, 152.9, 153.0, 156.6, 160.3, 166.4

3b): 4-(2-(3,4-Difluorophenyl)-4-methyl-7H-pyrrolo[2,3-d]pyrimidin-7-yl)benzoic acid To a suspension of methyl 4-(2-(3-chloro-4-methoxyphenyl)-4-methyl-7H-pyrrolo[2,3-d]pyrimidin-7-yl)benzoate (85 mg, 0.22 mmol) in methanol (2 ml) and 1,4-dioxane (4 ml) was added 1N NaOH (0.44 ml, 0.44 mmol) and the reaction mixture was stirred for 15 min at 80° C. The solution was filtered and the filtrate was neutralized by addition of 1N HCl (0.44 ml, 0.44 mmol). The precipitate was filtered and washed with water (3×5 ml) and methanol (3×2 ml). The obtained colorless crystals were dried under vacuo to give of 4-(2-(3,4-difluorophenyl)-4-methyl-7H-pyrrolo[2,3-d]pyrimidin-7-yl)benzoic acid (72 mg, 90%).

$^{13}$C-NMR (101 MHz, DMSO-d$_6$, δ ppm): 21.4, 102.2, 116.0, 116.2, 117.4, 117.7, 122.4, 124.4, 128.3, 128.3, 128.5, 130.4, 130.5, 135.6, 135.6, 135.7, 140.7, 148.2, 148.3, 149.3, 149.4, 150.3, 150.6, 150.8, 151.8, 151.9, 154.9, 154.9, 160.0, 166.6

Synthesis Example No. 4 preparation of: 2-(3-(4-Ethyl-2-(3-fluoro-4-methoxyphenyl)-5H-pyrrolo[2,3-d]pyrimidin-7(6H)-yl)phenoxy)-N,N-dimethylacetamide (compound No. 9)

4a): (3-Iodo-phenoxy)-acetic acid ethyl ester

To a solution of 3-iodophenol (2.00 g, 9 mmol) in acetone (20 ml) was added anhydrous K$_2$CO$_3$ (1.88 g, 13.6 mmol) and the reaction mixture was stirred at RT for 10 min. Then ethyl bromoacetate (1.5 ml, 13.5 mmol) was added and the reaction mixture was heated up to 50-60° C. for 12 h under nitrogen atmosphere. The reaction mixture was poured into water and the crude product was extracted with ethyl acetate (1×100 ml). The organic layer was washed with 5% aqueous NaOH solution (20 ml) and water (50 ml). The ethyl acetate layer was washed with brine (50 ml), dried over anhydrous Na$_2$SO$_4$, filtered and the solvent was removed under reduced pressure to give (3-iodo-phenoxy)-acetic acid ethyl ester (2.60 g, 94%) as a yellow solid.

4b): (3-Iodo-phenoxy)-acetic acid

To a stirred solution of (3-iodo-phenoxy)-acetic acid ethyl ester (2.00 g, 6.5 mmol) in THF:MeOH:H$_2$O (2:1:1, 100 ml) was added LiOH.H$_2$O (0.54 g, 12.8 mmol). The resulting reaction mixture was stirred for 10 h at room temperature. The reaction mixture was concentrated under vacuum, diluted with water (50 ml), acidified with 2N HCl and the crude product was extracted with ethyl acetate (2×100 ml). The organic layer was washed with brine (50 ml), dried over anhydrous Na$_2$SO$_4$, filtered and concentrated under reduced pressure to afford (3-Iodo-phenoxy)-acetic acid (1.50 g, 83%) as an off-white solid.

4c): 2-(3-Iodo-phenoxy)-N,N-dimethyl-acetamide

At 0° C. oxalyl chloride (1.39 ml, 15.8 mmol) was added dropwise to a stirred solution of (3-iodo-phenoxy)-acetic acid (1.50 g, 5.3 mmol) and catalytic amounts of DMF (2-3 drops) in dichloromethane (10 ml). The reaction mixture was stirred for 1 h at RT. The solvent was removed under reduced pressure and the resulting residue was dissolved in a mixture of dichloromethane (10 ml) and triethylamine (4.51 ml, 32 mmol). The reaction mixture was stirred for 10 min at room temperature under nitrogen atmosphere. 2M dimethylamine solution (8.09 ml, 15.9 mmol) was added dropwise and the reaction mixture was stirred for further 12 h at RT. The reaction was stopped by addition of water (50 ml) and the crude product was extracted with dichloromethane (2×50 ml). The combined organic layers were washed with saturated aqueous NH$_4$Cl solution (20 ml) and saturated aqueous NaHCO$_3$ solution (20 ml). Organic layers were combined, washed with brine (50 ml), dried over anhydrous Na$_2$SO$_4$, filtered and the solvent was removed under reduced pressure. The crude product was purified by column chromatography to afford pure 2-(3-iodo-phenoxy)-N,N-dimethyl-acetamide (600 mg, 37%) as a brown oil. R$_f$=0.3 (ethyl acetate/hexane 50/50)

4d): 3-Fluoro-4-methoxy-benzamidine

A solution of 1M LiHMDS in THF (132 ml, 0.132 mmol) was added to diethyl ether (100 ml) at 0° C. and stirred for 30 min. Then a solution of 3-fluoro-4-methoxy benzonitrile (10 g, 66.22 mmol) in THF (50 ml) was added and the reaction mixture was stirred for 16 h at 0° C. The reaction mixture was acidified with 5N aqueous. HCl at 0° C. and the aqueous layer was washed with ethyl acetate (2×200 ml). The aqueous layer was basified with 20% (w/v) aqueous NaOH solution up to pH 10. The product was extracted with dichloromethane 3×200 ml) and the combined organic layers were washed with brine, dried over anhydrous $Na_2SO_4$, filtered and concentrated under reduced pressure to afford pure 3-fluoro-4-methoxy-benzamidine (10 g, 90%) as a brown solid. $R_f$=0.1 (methanol/dichloromethane 10/90)

4e): 2-Ethoxy-4,5-dihydro-3H-pyrrole-3-carboxylic acid ethyl ester

Epichlorohydrin (20 ml) was added dropwise to a stirred solution of borontrifluoride-diethyletherate (30 ml) in 50 ml diethylether while maintaining the internal temperature below 40° C. After addition the reaction mixture was stirred for 3 h under reflux. The solution was cooled down to RT and a white precipitate was formed. The supernatant was syringed out and the remaining residue was washed with dry ether. The obtained product was dried under reduced pressure to give 26.6 g of $BF_4OEt_3$ which was used in the next step without further purification. $BF_4OEt_3$ (26.6 g, 0.1410 mol) in dichloromethane (100 ml) was slowly added to a solution of 2-oxo-pyrrolidine-3-carboxylic acid ethyl ester (11.08 g, 0.0705 mol) in dichloromethane (50 ml) and the mixture was stirred for 16 h at RT. The reaction mixture was cooled to 0° C. and saturated aqueous $K_2CO_3$ solution (30 ml) was added. The crude product was extracted with dichloromethane (200 ml) and the organic layer was dried over anhydrous $Na_2SO_4$, filtered and concentrated under reduced pressure. The residue was purified by column chromatography to afford 2-ethoxy-4,5-dihydro-3H-pyrrole-3-carboxylic acid ethyl ester (10 g, 76%) as a colorless liquid.

$R_f$=0.4 (ethyl acetate/hexane 50/50)

4f): 2-(3-Fluoro-4-methoxy-phenyl)-6,7-dihydro-5H-pyrrolo[2,3-d]pyrimidin-4-ol To a solution of 3-fluoro-4-methoxy-benzamidine (6 g, 35.7 mmol) in toluene (150 ml), 2-ethoxy-4,5-dihydro-3H-pyrrole-3-carboxylic acid ethyl ester (9.9 g, 53.5 mmol) was added at RT and the mixture was heated to 100° C. for 16 h. Reaction mixture was cooled to RT and the resulting precipitate was filtered off, washed with ethyl acetate (2×50 ml) and dried under reduced pressure to afford the desired 2-(3-fluoro-4-methoxy-phenyl)-6,7-dihydro-5H-pyrrolo[2,3-d]pyrimidin-4-ol (10% methanol/dichloro-methane (5 g, 53.64%) as a brown solid. $R_f$=0.4 (methanol/dichloromethane 10/90)

4g): Trifluoromethanesulfonic acid 2-(3-fluoro-4-methoxy-phenyl)-6,7-dihydro-5H-pyrrolo[2,3-d]pyrimidin-4-yl ester To a suspension of 2-(3-fluoro-4-methoxy-phenyl)-6,7-dihydro-5H-pyrrolo[2,3-d]pyrimidin-4-ol (4 g, 15.3 mmol) in dichloromethane (40 ml), triethylamine (3.2 ml, 22 mmol) was added at 0° C. followed by dropwise addition of trifluoromethanesulfonic anhydride (3 ml, 16.8 mmol) over a period of 10 min. The mixture was allowed to warm up to RT and stirred for another 30 min. The reaction mixture was diluted with dichloromethane (100 ml) and washed with saturated aqueous $NaHCO_3$ solution (2×30 ml). The organic layer was separated, dried over anhydrous $Na_2SO_4$, filtered and concentrated under reduced pressure to give the crude product which was then purified by flash chromatography to afford trifluoromethanesulfonic acid 2-(3-fluoro-4-methoxy-phenyl)-6,7-dihydro-5H-pyrrolo[2,3-d]pyrimidin-4-yl ester (3.75 g, 62.5%) as a white solid. $R_f$=0.6 (methanol/dichloromethane 10/90)

4h): 2-(3-Fluoro-4-methoxy-phenyl)-4-trifluoromethanesulfonyloxy-5,6-dihydro-pyrrolo[2,3-d]pyrimidine-7-carboxylic acid tert-butyl ester DMAP (0,310 g, 2.5 mmol) was added to a stirred solution of trifluoromethanesulfonic acid 2-(3-fluoro-4-methoxy-phenyl)-6,7-dihydro-5H-pyrrolo[2,3-d]pyrimidin-4-yl ester (5 g, 12.7 mmol) in dichloro-methane (50 ml) followed by addition of Boc-anhydride (3.8 ml, 19.05 mmol) and DIPEA (2.3 ml, 14.4 mmol) at RT and stirred for another 2 h. Reaction mixture was concentrated under reduced pressure to get crude product which was then purified by flash chromatography to afford 2-(3-fluoro-4-methoxy-phenyl)-4-trifluoromethanesulfonyloxy-5,6-dihydro-pyrrolo[2,3-d]pyrimidine-7-carboxylic acid tert-butyl ester (4 g, 67%) as a white solid. $R_f$=0.6 (ethyl acetate/hexane 30/70)

4i): 4-Ethyl-2-(3-fluoro-4-methoxy-phenyl)-5,6-dihydro-pyrrolo[2,3-d]pyrimidine-7-carboxylic acid tert-butyl ester Under an argon atmosphere $PdCl_2$(dppf) (0.997 g, 1.22 mmol) was added to a stirring solution of 2-(3-fluoro-4-methoxy-phenyl)-4-trifluoromethanesulfonyloxy-5,6-dihydro-pyrrolo[2,3-d]pyrimidine-7-carboxylic acid tert-butyl ester (3.0 g, 6.1 mmol) in dry 1,4-dioxane (12 ml). 1M Diethylzinc solution in hexane (6.72 ml, 6.72 mmol) was added dropwise over a period of 10 min and stirred for further 5 min at RT. The reaction mixture was filtered over Celite® and the filtrate was diluted with ethyl acetate (300 ml). The organic layer was washed with water (2×100 ml) and then with brine (100 ml). The organic layer was dried over anhydrous $Na_2SO_4$, filtered and concentrated under reduced pressure. The residue was then purified by column chromatography to afford 4-ethyl-2-(3-fluoro-4-methoxy-phenyl)-5,6-dihydro-pyrrolo[2,3-d]pyrimidine-7-carboxylic acid tert-butyl ester (1.9 g, 73%) as an off white solid. $R_f$=0.5 (ethyl acetate/dichloromethane 30/70)

4j) 4-Ethyl-2-(3-fluoro-4-methoxy-phenyl)-6,7-dihydro-5H-pyrrolo[2,3-d]pyrimidine To a solution of 4-ethyl-2-(3-fluoro-4-methoxy-phenyl)-5,6-dihydro-pyrrolo[2,3-d]pyrimidine-7-carboxylic acid tert-butyl ester (4 g, 10.7 mmol) in dichloromethane (135 ml) was added trifluoroacetic acid (27 ml) at 0° C. and then stirred at RT for 2 h. The reaction mixture was concentrated under reduced pressure. The residue was diluted with dichloromethane (150 ml) and Amberlyst-A-21 (10 g) was added and the reaction mixture was stirred for 2 h at RT. The reaction mixture was filtered through sintered and the filtrate was concentrated and dried under reduce pressure to give the desired 4-ethyl-2-(3-fluoro-4-methoxy-phenyl)-6,7-dihydro-5H-pyrrolo[2,3-d]pyrimidine (2.9 g, 100%) as a brown solid. $R_f$=0.4 (methanol/dichloromethane 5/95)

4k): 2-{3-[4-Ethyl-2-(3-fluoro-4-methoxy-phenyl)-5,6-dihydro-pyrrolo[2,3-d]pyrimidin-7-yl]-phenoxy}-N,N-dimethyl-acetamide To a stirring solution of 4-ethyl-2-(3-fluoro-4-methoxy-phenyl)-6,7-dihydro-5H-pyrrolo[2,3-d]pyrimidine (0.1 g, 0.36 mmol) in toluene (5 ml) was added $K_3PO_4$ (0.155 g, 0.73 mmol), 2-(3-iodo-phenoxy)-N,N-dimethyl-acetamide (0.167 g, 0.54 mmol) and trans-N,N'-dimethylcyclohexane-1,2-diamine (0.021 g, 0.146 mmol). The resulting reaction mixture was degassed with argon for a period of 10 min. and then CuI (0.014 g, 0.073 mmol) was added. The reaction mixture was heated to 100° C. for 3 h. The reaction mixture was allowed to cool to RT and filtered over Celite®. The filtrate was diluted with ethyl acetate (50 ml), the organic layer was washed with water (2×10 ml) and then with brine (10 ml). The organic layer was dried over anhydrous $Na_2SO_4$, filtered and concentrated under reduced pressure to give crude product which was purified by column chromatography to afford 2-{3-[4-ethyl-2-(3-fluoro-4-methoxy-phenyl)-5,6-dihydro-pyrrolo[2,3-d]pyrimidin-7-yl]-phenoxy}-N,N-dimethyl-acetamide (0.1 g, 61%) as a white solid.

1H-NMR (400 MHz; DMSO-$d_6$, δ ppm): 1.24-1.27 (3H), 2.60-2.65 (2H), 2.84 (3H), 3.01 (3H), 3.12-3.17 (2H), 3.91 (3H), 4.10-4.15 (2H), 6.63-6.66 (1H), 7.26-7.35 (2H), 7.51-7.60 (1H), 7.60 (1H), 8.05-8.09 (1H), 8.16-8.19 (1H).

Synthesis Example No. 5 preparation of: 2,2,2-Trifluoroacetic acid compound with 2-(4-(4-ethyl-2-(3-fluoro-4-methoxyphenyl)-7H-pyrrolo[2,3-d]pyrimidin-7-yl)phenyl)acetic acid (1:1) (compound No. 4)

5a): 2,4-Dichloro-pyrrolo[2,3-d]pyrimidine-7-carboxylic acid tert-butyl ester DMAP (0.026 g, 0.21 mmol), Boc-anhydride (3.5 ml, 1.6 mmol) and DIPEA (0.22 ml, 1.28 mmol) were subsequently added to a stirred solution of 2,4-dichloro-7H-pyrrolo[2,3-d]pyrimidine (0.2 g, 1.06 mmol) in dichloromethane (5 ml) and the mixture was stirred for 2 h at RT. The solvent was removed under reduced pressure to give crude product which was purified by flash chromatography to afford tert-butyl 2,4-dichloro-7H-pyrrolo[2,3-d]pyrimidine-7-carboxylate (0.21 g, 68.6%) as a white solid). $R_f$=0.7 (ethyl acetate/hexane 20/80)

5b): 2-Chloro-4-ethyl-pyrrolo[2,3-d]pyrimidine-7-carboxylic acid tert-butyl ester Under an argon atmosphere $PdCl_2$(dppf) (0.568 g, 0.696 mmol) was added to a stirring solution of tert-butyl 2,4-dichloro-7H-pyrrolo[2,3-d]pyrimidine-7-carboxylate (1.0 g, 3.48 mmol) in dry 1,4-dioxane (7 ml). 1M Diethylzinc solution in hexane (3.48 ml, 3.48 mmol) was added dropwise over a period of 10 min at RT. The reaction was stopped by addition of ice water. The reaction mixture was filtered over Celite® and the filtrate was diluted with ethyl acetate (150 ml). The organic layer was washed with water (2×50 ml) and with brine (50 ml). The organic layer was dried over anhydrous $Na_2SO_4$, filtered and concentrated under reduced pressure to give crude product which was purified by column chromatography to afford 2-chloro-4-ethyl-pyrrolo[2,3-d]pyrimidine-7-carboxylic acid tert-butyl ester (0.2 g, 20%) as off white solid. $R_f$=0.5 (ethyl acetate/dichloromethane 2/98)

5c): 4-Ethyl-2-(3-fluoro-4-methoxy-phenyl)-pyrrolo[2,3-d]pyrimidine-7-carboxylic acid tert-butyl ester To a stirring solution of 2-chloro-4-ethyl-pyrrolo[2,3-d]pyrimidine-7-carboxylic acid tert-butyl ester (7.0 g, 24.91 mmol) and 3-fluoro-4-methoxy-phenyl boronic acid (6.35 g, 37.36 mmol) in a 1:1 mixture of THF and water (150 ml) under argon atmosphere was added $K_2CO_3$ (6.87 g, 49.82 mmol) and $PdCl_2(PPh_3)_2$ (3.49 g, 4.98 mmol). The resulting reaction mixture was stirred for 16 h at 90° C. The reaction mixture was filtered over Celite®, the filtrate was diluted with ethyl acetate (500 ml), the organic layer was washed with water (2×150 ml) and then with brine (150 ml). The separated organic layer was dried over anhydrous $Na_2SO_4$, filtered and concentrated under reduced pressure to give crude product which was purified by column chromatography to afford 4-ethyl-2-(3-fluoro-4-methoxy-phenyl)-pyrrolo[2,3-d]pyrimidine-7-carboxylic acid tert-butyl ester (6.0 g, 65.2%) as an off white solid. $R_f$=0.5 (ethyl acetate/dichloromethane 2/98)

5d): 4-Ethyl-2-(3-fluoro-4-methoxy-phenyl)-7H-pyrrolo[2,3-d]pyrimidine

To a solution of 4-ethyl-2-(3-fluoro-4-methoxy-phenyl)-pyrrolo[2,3-d]pyrimidine-7-carboxylic acid tert-butyl ester (5.0 g, 13.47 mmol) in dichloromethane (135 ml) was added trifluoroacetic acid (27 ml) at 0° C. and the mixture was stirred at RT for 2 h. The solvents were removed under reduced pressure. Then the concentrated residue was diluted with dichloromethane (150 ml) and Amberlyst-A-21 (10 g) was added and the reaction mixture was stirred for further 2 h at RT. The reaction mixture was filtered through sintered and the filtrate was concentrated and dried under reduce pressure to give the desired 4-ethyl-2-(3-fluoro-4-methoxy-phenyl)-7H-pyrrolo[2,3-d]pyrimidine (3.5 g, 95.8%%) as an off white solid.

5e): tert-Butyl 2-(4-(4-ethyl-2-(3-fluoro-4-methoxy-phenyl)-7H-pyrrolo[2,3-d]pyrimidin-7-yl)phenyl)-acetate To a stirring solution of 4-ethyl-2-(3-fluoro-4-methoxy-phenyl)-7H-pyrrolo[2,3-d]pyrimidine (0.2 g, 0.738 mmol) in toluene (10 ml) was added $K_3PO_4$ (0.312 g, 1.47 mmol), 4-iodo-phenyl)-acetic acid tert-butyl ester (0.352 g, 1.1 mmol) and trans-N,N'-dimethylcyclohexane-1,2-diamine (0.042 g, 0.295 mmol). The resulting reaction mixture was degassed with argon for a period of 10 min. CuI (0.028 g, 0.147 mmol) was added and the reaction mixture was heated for 30 min at 90° C. At completion, the reaction mixture was allowed to come to room temperature and filtered over Celite®, the filtrate was diluted with ethyl acetate (50 ml), the organic layer was washed with water (2×10 ml) and then with brine (10 ml). The organic layer was dried over anhydrous $Na_2SO_4$, filtered and concentrated under reduced pressure to give crude product which was purified by column chromatography to afford {4-[4-ethyl-2-(3-fluoro-4-methoxy-phenyl)-5,6-dihydro-pyrrolo[2,3-d]pyrimidin-7-yl]-phenyl}-acetic acid tert-butyl ester (0.25 g, 73.5%) as a white solid.

1H-NMR (400 MHz; DMSO-$d_6$, δ ppm): 1.39-1.44 (12H), 3.07-3.14 (2H, 3.68 (2H), 3.90 (2H), 6.94-6.96 (1H), 7.27-7.32 (1H), 7.48-7.51 (2H), 7.89-7.91 (2H), 7.95-7.97 (1H), 8.13-8.17 (1H), 8.24-8.27 (1H).

5f) 2,2,2-Trifluoroacetic acid compound with 2-(4-(4-ethyl-2-(3-fluoro-4-methoxyphenyl)-7H-pyrrolo[2,3-d]pyrimidin-7-yl)phenyl)acetic acid (1:1)

To a solution of {4-[4-ethyl-2-(3-fluoro-4-methoxy-phenyl)-5,6-dihydro-pyrrolo[2,3-d]pyrimidin-7-yl]-phenyl}-acetic acid tert-butyl ester (0.25 g, 0.539 mmol) in dichloromethane (10 ml) was added trifluoroacetic acid (0.615 g, 5.39 mmol) at 0° C. and the reaction mixture was stirred at RT for 16 h. The reaction mixture was concentrated under reduced pressure to give crude product which was purified by repeated washing with diethyl ether to get the pure 2,2,2-trifluoroacetic acid compound with 2-(4-(4-ethyl-2-(3-fluoro-4-methoxyphenyl)-7H-pyrrolo[2,3-d]pyrimidin-7-yl)phenyl)acetic acid (0.230 g, 82%. $R_f$=0.1, 10% methanol/dichloromethane) as sticky white solid.

1H-NMR (400 MHz; DMSO-$d_6$, δ ppm): 1.39-1.44 (3H), 3.08-3.14 (2H), 3.70 (2H), 3.91 (3H), 6.95-6.97 (1H), 7.28-7.33 (1H), 7.49-7.52 (2H), 7.88-7.91 (2H), 7.95-7.97 (1H), 8.13-8.17 (1H), 8.23-8.26 (1H), 11.80-12.83 (1H).

Synthesis Example No. 6 preparation of: 2-(4-(2-(3-Chloro-4-methoxyphenyl)-4-methyl-5H-pyrrolo[2,3-d]pyrimidin-7(6H)-yl)phenyl)acetic acid (compound No. 20)

6a): (Z)-1-(1-(2-Oxodihydrofuran-3(2H)-ylidene)ethyl)urea

Concentrated aqueous HCl (0.15 ml, 1.8 mmol) was added to a suspension of 3-acetyldihydrofuran-2-one (15.0 g, 117 mmol) and urea (15.0 g, 250 mmol) in ethanol (15 ml) and the mixture was stirred for 90 min under reflux. The suspension was cooled to RT and diluted with water (60 ml). The formed crystals were filtered and washed with water (3×10 ml) and ethanol (3×5 ml) and dried under vacuo to give (Z)-1-(1-(2-oxodihydrofuran-3(2H)-ylidene)ethyl)urea (12.80 g, 64%) as a white solid.

$^{13}$C-NMR (101 MHz, DMSO-$d_6$, δ ppm): 18.6, 25.2, 65.1, 96.6, 150.1, 154.3, 172.1

6b): 5-(2-Hydroxyethyl)-6-methylpyrimidine-2,4-diol

Sodium methylat (5.4 ml, 99.96 mmol) was added to a suspension of (Z)-1-(1-(2-oxodihydrofuran-3(2H)-ylidene)ethyl)urea (12.8 g, 75.22 mmol) in methanol (65 ml) and the mixture was stirred for 18 h under reflux. The suspension was cooled to RT and the reaction was stopped by addition of water (10 ml). The mixture was neutralized by addition of acetc acid and the formed crystals were filtered, washed with water (4×10 ml) and methanol (3×10 ml) and dried under vacuo to give 5-(2-hydroxyethyl)-6-methylpyrimidine-2,4-diol (8.08 g 63%) as a white solid.

$^{13}$C-NMR (101 MHz, DMSO-$d_6$, δ ppm): 16.2, 28.0, 59.7, 105.9, 148.8, 150.8, 164.4

6c): 2,4-Dichloro-5-(2-chloroethyl)-6-methylpyrimidine

N,N-Dimethylaniline (2.5 ml, 19.72 mmol) was added to a suspension of 5-(2-hydroxyethyl)-6-methylpyrimidine-2,4-diol (2.0 g, 11.75 mmol) in phosphoryl trichloride (20 ml, 211 mmol) and the mixture was stirred for 2 h under reflux. The brown solution was cooled to RT and then transferred to ice (300 g). After 30 min the formed precipitate was filtered, washed with water (3×10 ml) and dried to give 2,4-dichloro-5-(2-chloroethyl)-6-methylpyrimidine (71% 1.88 g) as a slight yellow solid.

$^{13}$C-NMR (101 MHz, DMSO-$d_6$, δ ppm): 22.5, 30.9, 41.6, 127.6, 156.3, 161.5, 172.1

6d): Ethyl 2-(4-(2-chloro-4-methyl-5H-pyrrolo[2,3-d]pyrimidin-7(6H)-yl)phenyl)acetate NaHCO$_3$ (2.36 g, 28.12 mmol) and NaI (1.40 g, 9.37 mmol) were added to a suspension of 2,4-dichloro-5-(2-chloroethyl)-6-methylpyrimidine (2.11 g, 9.37 mmol) and ethyl 2-(4-aminophenyl)acetate (1.68 g, 9.37 mmol) in dry DMF and the mixture was stirred for 1 h at 130° C. The reaction mixture was cooled to RT and water (30 ml) was added. The yellow precipitate was filtered, washed with water (2×5 ml) and diethylether (2×5 ml), dried to give ethyl 2-(4-(2-chloro-4-methyl-5H-pyrrolo[2,3-d]pyrimidin-7(6H)-yl)phenyl)acetate (1.37 g, 44%) as a slight yellow solid.

LC-MS (Method 1): m/z: [M+H]$^+$=332.2, R$_t$=3.7 min
$^{13}$C-NMR (101 MHz, CDCl$_3$, δ ppm): 14.2, 20.6, 22.2, 40.7, 49.3, 60.8, 117.7, 118.5, 129.2, 129.8, 138.8, 158.8, 159.1, 165.5, 171.5

6e): Ethyl 2-(4-(2-(3-chloro-4-methoxyphenyl)-4-methyl-5H-pyrrolo[2,3-d]pyrimidin-7(6H)-yl)phenyl)-acetate Under argon atmosphere [1,1'-bis(diphenylphosphino)ferrocene]dichloropalladium(II) complex with dichloromethane (84 mg, 0.10 mmol, 1:1) and Cs$_2$CO$_3$ (934 mg, 2.87 mmol) were added to a suspension of 3-chloro-4-methoxyphenylboronic acid (185 mg, 0.99 mmol) and ethyl 2-(4-(2-chloro-4-methyl-5H-pyrrolo[2,3-d]pyrimidin-7(6H)-yl)phenyl)acetate (311 mg, 0.94 mmol) in dry 1,4-dioxane (2 ml) and the mixture was stirred for 1 h at 95° C. The reaction mixture was cooled to RT and the crude product was purified by flash chromatography to give ethyl 2-(4-(2-(3-chloro-4-methoxyphenyl)-4-methyl-5H-pyrrolo[2,3-d]pyrimidin-7(6H)-yl)phenyl)acetate (225 mg, 55%) as a colorless solid.

LC-MS (Method 1): m/z: [M+H]$^+$=438.2, R$_t$=3.65 min
$^{13}$C-NMR (101 MHz, CDCl$_3$, δ ppm): 14.2, 20.9, 22.8, 40.8, 48.6, 56.2, 60.8, 111.4, 116.6, 118.0, 122.3, 127.8, 128.0, 129.6, 130.0, 131.8, 140.0, 156.5, 157.6, 161.5, 164.5, 171.7

6f): 2-(4-(2-(3-Chloro-4-methoxyphenyl)-4-methyl-5H-pyrrolo[2,3-d]pyrimidin-7(6H)-yl)phenyl)acetic acid 1M aqueous NaOH (1.16 ml, 1.16 mmol) was added to a suspension of ethyl 2-(4-(2-(3-chloro-4-methoxyphenyl)-4-methyl-5H-pyrrolo[2,3-d]pyrimidin-7(6H)-yl)phenyl)acetate (159 mg, 0.36 mmol) in MeOH (4 ml) and the mixture was stirred for 20 min at 95° C. After the reaction mixture was cooled to RT 1M aqueous HCl (1.16 mmol) was added and the clear solution was reduced to 2 ml under reduced pressure. The precipitate was filtered, washed with water (3×2 ml) and methanol (1×2 ml) and dried under vacuo to give the desired 2-(4-(2-(3-chloro-4-methoxyphenyl)-4-methyl-5H-pyrrolo[2,3-d]pyrimidin-7(6H)-yl)phenyl)acetic acid (150 mg, quantitative) as a colorless solid. M.p. 213-215° C.

$^{13}$C-NMR (101 MHz, DMSO-d$_6$, δ ppm): 20.7, 22.1, 40.0, 48.3, 56.2, 112.4, 117.4, 117.5, 120.9, 127.5, 128.5, 128.6, 129.6, 131.4, 139.4, 155.9, 157.3, 159.8, 164.0, 172.8
LC-MS (Method 1): m/z: [M+H]$^+$=410.2, R$_t$=3.3 min Synthesis Example No. 7 preparation of: 2-(4-(2-(3-Fluoro-4-methoxyphenyl)-4-methyl-5H-pyrrolo[2,3-d]pyrimidin-7(6H)-yl)phenyl)acetic acid (compound No. 7)

7a) Ethyl 2-(4-(2-(3-fluoro-4-methoxyphenyl)-4-methyl-5H-pyrrolo[2,3-d]pyrimidin-7(6H)-yl)phenyl)-acetate Under argon atmosphere [1,1'-bis(diphenylphosphino)ferrocen]dichloropalladium(II) complex with dichloromethane (81 mg, 0.10 mmol, 1:1) and Cs$_2$CO$_3$ (896 mg, 2.75 mmol) were added to a suspension of 3-fluoro-4-methoxyphenylboronic acid (177 mg, 0.95 mmol) and ethyl 2-(4-(2-chloro-4-methyl-5H-pyrrolo[2,3-d]pyrimidin-7(6H)-yl)phenyl)acetate (300 mg, 0.90 mmol) in dry 1,4-dioxane (2 ml) and the mixture was stirred for 1.5 h at 90° C. The reaction mixture was cooled to RT and the crude product was purified by flash chromatography to give ethyl 2-(4-(2-(3-fluoro-4-methoxyphenyl)-4-methyl-5H-pyrrolo[2,3-d]pyrimidin-7(6H)-yl)phenyl)acetate (252 mg, 66%) as a colorless solid.
LC-MS (Method 1): m/z: [M+H]$^+$=422.3, R$_t$=3.5 min
$^{13}$C-NMR (101 MHz, CDCl$_3$, δ ppm): 14.2, 20.8, 22.8, 40.8, 48.7, 56.2, 60.8, 112.6, 112.6, 115.7, 115.9, 116.6, 118.0, 124.4, 124.4, 128.1, 129.7, 131.4, 139.9, 149.3, 149.4, 151.0, 153.4, 157.4, 161.6, 161.6, 164.5, 171.7

7b) 2-(4-(2-(3-Fluoro-4-methoxyphenyl)-4-methyl-5H-pyrrolo[2,3-d]pyrimidin-7(6H)-yl)phenyl)acetic acid 1M aqueous NaOH (1.14 ml, 1.14 mmol) was added to a suspension of ethyl 2-(4-(2-(3-fluoro-4-methoxyphenyl)-4-methyl-5H-pyrrolo[2,3-d]pyrimidin-7(6H)-yl)phenyl)acetate (150 mg, 0.36 mmol) in MeOH (4 ml) and 1,4-dioxane (4 ml) and the mixture was stirred for 20 min at 95° C. After the reaction mixture was cooled to RT 1M aqueous HCl (1.14 mmol) was added and the clear yellow solution was reduced to 2 ml under reduced pressure. The precipitate was filtered, washed with water (3×2 ml) and dried under vacuo to give the desired 2-(4-(2-(3-fluoro-4-methoxyphenyl)-4-methyl-5H-pyrrolo[2,3-d]pyrimidin-7(6H)-yl)phenyl)acetic acid (124 mg, 87%) as a slight yellow solid. M.p. 180-183° C.
$^{13}$C-NMR (101 MHz, DMSO-d$_6$, δ ppm): 19.9, 21.9, 40.0, 48.7, 56.1, 113.4, 114.5, 114.7, 117.8, 117.9, 124.3, 129.1, 129.7, 139.0, 149.1, 149.2, 150.0, 152.4, 155.8, 159.7, 163.9, 172.8
LC-MS (Method 1): m/z: [M+H]$^+$=394.2, R$_t$=3.15 min Synthesis Example No. 8 preparation of: 2-(4-(2-(3-Chloro-4-methoxyphenyl)-4-methyl-7H-pyrrolo[2,3-d]pyrimidin-7-yl)phenyl)acetic acid (compound No. 16)

8a): Ethyl 2-(4-(2-(3-chloro-4-methoxyphenyl)-4-methyl-7H-pyrrolo[2,3-d]pyrimidin-7-yl)phenyl)-acetate Under an argon atmosphere MnO$_2$ (1.66 g, 19.07 mmol) was added to a clear solution of ethyl 2-(4-(2-(3-chloro-4-methoxyphenyl)-4-methyl-5H-pyrrolo[2,3-d]pyrimidin-7(6H)-yl)phenyl)acetate (1.67 g, 3.81 mmol) in dry toluene (12 ml) and the mixture was stirred for 8 h at 60° C. The reaction mixture was cooled to RT and the crude product was purified by flash chromatography to give ethyl 2-(4-(2-(3-chloro-4-methoxyphenyl)-4-methyl-7H-pyrrolo[2,3-d]pyrimidin-7-yl)phenyl)acetate (132 mg, 8%) as a colorless solid.
$^{13}$C-NMR (101 MHz, CDCl$_3$, δ ppm): 14.2, 21.6, 40.9, 56.2, 61.0, 101.2, 111.6, 116.9, 122.5, 123.6, 127.4, 127.8, 130.0, 130.2, 132.2, 132.6, 136.7, 151.0, 156.3, 156.9, 159.8, 171.3
LC-MS (Method 1): m/z: [M+H]$^+$=436.2, R$_t$=4.2 min 8b) 2-(4-(2-(3-Chloro-4-methoxyphenyl)-4-methyl-7H-pyrrolo[2,3-d]pyrimidin-7-yl)phenyl)acetic acid 1M aqueous NaOH (1.17 ml, 1.17 mmol) was added to a suspension of ethyl 2-(4-(2-(3-chloro-4-methoxyphenyl)-4-methyl-7H-pyrrolo[2,3-d]pyrimidin-7-yl)phenyl)acetate (159 mg, 0.37 mmol) in MeOH (5 ml) and 1,4-dioxane (5 ml) and the mixture was stirred for 20 min at 95° C. After the reaction mixture was cooled to RT 1M aqueous HCl (1.17 mmol) was added and the clear solution was reduced to 3 ml under reduced pressure. The precipitate was filtered, washed with water (3×2 ml) and methanol (2×3 ml) and dried under vacuo to give the desired 2-(4-(2-(3-chloro-4-methoxyphenyl)-4-methyl-7H-pyrrolo[2,3-d]pyrimidin-7-yl)phenyl)acetic acid (110 mg, 73%) as a colorless solid. M.p. 220-223° C.
$^{13}$C-NMR (101 MHz, DMSO-d$_6$, δ ppm): 21.4, 40.0, 56.2, 101.2, 112.6, 116.7, 121.1, 123.0, 127.5, 128.5, 128.6, 130.3, 131.6, 133.4, 135.9, 150.2, 155.5, 155.7, 159.6, 172.6
LC-MS (Method 1): m/z: [M+H]$^+$=408.2, R$_t$=3.95 min Synthesis Example No. 9 preparation of: 2-(4-(2-(3-Chloro-4-methoxyphenyl)-4-ethyl-5H-pyrrolo[2,3-d]pyrimidin-7(6H)-yl)phenyl)acetic acid (compound No. 21)

9a): 3-propionyldihydrofuran-2(3H)-one

γ-Butyrolactone (5.0 g, 58.08 mmol) in THF (50 ml) was added to a solution of 1.8M LDA (80 ml, 144 mmol) in THF/heptane/ethylbenzene. The reaction mixture was stirred for 1 h at −78° C. and then propionyl chloride (5.3 ml, 61.0 mmol) was added at −70° C. The mixture was stirred for further 15 min at −78° C. and allowed to warm up to RT. The reaction was stopped by addition of 2M aqueous HCl (200 ml) and the crude product was extracted with ethyl acetate (3×40 ml). The combined organic layers were dried over Na$_2$SO$_4$, filtrated and the solvents were removed under reduced pressure. The residue was purified by flash chromatography to give 3-propionyldihydrofuran-2(3H)-one (3.23 g, 39%) as a yellow oil.
$^{13}$C-NMR (101 MHz, CDCl$_3$, δ ppm): 7.4, 24.0, 35.6, 52.0, 67.5, 172.8, 203.0

9b): (6-Ethyl-5-(2-hydroxyethyl)pyrimidine-2,4-diol

TMSCl (20.6 mmol, 15 ml) and 3-propionyldihydrofuran-2(3H)-one (2.5 g, 17.6 mmol) were subsequently added to a suspension of urea (2 g, 33.4 mmol) in DMF (6 ml) and stirred for 24 h at RT. 2M aqueous NaOH (33.4 mmol, 16.7 ml) was added and the mixture was stirred for 15 min at 90° C. The reaction mixture was acidified by addition of concentrated aqueous HCl, saturated by addition of NaCl and the crude product was extracted with THF (3×20 ml). The combined organic layers were dried over MgSO$_4$, filtered and the solvents were removed under reduced pressure. The residue was suspended in diethyl ether. The precipitate was filtered, washed with diethyl ether (2×1 ml) and dried in vacuo to give (6-ethyl-5-(2-hydroxyethyl)pyrimidine-2,4-diol (1.2 g, 39%) as a colorless solid.

$^{13}$C-NMR (101 MHz, DMSO-d$_6$, δ ppm): 12.9, 23.0, 27.8, 59.9, 105.1, 151.1, 153.7, 145.8

9c): 2,4-Dichloro-5-(2-chloroethyl)-6-ethylpyrimidine

N,N-Dimethylaniline (11.8 mmol, 1.5 ml) was added to a suspension of (6-ethyl-5-(2-hydroxyethyl)pyrimidine-2,4-diol (1.2 g, 6.5 mmol) in phosphoryl trichloride (12 ml, 128 mmol) and the mixture was stirred for 1 h under reflux. The reaction mixture was cooled to RT and then transferred to ice (300 g). After 10 min the formed precipitate was filtered, washed with water (3×5 ml) and dried to give 2,4-dichloro-5-(2-chloroethyl)-6-ethylpyrimidine (68% 1.07 g) as a slight brown solid.

$^{13}$C-NMR (101 MHz, DMSO-d$_6$, δ ppm): 11.7, 27.5, 30.5, 41.8, 127.0, 156.7, 161.6, 175.8

9d): Ethyl 2-(4-(2-chloro-4-ethyl-5H-pyrrolo[2,3-d]pyrimidin-7(6H)-yl)phenyl)acetate NaHCO$_3$ (1.60 g, 19.05 mmol) and NaI (1.00 g, 6.67 mmol) were added to a suspension of 2,4-dichloro-5-(2-chloroethyl)-6-ethylpyrimidine (1.50 g, 6.26 mmol) and ethyl 2-(4-aminophenyl)acetate (1.10 g, 6.13 mmol) in dry DMF (5 ml) and the mixture was stirred for 40 min at 130° C. The reaction mixture was cooled to RT and water (50 ml) was added. The crude product was extracted with dichloromethane (4×20 ml). The combined organic layers were dried over Na$_2$SO$_4$, filtered and the solvent was removed under reduced pressure. The residue was purified by flash chromatography to give ethyl 2-(4-(2-chloro-4-ethyl-5H-pyrrolo[2,3-d]pyrimidin-7(6H)-yl)phenyl)acetate (1.22 g, 56%) as a white solid.

$^{13}$C-NMR (101 MHz, CDCl$_3$, δ ppm): 11.5, 14.0, 21.3, 26.8, 49.3, 60.2, 118.2, 118.4, 129.1, 129.6, 138.6, 157.5, 163.3, 165.2, 171.1

9e): Ethyl 2-(4-(2-(3-chloro-4-methoxyphenyl)-4-ethyl-5H-pyrrolo[2,3-d]pyrimidin-7(6H)-yl)phenyl)-acetate Under argon atmosphere [1,1'-bis(diphenylphosphino)ferrocen]dichloropalladium(II) complex with dichloromethane (74 mg, 0.09 mmol, 1:1) and Cs$_2$CO$_3$ (883 mg, 2.7 mmol) were added to a suspension of 3-chloro-4-methoxyphenylboronic acid (186 mg, 1.0 mmol) and ethyl 2-(4-(2-chloro-4-ethyl-5H-pyrrolo[2,3-d]pyrimidin-7(6H)-yl)phenyl)acetate (300 mg, 0.90 mmol) in dry 1,4-dioxane (2 ml) and the mixture was stirred for 1 h at 100° C. The reaction mixture was cooled to RT and the crude product was purified by flash chromatography to give ethyl 2-(4-(2-(3-chloro-4-methoxyphenyl)-4-ethyl-5H-pyrrolo[2,3-d]pyrimidin-7(6H)-yl)phenyl)acetate (261 mg, 66%) as a yellow solid.

$^{13}$C-NMR (101 MHz, CDCl$_3$, δ ppm): 12.1, 14.2, 22.6, 27.7, 40.8, 48.8, 56.2, 60.8, 111.5, 115.8, 118.1, 122.3, 127.9, 129.7, 130.1, 140.0, 156.5, 161.5, 164.7, 171.7

9f): 2-(4-(2-(3-Chloro-4-methoxyphenyl)-4-ethyl-5H-pyrrolo[2,3-d]pyrimidin-7(6H)-yl)phenyl)acetic acid 1M aqueous NaOH (0.92 ml, 0.92 mmol) was added to a suspension of ethyl 2-(4-(2-(3-chloro-4-methoxyphenyl)-4-ethyl-5H-pyrrolo[2,3-d]pyrimidin-7(6H)-yl)phenyl)acetate (244 mg, 0.54 mmol) in MeOH (4 ml) and 1,4-dioxane (4 ml) and the mixture was stirred for 0.5 h at 80° C. After the reaction mixture was cooled to RT, 1M aqueous HCl (0.92 mmol) was added. The precipitate was filtered, washed with water (3×1 ml) and diethyl ether (3×1 ml) and dried under vacuo to give the desired 2-(4-(2-(3-chloro-4-methoxyphenyl)-4-ethyl-5H-pyrrolo[2,3-d]pyrimidin-7(6H)-yl)phenyl) acetic acid (217 mg, 95%) as a slight yellow solid. M.p. 205-210° C.

$^{13}$C-NMR (101 MHz, DMSO-d$_6$, δ ppm): 11.9, 21.5, 25.7, 40.0, 49.4, 56.4, 112.7, 117.7, 118.7, 121.1, 128.4, 129.2, 129.8, 138.4, 156.8, 159.3, 164.1, 172.7

Synthesis Example No. 10 preparation of: 2-(4-(4-Ethyl-2-(3-fluoro-4-methoxyphenyl)-5H-pyrrolo[2,3-d]pyrimidin-7(6H)-yl)phenyl)-acetic acid (compound No. 8)

10a): Ethyl 2-(4-(4-ethyl-2-(3-fluoro-4-methoxyphenyl)-5H-pyrrolo[2,3-d]pyrimidin-7(6H)-yl)phenyl)-acetate Under argon atmosphere [1,1'-bis(diphenylphosphino)ferrocen]dichloropalladium(II) complex with dichloromethane 1:1 (74 mg, 0.09 mmol, 1:1) and Cs$_2$CO$_3$ (883 mg, 2.7 mmol) were added to a suspension of 3-fluoro-4-methoxyphenylboronic acid (170 mg, 1.0 mmol) and ethyl 2-(4-(2-chloro-4-ethyl-5H-pyrrolo[2,3-d]pyrimidin-7(6H)-yl)phenyl)acetate (300 mg, 0.90 mmol) in dry 1,4-dioxane (2 ml) and the mixture was stirred for 1 h at 100° C. The reaction mixture was cooled to RT and the crude product was purified by flash chromatography to give ethyl 2-(4-(2-ethyl-2-(3-fluoro-4-methoxyphenyl)-5H-pyrrolo[2,3-d]pyrimidin-7(6H)-yl)phenyl)acetate (265 mg, 70%) as a yellow solid.

$^{13}$C-NMR (101 MHz, CDCl$_3$, δ ppm): 12.0, 14.2, 22.6, 26.9, 27.7, 40.8, 48.8, 56.2, 60.8, 112.6, 112.7, 115.7, 115.8, 115.9, 118.0, 124.4, 128.0, 129.7 140.0, 149.3, 149.4, 151.0, 153.4, 161.7, 162.2, 164.7, 171.8

10b): 2-(4-(4-Ethyl-2-(3-fluoro-4-methoxyphenyl)-5H-pyrrolo[2,3-d]pyrimidin-7(6H)-yl)phenyl)acetic acid 1M aqueous NaOH (0.68 ml, 0.68 mmol) was added to a suspension of ethyl 2-(4-(4-ethyl-2-(3-fluoro-4-methoxyphenyl)-5H-pyrrolo[2,3-d]pyrimidin-7(6H)-yl)phenyl)acetate (247 mg, 0.57 mmol) in MeOH (4 ml) and 1,4-dioxane (4 ml) and the mixture was stirred for 0.5 h at 80° C. After the reaction mixture was cooled to RT, 1M aqueous HCl (0.68 mmol) was added. The precipitate was filtered, washed with water (3×1 ml) and diethyl ether (3×1 ml) and dried under vacuo to give the desired 2-(4-(4-ethyl-2-(3-fluoro-4-methoxyphenyl)-5H-pyrrolo[2,3-d]pyrimidin-7(6H)-yl) phenyl)acetic acid (214 mg, 93%) as a slight yellow solid. M.p. 190-196° C.

$^{13}$C-NMR (101 MHz, DMSO-d$_6$, δ ppm): 11.9, 21.3, 24.7, 40.0, 50.1, 56.3, 113.7, 115.6, 118.2, 119.3, 125.6, 129.9, 137.8, 149.8, 152.3, 159.1, 164.0, 172.6

Synthesis Example No. 11 preparation of: 4-(2-(5-Chlorothiophen-2-yl)-4-methyl-7H-pyrrolo[2,3-d]pyrimidin-7-yl)benzoic acid (compound No. 38)

11a): Methyl 4-(2-(5-chlorothiophen-2-yl)-4-methyl-7H-pyrrolo[2,3-d]pyrimidin-7-yl)benzoate Under argon atmosphere [1,1'-bis(diphenylphosphino)ferrocen]dichloropalladium(II) complex with dichloromethane 1:1 (18 mg, 0.025 mmol) was added to a suspension of ethyl 4-(2-chloro-4-methyl-7H-pyrrolo[2,3-d]pyrimidin-7-yl)benzoate (228 mg, 0.75 mmol) and tributyl(5-chlorothiophen-2-yl)stannane (205 mg, 0.50 mmol) in dry DMF (2 ml) and the mixture was stirred for 2 h at 150° C. The reaction was quenched by addition of water (30 ml) and the crude product was extracted with dichloromethane (3×10 ml). The combined organic layers were dried over $MgSO_4$, filtered and the solvent was reduced under reduced pressure. The residue was purified by flash chromatography to give methyl 4-(2-(5-chlorothiophen-2-yl)-4-methyl-7H-pyrrolo[2,3-d]pyrimidin-7-yl)benzoate (50 mg, 26%) as a yellow solid.

11b): 4-(2-(5-Chlorothiophen-2-yl)-4-methyl-7H-pyrrolo[2,3-d]pyrimidin-7-yl)benzoic acid To a suspension of methyl 4-(2-(5-chlorothiophen-2-yl)-4-methyl-7H-pyrrolo[2,3-d]pyrimidin-7-yl)benzoate (50 mg, 0.13 mmol) in methanol (1 ml) and 1,4-dioxane (1 ml) was added 1M NaOH (0.26 ml, 0.26 mmol) and the reaction mixture was stirred for 15 min at 80° C. The solution was filtered and the filtrate was neutralized by addition of 1M HCl (0.26 ml, 0.26 mmol). The precipitate was filtered and washed with water (3×5 ml) and methanol (3×2 ml). The obtained colorless crystals were dried under vacuo to give 4-(2-(5-chlorothiophen-2-yl)-4-methyl-7H-pyrrolo[2,3-d]pyrimidin-7-yl)benzoic acid (34 mg, 71%) as a slight yellow solid.

$^{13}$C-NMR (101 MHz, DMSO-$d_6$, δ ppm): 21.2, 102.6, 117.3, 122.3, 126.9, 128.2, 128.2, 128.3, 130.5, 130.9, 140.7, 142.6, 149.9, 153.1, 160.2, 166.6

Synthesis Example No. 12 preparation of: 2,2,2-Trifluoroacetic acid compound with 2-(4-(2-(5-chlorothiophen-2-yl)-4-methyl-5H-pyrrolo[2,3-d]pyrimidin-7(6H)-yl)phenyl)acetic acid (1:1) (compound No. 39)

12a): Ethyl 5-chlorothiophene-2-carboxylate $H_2SO_4$ (15 ml) was added at RT to a stirred solution of 5-chloro-thiophene-2-carboxylic acid (15 g, 0.0925 mol) in ethanol (300 ml). Then the reaction mixture was stirred at 80° C. for 16 h. The reaction mixture was concentrated under reduced pressure and concentrated mass was diluted with ethyl acetate (300 ml). The organic mixture was washed with water (3×100 ml), $NaHCO_3$ solution (3×100 ml) and brine (100 ml). Organic layer was dried over $Na_2SO_4$ and concentrated under reduced pressure to give ethyl 5-chlorothiophene-2-carboxylate (14 g, 80%) as colorless liquid.

12b): 5-Chlorothiophene-2-carboximidamide

To a solution of $NH_4Cl$ (14.2 g, 0.263 mol) in toluene (150 ml) was added trimethylaluminium (130 ml, 0.263 mol) at 0° C. for 1 h. Then solution of ethyl 5-chlorothiophene-2-carboxylate (10 g, 0.0526 mol) in toluene (50 ml) was added slowly at 0° C. The reaction mixture was stirred at 80° C. for 16 h. The reaction mixture was cooled to 0° C., quenched by dropwise addition of MeOH and filtered through Celite®. The filtrate was concentrated to dryness under reduced pressure and the residue was diluted with water (150 ml), acidified with 5N aqueous HCl to pH 2 and washed with ethyl acetate (2×200 ml). The aqueous layer was separated and basified with 20% (w/v) aqueous NaOH solution up to pH 10. The crude product was extracted with dichloromethane (3×200 ml) and the combined organic layer was washed with brine solution, dried over anhydrous $Na_2SO_4$, concentrated under reduced pressure to afford 5-chlorothiophene-2-carboximidamide (7.8 g, 92%) as white solid.

12c): 2-(5-Chlorothiophen-2-yl)-6,7-dihydro-5H-cyclopenta[d]pyrimidin-4-ol

2-Ethoxy-4,5-dihydro-3H-pyrrole-3-carboxylic acid ethyl ester (6 g, 0.0324 mol) was added to a solution of 5-chlorothiophene-2-carboximidamide (3.5 g, 0.022 mmol) in toluene (100 ml) and the mixture was stirred for 16 h at 100° C. The reaction mixture was cooled to RT and the precipitate was filtered, washed with ethyl acetate (2×50 ml) and dried under vacuo to give 2-(5-chlorothiophen-2-yl)-6,7-dihydro-5H-cyclopenta[d]pyrimidin-4-ol (2.9 g, 52%) as a solid.

12d): 2-(5-Chlorothiophen-2-yl)-6,7-dihydro-5H-cyclopenta[d]pyrimidin-4-yl trifluoromethanesulfonate At 0° C. trifluormethanesulfonic anhydride (3 ml, 0.017 mmol) was added dropwise over a period of 10 min to a suspension of 2-(5-chlorothiophen-2-yl)-6,7-dihydro-5H-cyclopenta[d]pyrimidin-4-ol (2.9 g, 0.0115 mol) and triethylamine (2.4 ml, 0.017 mol) in dichloromethane (50 ml). The mixture was allowed to warm to RT and stirred for 2 h. The reaction mixture was diluted with dichloromethane (100 ml) and washed with saturated aqueous $Na_2CO_3$ solution (3×30 ml). The organic layer was dried over $Na_2SO_4$, filtered and the solvent was removed under reduced pressure to give 2-(5-chlorothiophen-2-yl)-6,7-dihydro-5H-cyclopenta[d]pyrimidin-4-yl trifluoromethanesulfonate (3.4 g, 0.009 mol).

12e): 2-(5-Chlorothiophen-2-yl)-4-methyl-6,7-dihydro-5H-pyrrolo[2,3-d]pyrimidine Under an argon atmosphere trimethylboroxine (2.64 ml, 18.9 mmol) and $K_2CO_3$ (1.56 g, 11.0 mmol) were added to a solution of 2-(5-chlorothiophen-2-yl)-6,7-dihydro-5H-cyclopenta[d]pyrimidin-4-yl trifluoromethanesulfonate (2.9 g, 7.5 mmol) in 1,4-dioxane (50 ml). The reaction mixture was bubbled with argon for 10 min. $Pd(PPh_3)_4$ (0.78 g, 0.7 mmol) was added and the mixture was stirred for 3 h under reflux. The reaction mixture was cooled to RT, diluted with dichloromethane (2×50 ml) and filtered through Celite®. The solvent was removed under reduced pressure and the crude product was purified by flash chromatography to afford 2-(5-chlorothiophen-2-yl)-4-methyl-6,7-dihydro-5H-pyrrolo[2,3-d]pyrimidine (1.4 g, 5.5 mmol).

12f): 2,2,2-Trifluoroacetic acid compound with 2-(4-(2-(5-chlorothiophen-2-yl)-4-methyl-5H-pyrrolo[2,3-d]pyrimidin-7(6H)-yl)phenyl)acetic acid (1:1)

To a stirring solution of 2-(5-chlorothiophen-2-yl)-4-methyl-6,7-dihydro-5H-pyrrolo[2,3-d]pyrimidine (1 eq.) in toluene (1.5 ml) was added NaO'Bu (1.6 eq.), tert-butyl 2-(4-bromophenyl)acetate (1.5 eq.) and BINAP (0.04 eq.). The resulting reaction mixture was degassed with argon for a period of 10 min. and Pd$_2$dba$_3$ (0.02 eq.) was added and the mixture was degassed again. The reaction mixture was heated at 100° C. for 16 h. At completion, the reaction mixture was concentrated and poured in DMF (2 ml). The inorganics were filtered and the residue was purified by prep-HPLC using aqueous ammonia method to give tert-butyl 2-(4-(2-(5-chlorothiophen-2-yl)-4-methyl-5H-pyrrolo[2,3-d]pyrimidin-7(6H)-yl)phenyl)acetate which was directly used for the next step. TFA (~12 eq.) was added to a solution of tert-butyl 2-(4-(2-(5-chlorothiophen-2-yl)-4-methyl-5H-pyrrolo[2,3-d]pyrimidin-7(6H)-yl)phenyl)acetate in CH$_2$Cl$_2$ at 0° C. and the mixture was stirred at RT for 16 h. At completion the volatiles were evaporated under reduced pressure and the residue was dried completely in vacuo over a period of 14 h to get desired 2,2,2-trifluoroacetic acid compound with 2-(4-(2-(5-chlorothiophen-2-yl)-4-methyl-5H-pyrrolo[2,3-d]pyrimidin-7(6H)-yl)phenyl)acetic acid (1:1) as a solid.

1H-NMR (600 MHz; DMSO-d$_6$, δ ppm): 2.28 (3H), 3.10-3.12 (2H), 3.40 (1H), 3.56 (2H), 4.11-4.14 (2H), 7.16-7.17 (1H), 7.31-7.33 (2H), 7.68-7.69 (1H), 7.83-7.84 (2H), 11.40-12.48 (1H).

Synthesis Example No. 13 preparation of: 2,2,2-Trifluoroacetic acid compound with 2-(4-(2-(3-fluoro-4-methoxyphenyl)-4,5-dimethyl-5H-pyrrolo[2,3-d]pyrimidin-7(6H)-yl)phenyl) acetic acid (1:1) (compound No. 12)

13a): Ethyl 2-(2,4,6-trichloropyrimidin-5-yl)propanoate

Under a nitrogen atmosphere 2M LiHMDS (37.1 ml, 37.5 mmol, 1 eq.) was added dropwise at −78° C. to a stirred solution of ethyl 2-(2,4,6-trichloropyrimidin-5-yl)acetate (10 g, 37.2 mmol, 1.0 eq.) in dry THF (250 ml). The reaction mixture was stirred for 30 min at −78° C. and then allowed to warm up to 0° C. and stirred for 1 h. Iodomethane (4.7 ml, 75.0 mmol, 2 eq.) was added dropwise at 0° C. and the mixture was stirred for 2 h at 0° C. The reaction was stopped by addition of saturated aqueous NH$_4$Cl solution (100 ml) and water (250 ml). The crude product was extracted with ethyl acetate (3×150 ml). The combined organic layers were washed with saturated brine, dried over anhydrous sodium sulfate and concentrated under reduced pressure to get crude product which was purified by column chromatography to afford pure ethyl 2-(2,4,6-trichloropyrimidin-5-yl)propanoate (9.0 g, 85.5%) as a yellowish brown liquid.

13b): 2-(2,4,6-Trichloropyrimidin-5-yl)propan-1-ol

To a stirred solution of ethyl 2-(2,4,6-trichloropyrimidin-5-yl)propanoate (11.6 g, 40 mmol, 1 eq.) in dry THF (250 ml) under nitrogen atmosphere was added DIBAL-H (25% in toluene, 70 ml, 121 mmol, 3 eq.) and the reaction mixture was stirred at 0° C. for 4 h. The reaction was stopped by addition of 1N aqueous HCl solution at 0° C. and water (300 ml) and the crude product was extracted with dichloromethane (3×100 ml). The combined organic layers were washed with saturated brine, dried over anhydrous sodium sulfate and concentrated under reduced pressure to get crude product which was purified by column chromatography to afford pure 2-(2,4,6-trichloropyrimidin-5-yl)propan-1-ol (0.08 g, 44%) as an off white solid.

13c): 2-(2,4,6-Trichloropyrimidin-5-yl)propanal

To a stirred solution of 2-(2,4,6-trichloropyrimidin-5-yl)propan-1-ol (4.6 g, 19 mmol, 1 eq.) in DCM (500 ml) was added 1,1,1-triacetoxy-1,1-dihydro-1,2-benziodoxol-3(1H)-on (16.1 g, 38 mmol, 2 eq.) portion wise at 0° C. The reaction mixture was stirred at 0° C. for 3 h. The reaction mixture was filtered through Celite®. The solvent was removed under reduced pressure to get crude product which was purified by column chromatography to afford pure 2-(2,4,6-trichloropyrimidin-5-yl)propanal (4.3 g, 94.2%) as a white solid.

13d): 2,4-Dichloro-7-(2,4-dimethoxybenzyl)-5-methyl-6,7-dihydro-5H-pyrrolo[2,3-d]pyrimidine To a stirred solution of 2-(2,4,6-trichloropyrimidin-5-yl)propanal (4.3 g, 17.9 mmol, 1 eq.) in THF (120 ml) and AcOH (12 ml), (2,4-dimethoxyphenyl)methanamine (6.0 g, 35.8 mmol, 2 eq.) was added and the mixture was stirred for 30 min. Sodium triacetoxy borohydride (18.9 g, 89.5 mmol, 5 eq.) was added and the mixture was stirred for 12 h at RT. The reaction mixture was filtered through Celite® and the solvent was removed under reduced pressure. Water was added to the residue and the crude product was extracted with ethyl acetate (3×150 ml). The combined organic layers were washed with saturated brine, dried over anhydrous sodium sulfate and concentrated under reduced pressure to get crude product which was purified by trituration to afford pure 2,4-dichloro-7-(2,4-dimethoxybenzyl)-5-methyl-6,7-dihydro-5H-pyrrolo[2,3-d]pyrimidine.

13e): 2,4-Dichloro-5-methyl-6,7-dihydro-5H-pyrrolo[2,3-d]pyrimidine

To a stirred solution of 2,4-dichloro-7-(2,4-dimethoxybenzyl)-5-methyl-6,7-dihydro-5H-pyrrolo[2,3-d]pyrimidine (1.0 g, 2.83 mmol, 1 eq.) in dichloromethane (28 ml), TFA (10 ml) was added and the reaction mixture was refluxed for 2 h. The whole reaction mixture was evaporated under reduced pressure to obtain crude 2,4-dichloro-5-methyl-6,7-dihydro-5H-pyrrolo[2,3-d]pyrimidine which was used for the next step without further purification.

13f): Tert-butyl 2,4-dichloro-5-methyl-5H-pyrrolo[2,3-d]pyrimidine-7(6H)-carboxylate To a stirred solution of 2,4-dichloro-5-methyl-6,7-dihydro-5H-pyrrolo[2,3-d]pyrimidine (0.8 g, 2.53 mmol, 1 eq.) in DCM (30 ml), was added DMAP (0.061 g, 0.5 mmol, 0.2 eq.) followed by addition of Boc-anhydride (1.16 ml, 5.06 mmol, 2.0 eq.) and DIPEA (2.23 ml, 12.6 mmol, 5.0 eq.) at RT and the mixture was stirred for 2 h at reflux. Reaction mass was concentrated under reduced pressure to get crude product which was then purified by flash chromatography to afford tert-butyl 2,4-dichloro-5-methyl-5H-pyrrolo[2,3-d]pyrimidine-7(6H)-carboxylate (0.6 g, 79%) as a white solid.

13g): Tert-butyl 2-chloro-4,5-dimethyl-5H-pyrrolo[2,3-d]pyrimidine-7(6H)-carboxylate To a stirring solution of tert-butyl 2,4-dichloro-5-methyl-5H-pyrrolo[2,3-d]pyrimidine-7(6H)-carboxylate (2.0 g, 6.6 mmol, 1 eq.) in dry THF (66 ml) under argon atmosphere at RT was added Fe(acac)₃ (0.23 g, 0.66 mmol, 0.1 eq.). The reaction mixture was degassed and back filled with argon (4-5 times) and then methylmagnesium bromide (3M in THF, 5.5 ml, 16.5 mmol, 2.5 eq.) was added drop wise over 5 min at −78° C. and stirred for 3 h. The reaction mixture was quenched with saturated aqueous NH₄Cl solution at −78° C., diluted with ethyl acetate (150 ml). The organic layer was washed with water (2×50 ml) and then with brine (50 ml). The organic layer was dried over anhydrous Na₂SO₄, filtered and concentrated under reduced pressure to yield crude product which was then purified by column chromatography to afford tert-butyl 2-chloro-4,5-dimethyl-5H-pyrrolo[2,3-d]pyrimidine-7(6H)-carboxylate (1.2 g, 65%) as an off white solid.

1H-NMR (400 MHz; DMSO-d₆): 1.20-1.22 (3H), 1.49 (9H), 2.32 (3H), 3.36-3.41 (1H), 3.53-3.58 (1H), 4.06-4.11 (1H).

13h): 2-Chloro-4,5-dimethyl-6,7-dihydro-5H-pyrrolo[2,3-d]pyrimidine

To a solution of tert-butyl 2-chloro-4,5-dimethyl-5H-pyrrolo[2,3-d]pyrimidine-7(6H)-carboxylate (0.38 g, 1.4 mmol) in dichloromethane (13 ml) was added trifluoroacetic acid (2.5 ml) at 0° C. and then the mixture was stirred at RT for 2 h. The reaction mixture was concentrated under reduced pressure. Then the concentrated mass was diluted with EtOH (15 ml) and Amberlyst-A-21 (2 g) was added and the reaction mixture was stirred at RT for 2 h. The reaction mixture was filtered through sintered and the filtrate was concentrated and dried under reduce pressure to give the desired 2-chloro-4,5-dimethyl-6,7-dihydro-5H-pyrrolo[2,3-d]pyrimidine (0.22 g, 92%) as an off white solid.

13i): Tert-butyl 2-(4-(2-chloro-4,5-dimethyl-5H-pyrrolo[2,3-d]pyrimidin-7(6H)-yl)phenyl)acetate To a stirring solution of 2-chloro-4,5-dimethyl-6,7-dihydro-5H-pyrrolo[2,3-d]pyrimidine (1.0 g 5.46 mmol, 1 eq.) in 1,4-dioxane (22 ml) was added K₃PO₄ (2.31 g, 10.92 mmol 2.0 eq.), (4-iodo-phenyl)-acetic acid tert-butyl ester (2.6 g, 8.19 mmol, 1.5 eq.) and trans N,N'-dimethyl cyclohexa-1,2-diamine (0.54 g, 3.82 mmol 0.7 eq.). The resulting reaction mixture is degassed with argon for a period of 10 min and CuI (0.41 g, 2.18 mmol 0.4 eq.) is added and the mixture was degassed again. The reaction mixture is then heated to reflux for 3 h. At completion, the reaction mixture was diluted with dichloromethane (100 ml), filtered through Celite® and the filtrate was concentrated under reduced pressure to get crude product which was then purified by column chromatography to afford tert-butyl 2-(4-(2-chloro-4,5-dimethyl-5H-pyrrolo[2,3-d]pyrimidin-7(6H)-yl)phenyl)acetate (0.9 g, 42.6%) as white solid.

13i): Tert-butyl 2-(4-(2-(3-fluoro-4-methoxyphenyl)-4,5-dimethyl-5H-pyrrolo[2,3-d]pyrimidin-7(6H)-yl)phenyl)acetate Under an argon atmosphere 2M aqueous solution of Na₂CO₃ (0.4 ml, 0.8 mmol, 4.9 eq.) and Pd(PPh₃)₄ (6 mg, 0.005 mmol, 0.03 eq.) were added to a solution of tert-butyl 2-(4-(2-chloro-4,5-dimethyl-5H-pyrrolo[2,3-d]pyrimidin-7(6H)-yl)phenyl)acetate (60 mg, 0.16 mmol, 1.0 eq.) and 3-fluoro-4-methoxyphenylboronic acid (41 mg, 0.245 mmol, 1.5 eq.) in ethylenglycoldimethylether (3.2 ml) and the mixture was stirred for 1.5 h at 120° C. under microwave irradiation. The mixture was allowed to reach RT and then water (5 ml) was added. The crude product was extracted with dichloromethane (3×5 ml). The combined organic layers were dried over Na₂SO₄, filtrated and the solvent was removed under reduced pressure. The residue was purified by flash chromatography to afford tert-butyl 2-(4-(2-(3-fluoro-4-methoxyphenyl)-4,5-dimethyl-5H-pyrrolo[2,3-d]pyrimidin-7(6H)-yl)phenyl)acetate (59 mg, 78%).

13j): 2,2,2-Trifluoroacetic acid compound with 2-(4-(2-(3-fluoro-4-methoxyphenyl)-4,5-dimethyl-5H-pyrrolo[2,3-d]pyrimidin-7(6H)-yl)phenyl)acetic acid (1:1)

Tert-butyl 2-(4-(2-(3-fluoro-4-methoxyphenyl)-4,5-dimethyl-5H-pyrrolo[2,3-d]pyrimidin-7(6H)-yl)phenyl)acetate (59 mg, 0.127 mmol) was dissolved in trifluoroacetic acid (0.49 ml) and the mixture was stirred for 10 min at RT. The solvent was removed under reduced pressure and the residue was dissolved by drop wise addition of dichloromethane. The desired product was precipitated by addition of cyclohexane to give 2,2,2-trifluoroacetic acid compound with 2-(4-(2-(3-fluoro-4-methoxyphenyl)-4,5-dimethyl-5H-pyrrolo[2,3-d]pyrimidin-7(6H)-yl)phenyl)acetic acid (1:1) (61 mg, 92%) as a solid.

1H-NMR (600 MHz; DMSO-d₆, δ ppm): 1.32-1.35 (3H), 2.35-2.47 (3H), 3.55-3.65 (3H), 3.75-3.85 (1H), 3.90-4.00 (3H), 4.35-4-45 (1H), 7.32-7.42 (3H), 7.80-7.90 (2H), 8.01-8.07 (1H), 8.09-8.20 (1H), 12.50-13.50 (1H).

Synthesis Example No. 14 preparation of: 2,2,2-Trifluoroacetic acid compound with 2-(4-(2-(3-chloro-4-methoxyphenyl)-4,5-dimethyl-5H-pyrrolo[2,3-d]pyrimidin-7(6H)-yl)phenyl) acetic acid (1:1) (compound No. 24)

14a): Tert-butyl 2-(4-(2-(3-chloro-4-methoxyphenyl)-4,5-dimethyl-5H-pyrrolo[2,3-d]pyrimidin-7(6H)-yl)phenyl)acetate Under an argon atmosphere 2M aqueous solution of Na₂CO₃ (0.4 ml, 0.8 mmol, 4.9 eq.) and Pd(PPh₃)₄ (6 mg, 0.005 mmol, 0.03 eq.) were added to a solution of tert-butyl 2-(4-(2-chloro-4,5-dimethyl-5H-pyrrolo[2,3-d]pyrimidin-7(6H)-yl)phenyl)acetate (60 mg, 0.16 mmol, 1.0 eq.) and 3-chloro-4-methoxyphenylboronic acid (45 mg, 0.245 mmol, 1.5 eq.) in ethylenglycoldimethylether (3.2 ml) and the mixture was stirred for 1.5 h at 120° C. under microwave irradiation. The mixture was allowed to reach RT and then water (5 ml) was added. The crude product was extracted with dichloromethane (3×5 ml). The combined organic layers were dried over Na₂SO₄, filtrated and the solvent was removed under reduced pressure. The residue was purified by flash chromatography to afford tert-butyl 2-(4-(2-(3-chloro-4-methoxyphenyl)-4,5-dimethyl-5H-pyrrolo[2,3-d]pyrimidin-7(6H)-yl)phenyl)acetate (66 mg, 84%).

14b): 2,2,2-Trifluoroacetic acid compound with 2-(4-(2-(3-chloro-4-methoxyphenyl)-4,5-dimethyl-5H-pyrrolo[2,3-d]pyrimidin-7(6H)-yl)phenyl)acetic acid (1:1)

Tert-butyl 2-(4-(2-(3-chloro-4-methoxyphenyl)-4,5-dimethyl-5H-pyrrolo[2,3-d]pyrimidin-7(6H)-yl)phenyl)acetate (66 mg, 0.138 mmol) was dissolved in trifluoroacetic acid (0.53 ml) and the mixture was stirred for 10 min at RT. The solvent was removed under reduced pressure and the desired product was recrystallized in ethylacetate to give 2,2,2-trifluoroacetic acid compound with 2-(4-(2-(3-fluoro-4-methoxyphenyl)-4,5-dimethyl-5H-pyrrolo[2,3-d]pyrimidin-7(6H)-yl)phenyl)acetic acid (1:1) (63 mg, 85%) as a solid.

1H-NMR (600 MHz; DMSO-$d_6$, δ ppm): 1.32-1.35 (3H), 2.35-2.47 (3H), 3.55-3.65 (3H), 3.75-3.85 (1H), 3.90-4.00 (3H), 4.35-4-45 (1H), 7.32-7.42 (3H), 7.80-7.90 (2H), 8.22-8.26 (1H), 8.28-8.33 (1H), 12.50-13.50 (1H).

Synthesis Example No. 15 preparation of: 2-(3-(2-(5-chlorothiophen-2-yl)-4-ethyl-5H-pyrrolo[2,3-d]pyrimidin-7(6H)-yl)phenoxy)-N,N-dimethylacetamide (compound No. 40)

This compound can be synthesized in analogy to synthesis example 4.

1H-NMR (600 MHz; DMSO-$d_6$, δ ppm): 1.18-1.25 (3H), 2.54-2.64 (2H), 2.85 (3H), 3.03 (3H), 3.08-3.18 (2H), 4.08-4.16 (2H), 4.85 (2H), 6.62-6.68 (1H), 7.15-7.20 (1H), 7.29-7.35 (1H), 7.39-7.44 (1H), 7.58-7.61 (1H), 7.65-7.69 (1H).

Synthesis Example No. 18 preparation of: 4-(2-(3-chloro-4-methoxyphenyl)-4-methoxy-7H-pyrrolo[2,3-d]pyrimidin-7-yl)benzoic acid (compound No. 45)

18a): 2-Chloro-4-methoxy-7H-pyrrolo[2,3-d]pyrimidine

To a suspension of 2,4-dichloro-7H-pyrrolo[2,3-d]pyrimidine (600 mg, 3.19 mmol) in methanol (6 ml) was added sodiummethylate (1.2 g, 22.2 mmol) and the mixture was refluxed for 6 h. The reaction mixture was quenched with water (30 ml) and neutralized with acetic acid. The precipitate was filtered, washed with water (3×3 ml) and dried. The crude product was recrystallized from chloroform to give 2-chloro-4-methoxy-7H-pyrrolo[2,3-d]pyrimidine (478 mg, 82%) as a beige solid.

18b): Methyl 4-(2-chloro-4-methoxy-7H-pyrrolo[2,3-d]pyrimidin-7-yl)benzoate

To a solution of 2-chloro-4-methoxy-7H-pyrrolo[2,3-d]pyrimidine (300 mg, 1.63 mmol) in 1,2-dichloromethane (6 ml) was added (4-(methoxycarbonyl)phenyl)boronic acid (600 mg, 3.33 mmol), triethylamine (0.46 ml, 3.31 mmol), Cu(OAc)$_2$ (600 mg, 3.30 mmol) and powdered 4 Å molecular sieve and the mixture was stirred at RT for 23 h. The reaction mixture was diluted with THF and filtered over Celite®. The filtrate was concentrated under reduced pressure to give the crude product which was purified by column chromatography to afford methyl 4-(2-chloro-4-methoxy-7H-pyrrolo[2,3-d]pyrimidin-7-yl)benzoate (141 mg, 27%) as a white solid.

18c): methyl 4-(2-(3-chloro-4-methoxyphenyl)-4-methoxy-7H-pyrrolo[2,3-d]pyrimidin-7-yl)benzoate To a solution of methyl 4-(2-chloro-4-methoxy-7H-pyrrolo[2,3-d]pyrimidin-7-yl)benzoate (160 mg, 0.50 mmol) in 1,4-dioxane was added (3-chloro-4-methoxyphenyl)boronic acid (100 mg, 0.54 mmol), [1,1'-bis(diphenylphosphino)ferrocen]dichloropalladium(II) complex with dichloromethane (45 mg, 0.06 mmol) and Cs$_2$CO$_3$ (500 mg, 1.53 mmol) and the mixture was stirred at 95° C. for 1.5 h. The reaction mixture was cooled to RT and purified by flash chromatography to afford methyl 4-(2-(3-chloro-4-methoxyphenyl)-4-methoxy-7H-pyrrolo[2,3-d]pyrimidin-7-yl)benzoate (165 mg, 77%) as a white solid.

18d): 4-(2-(3-chloro-4-methoxyphenyl)-4-methoxy-7H-pyrrolo[2,3-d]pyrimidin-7-yl)benzoic acid To a suspension of methyl 4-(2-(3-chloro-4-methoxyphenyl)-4-methoxy-7H-pyrrolo[2,3-d]pyrimidin-7-yl)benzoate (140 mg, 0.33 mmol) in a mixture of methanol (3 ml) and 1,4-dioxane (3 ml) was added 1N NaOH (0.75 ml, 0.75 mmol) and the mixture was refluxed for 15 min. The mixture was cooled to RT and neutralized by addition of 1N HCl. The precipitate was filtered, washed with water (3×2 ml) and methanol (2×0.5 ml) and dried to give 4-(2-(3-chloro-4-methoxyphenyl)-4-methoxy-7H-pyrrolo[2,3-d]pyrimidin-7-yl)benzoic acid (128 mg, 95%) as a white solid.

13C-NMR (101 MHz, DMSO-$d_6$, δ ppm): 53.5, 56.2, 100.8, 104.6, 112.6, 121.1, 122.6, 126.4, 127.8, 128.5, 128.8, 130.5, 131.0, 141.0, 152.0, 155.7, 156.0, 162.5, 166.7.

Synthesis Example No. 19 preparation of: 4-(4-ethyl-2-(3-fluoro-4-methoxyphenyl)-5H-pyrrolo[2,3-d]pyrimidin-7(6H)-yl)benzoic acid (compound No. 6)

This compound can be synthesized in analogy to synthesis example No. 10.

1H-NMR (600 MHz; DMSO-$d_6$, δ ppm): 1.26-1.19 (3H), 2.65-2.68 (2H), 3.18-3.20 (2H), 3.92 (s, 3H), 4.19-4.22 (2H), 7.30-7.33 (1H), 7.50 (bs, 1H), 8.02-8.04 (2H), 8.07-8.10 (3H), 8.20-8.22 (1H).

Synthesis Example No. 20 preparation of: 4-(2-(5-chlorothiophen-2-yl)-4-ethyl-5H-pyrrolo[2,3-d]pyrimidin-7(6H)-yl)benzoic acid (compound No. 46)

This compound can be synthesized in analogy to synthesis example No 10.

1H-NMR (600 MHz; DMSO-$d_6$, δ ppm): 1.22-1.24 (3H), 2.59-2.62 (2H), 3.14-3.17 (2H), 4.17-4.19 (2H), 7.19 (1H), 7.77 (1H), 8.00-8.04 (4H), 12.63 (bs, 1H).

Synthesis Example No. 21 preparation of: 4-(4-ethyl-2-(3-fluoro-4-methoxyphenyl)-7H-pyrrolo[2,3-d]pyrimidin-7-yl)benzoic acid (compound No. 2)

This compound can be synthesized in analogy to synthesis example No. 5.

1H-NMR (600 MHz; DMSO-$d_6$, δ ppm): 1.40-1.43 (3H), 3.10-3.13 (2H), 3.92 (s, 3H), 7.01 (1H), 7.29-7.31 (1H), 8.07 (1H), 8.17-8.20 (5H), 8.28-8.29 (1H), 13.03 (bs, 1H).

Synthesis Example No. 22 preparation of: 2-(3-(4-ethyl-2-(3-fluoro-4-methoxyphenyl)-5H-pyrrolo[2,3-d]pyrimidin-7(6H)-yl)phenoxy)-N-(oxetan-3-yl)acetamide (compound No. 47)

This compound can be synthesized in analogy to synthesis example No. 4.

1H-NMR (400 MHz; DMSO-$d_6$, δ ppm): 8.86 (d, 1H, J=6.76 Hz), 8.17 (d, 1H, J=8.48 Hz), 8.06 (d, 1H, J=12.96 Hz), 7.71 (s, 1H), 7.56 (d, 1H, J=8.28 Hz), 7.36 (t, 1H, J=8.24 Hz), 7.29 (t, 1H, J=8.76 Hz), 6.69 (d, 1H, J=8.2 Hz), 4.92-4.85 (m, 1H), 4.7 (t, 2H, J=6.56 Hz), 4.57-4.51 (m, 4H), 4.13 (t, 2H, J=8.4 Hz), 3.91 (s, 3H), 3.16 (t, 2H, J=8.4 Hz), 2.66-2.6 (m, 2H), 1.26 (t, 3H, J=7.56 Hz).

Synthesis Example No. 23 preparation of: 1-(azetidin-1-yl)-2-(3-(4-ethyl-2-(3-fluoro-4-methoxyphenyl)-5H-pyrrolo[2,3-d]pyrimidin-7(6H)-yl)phenoxy)ethanone (compound No. 48)

This compound can be synthesized in analogy to synthesis example No. 4.

1H-NMR (400 MHz; DMSO-$d_6$, δ ppm): 8.16 (d, 1H, J=8.52 Hz), 8.08-8.04 (dd, 1H, J=1.8 Hz & 12.96 Hz), 7.7 (s, 1H), 7.46-7.44 (m, 1H), 7.35 (t, 1H, J=8.2 Hz), 7.28 (t, 1H, J=8.8 Hz), 6.63 (dd, 1H, J=2 Hz & 8.08 Hz), 4.63 (s, 2H), 4.29 (t, 2H, J=7.68 Hz), 4.13 (t, 2H, J=8.4 Hz), 3.93-3.89 (m, 5H), 3.15 (t, 2H, J=8.4 Hz), 2.65-2.6 (m, 2H), 2.25-2.21 (m, 2H), 1.26 (t, 3H, J=7.56 Hz).

Synthesis Example No. 24 preparation of: 2-(3-(4-ethyl-2-(3-fluoro-4-methoxyphenyl)-7H-pyrrolo[2,3-d]pyrimidin-7-yl)phenoxy)-1-(4-methylpiperazin-1-yl)ethanone (compound No. 49)

This compound can be synthesized in analogy to synthesis example No. 5.

1H-NMR (400 MHz; DMSO-$d_6$, δ ppm): 8.25 (d, 1H, J=8.64 Hz), 8.16 (dd, 1H, J=1.64 Hz, 13.04 Hz), 7.96 (d, 1H, J=3.68 Hz), 7.55-7.49 (m, 3H), 7.3 (t, 1H, J=8.76 Hz), 6.98-6.95 (m, 2H), 4.94 (2H), 3.91 (s, 3H), 3.45 (bs, 4H), 3.11 (q, 2H, J=7.52 Hz), 2.3 (bs, 2H), 2.22 (bs, 2H), 2.14 (s, 3H), 1.4 (t, 3H, J=7.52 Hz).

Synthesis Example No. 26 preparation of: 2-(3-(2-(3-fluoro-4-methoxyphenyl)-4-(methylsulfonyl)-7H-pyrrolo[2,3-d]pyrimidin-7-yl)phenoxy)-N,N-dimethylacetamide (compound No. 50)

This compound can be synthesized in analogy to synthesis example No. 33.

1H-NMR (600 MHz; DMSO-$d_6$, δ ppm): 2.85 (s, 3H), 3.02 (s, 3H), 3.56 (s, 3H), 3.93 (s, 3H), 4.95 (s, 2H), 7.04-7.06 (1H), 7.11-7.12 (1H), 7.33-7.35 (1H), 7.52-7.55 (3H), 8.18-8.21 (1H), 8.27-8.29 (2H).

Synthesis Example No. 27 preparation of: N-(cyclopropylmethyl)-2-(3-(4-ethyl-2-(3-fluoro-4-methoxyphenyl)-5H-pyrrolo[2,3-d]pyrimidin-7(6H)-yl)phenoxy)-N-methylacetamide (compound No. 51)

This compound can be synthesized in analogy to synthesis example No. 4.

1H-NMR (400 MHz; DMSO-$d_6$, T=100° C., δ ppm): 8.16 (d, 1H, J=8 Hz), 8.07 (d, 1H, J=12 Hz), 7.64 (s, 1H), 7.48 (d, 1H, J=8 Hz), 7.33 (t, 1H, J=8 Hz), 7.24 (t, 1H, J=8 Hz), 6.69 (dd, 1H, J=4 Hz & 8 Hz), 4.81 (s, 2H), 4.14 (t, 2H, J=8 Hz), 3.93 (s, 3H), 3.23 (d, 2H, J=8 Hz), 3.17 (t, 2H, J=8 Hz), 3.03 (s, 3H), 2.69-2.64 (m, 2H), 1.3 (t, 3H, J=8 Hz), 0.99-0.97 (m, 1H), 0.47-0.45 (m, 2H), 0.23-0.21 (m, 2H).

Synthesis Example No. 28 preparation of: 2-(3-(4-ethyl-2-(3-fluoro-4-methoxyphenyl)-7H-pyrrolo[2,3-d]pyrimidin-7-yl)phenoxy)-N-isopropylacetamide (compound No. 52)

This compound can be synthesized in analogy to synthesis example No. 5.

1H-NMR (400 MHz; DMSO-$d_6$, δ ppm): 8.26 (d, 1H, J=7.76 Hz), 8.16 (d, 1H, J=13.08 Hz), 7.97-7.92 (m, 2H), 7.61 (bs, 2H), 7.53 (t, 1H, J=7.92 Hz), 7.3 (t, 1H, J=8.4 Hz), 7.02-6.96 (m, 2H), 4.57 (2H), 3.97-3.91 (m, 4H), 3.13-3.06 (m, 2H), 1.41 (t, 3H, J=7.44 Hz), 1.08 (d, 6H, J=7.2 Hz).

Synthesis Example No. 29 preparation of: 2-(3-(4-ethyl-2-(3-fluoro-4-methoxyphenyl)-7H-pyrrolo[2,3-d]pyrimidin-7-yl)phenoxy)-1-morpholinoethanone (compound No. 53)

This compound can be synthesized in analogy to synthesis example No. 5.

1H-NMR (400 MHz; DMSO-$d_6$, δ ppm): 8.25 (d, 1H, J=8.6 Hz), 8.16 (d, 1H, J=12.88 Hz), 7.96 (d, 1H, J=3.64 Hz), 7.56-7.51 (m, 3H), 7.3 (t, 1H, J=8.76 Hz), 7.0-6.95 (m, 2H), 4.96 (s, 2H), 3.91 (s, 3H), 3.58-3.46 (m, 8H), 3.11 (q, 2H, J=7.56 Hz), 1.41 (t, 3H, J=7.56 Hz).

Synthesis Example No. 30 preparation of: 1-(azetidin-1-yl)-2-(3-(4-ethyl-2-(3-fluoro-4-methoxyphenyl)-7H-pyrrolo[2,3-d]pyrimidin-7-yl)phenoxy)ethanone (compound No. 54)

This compound can be synthesized in analogy to synthesis example No. 5.

1H-NMR (400 MHz; DMSO-$d_6$, δ ppm): 8.26 (d, 1H, 8.56 Hz), 8.15 (d, 1H, J=13 Hz), 7.98 (d, 1H, J=3.68 Hz), 7.59-7.50 (m, 3H), 7.29 (t, 1H, J=8.68 Hz), 6.98-6.95 (m, 2H), 4.71 (s, 2H), 4.28 (t, 2H, J=7.6 Hz), 3.93-3.89 (m, 5H), 3.13-3.07 (m, 2H), 2.25-2.21 (m, 2H), 1.41 (t, 3H, J=8 Hz).

Synthesis Example No. 31 preparation of: N-(cyclopropylmethyl)-2-(3-(4-ethyl-2-(3-fluoro-4-methoxyphenyl)-7H-pyrrolo[2,3-d]pyrimidin-7-yl)phenoxy)-N-methylacetamide (compound No. 55)

This compound can be synthesized in analogy to synthesis example No. 5.
1H-NMR (400 MHz; DMSO-$d_6$, δ ppm): 8.26 (d, 1H, J=8.0 Hz), 8.16 (d, 1H, J=16 Hz), 7.85 (d, 1H, J=4 Hz), 7.59-7.48 (m, 3H), 7.26 (t, 1H, J=8 Hz), 7.0 (d, 1H, J=8 Hz), 6.9 (d, 1H, J=4 Hz), 4.89 (s, 2H), 3.94 (s, 3H), 3.24 (d, 2H, J=8 Hz), 3.15-3.1 (m, 2H), 3.03 (s, 3H), 1.45 (t, 3H, J=8 Hz), 1.0-0.97 (m, 1H), 0.45 (bd, 2H), 0.22 (bd, 2H).

Synthesis Example No. 32 preparation of: 2-(3-(4-ethyl-2-(3-fluoro-4-methoxyphenyl)-5H-pyrrolo[2,3-d]pyrimidin-7(6H)-yl)phenoxy)-N-(2-hydroxyethyl)acetamide (compound No. 56)

This compound can be synthesized in analogy to synthesis example No. 4.
1H-NMR (400 MHz; DMSO-$d_6$, δ ppm): 8.17 (d, 1H, J=8.28 Hz), 8.09-8.01 (m, 2H), 7.59-7.56 (m, 1H), 7.68 (s, 1H), 7.38-7.27 (m, 2H), 6.68 (d, 1H, J=8 Hz), 4.72 (s, 2H), 4.54 (s, 2H), 4.13 (t, 2H, J=8.24 Hz), 3.91 (s, 3H), 3.44 (bs, 2H), 3.25-3.13 (m, 4H), 2.66-2.5 (2H), 1.26 (t, 3H, J=7.56 Hz).

Synthesis Example No. 33 preparation of: 2-(4-(2-(3-fluoro-4-methoxyphenyl)-4-(methylsulfonyl)-7H-pyrrolo[2,3-d]pyrimidin-7-yl)phenyl)acetic acid (compound No. 57)

33a): 2-chloro-4-(methylthio)-7H-pyrrolo[2,3-d]pyrimidine

To a stirring solution of 2,4-dichloro-7H-pyrrolo[2,3-d]pyrimidine (0.1 g, 0.53 mmol) in DMSO (0.7 ml) at RT was added sodiumthiomethoxide (0.045 g, 0.64 mmol, 1.2 eq) and the mixture was stirred at RT for 2 h. Then water was added to induce precipitation. The precipitate was collected and dried under vacuum to give 2-chloro-4-(methylthio)-7H-pyrrolo[2,3-d]pyrimidine (0.1 g, 94%) as an off white solid.

33b): tert-butyl 2-(4-(2-chloro-4-(methylthio)-7H-pyrrolo[2,3-d]pyrimidin-7-yl)phenyl)acetate To a stirring solution of 2-chloro-4-(methylthio)-7H-pyrrolo[2,3-d]pyrimidine (0.1 g, 0.50 mmol, 1 eq.) in dimethyl sulfoxide (2 ml) was added $K_3PO_4$ (0.213 g, 1 mmol, 2 eq.), 4-iodo-phenyl)-acetic acid tert-butyl ester (0.239 g, 0.753 mmol, 1.5 eq.) and trans-N,N'-dimethylcyclohexane-1,2-diamine (0.031 ml, 0.201 mmol, 0.4 eq). The resulting reaction mixture was degassed with argon for a period of 10 min and CuI (0.019 g, 0.1 mmol, 0.2 eq.) was added. The reaction mixture was then heated at 60° C. for 2 h. At completion, the reaction mixture was allowed to come to RT and filtered over Celite®. The filtrate was diluted with ethyl acetate (50 ml), the organic layer was washed with water (2×10 ml) and then with brine (10 ml). The organic layer was dried over anhydrous $Na_2SO_4$, filtered and concentrated under reduced pressure to yield crude residue which was purified by column chromatography to afford tert-butyl 2-(4-(2-chloro-4-(methylthio)-7H-pyrrolo[2,3-d]pyrimidin-7-yl)phenyl)acetate (0.11 g, 56%) as off white solid.

33c): tert-butyl 2-(4-(2-(3-fluoro-4-methoxyphenyl)-4-(methylthio)-7H-pyrrolo[2,3-d]pyrimidin-7-yl)phenyl)acetate To a stirring solution of tert-butyl 2-(4-(2-chloro-4-(methylthio)-7H-pyrrolo[2,3-d]pyrimidin-7-yl)phenyl)acetate (0.75 g, 1.92 mmol, 1 eq.) and 3-fluoro-4-methoxy-phenyl boronic acid (0.491 g, 2.89 mmol, 1.5 eq.) in a 1:1 mixture solvents of tetrahydrofuran and water (12 ml) under argon atmosphere was added $K_2CO_3$ (0.532 g, 3.85 mmol, 2.0 eq.) and $PdCl_2(PPh_3)_2$ (0.27 g, 0.385 mmol, 0.2 eq). The resulting reaction mixture was stirred for 2 h at 90° C. The reaction mixture was filtered over Celite®, filtrate was diluted with ethyl acetate (100 ml), the organic layer was washed with water (2×30 ml) and then with brine (30 ml). The organic layer was dried over anhydrous $Na_2SO_4$, filtered and concentrated under reduced pressure to yield crude residue which was purified by column chromatography to afford tert-butyl 2-(4-(2-(3-fluoro-4-methoxyphenyl)-4-(methylthio)-7H-pyrrolo[2,3-d]pyrimidin-7-yl)phenyl)acetate (0.65 g, 70%) as off white solid.

33d): tert-butyl 2-(4-(2-(3-fluoro-4-methoxyphenyl)-4-(methylsulfonyl)-7H-pyrrolo[2,3-d]pyrimidin-7-yl)phenyl)acetate To a stirring solution of tert-butyl 2-(4-(2-(3-fluoro-4-methoxyphenyl)-4-(methylthio)-7H-pyrrolo[2,3-d]pyrimidin-7-yl)phenyl)acetate (0.19 g, 0.396 mmol) in a mixture solvents of glacial acetic acid/water/ethanol (1 ml, 2:2:3) at 0° C. was added oxone (0.243 g, 0.396 mmol, 1 eq) in portions. The reaction mixture was stirred at RT for 16 h. The reaction mixture was diluted with dichloromethane (100 ml), filtered and the mother liquor was portioned between water and dichloromethane. The organic layer was washed with water (2×30 ml) and brine (2×30 ml) The organic layer was dried over anhydrous $Na_2SO_4$, filtered and concentrated under reduced pressure to yield crude product which was purified by column to afford tert-butyl 2-(4-(2-(3-fluoro-4-methoxyphenyl)-4-(methylsulfonyl)-7H-pyrrolo[2,3-d]pyrimidin-7-yl)phenyl)acetate (0.065 g, 32%) as a white solid.

33e): 2-(4-(2-(3-fluoro-4-methoxyphenyl)-4-(methylsulfonyl)-7H-pyrrolo[2,3-d]pyrimidin-7-yl)phenyl) acetic acid To a solution of tert-butyl 2-(4-(2-(3-fluoro-4-methoxyphenyl)-4-(methylsulfonyl)-7H-pyrrolo[2,3-d]pyrimidin-7-yl)phenyl)acetate (0.04 g, 0.078 mmol) in dichloromethane (4 ml) was added trifluoroacetic acid (1 ml) at 0° C. and then stirred at RT for 2 h. The reaction mixture was concentrated under reduced pressure to give the desired 2-(4-(2-(3-fluoro-4-methoxyphenyl)-4-(methylsulfonyl)-7H-pyrrolo[2,3-d]pyrimidin-7-yl)phenyl)acetic acid (0.03 g, 84% as off white solid.
1H-NMR (400 MHz; DMSO-$d_6$, δ ppm): 3.56 (s, 3H), 3.72 (s, 2H), 3.93 (s, 3H), 7.11-7.12 (1H), 7.33-7.37 (1H), 7.53-7.56 (2H), 7.87-7.90 (2H), 8.16-8.20 (1H), 8.25-8.30 (2H), 12.44 (s, 1H).

Synthesis Example No. 34 preparation of: 2-(3-(2-(3-fluoro-4-methoxyphenyl)-4-(methylthio)-7H-pyrrolo[2,3-d]pyrimidin-7-yl) phenoxy)-N,N-dimethylacetamide (compound No. 58)

This compound can be synthesized in analogy to synthesis example No. 33.

$^1$H-NMR (600 MHz; DMSO-d$_6$, δ ppm): 2.80 (s, 3H), 2.85 (s, 3H), 3.01 (s, 3H), 3.92 (s, 3H), 4.93 (s, 2H), 6.75-6.76 (1H), 6.98-6.99 (1H), 2.29-7.32 (1H), 7.50-7.53 (3H), 7.91-7.92 (1H), 8.16-8.18 (1H), 8.26-8.27 (1H).

Synthesis Example No. 35 preparation of: N-cyclopropyl-2-(3-(4-ethyl-2-(3-fluoro-4-methoxyphenyl)-7H-pyrrolo[2,3-d]pyrimidin-7-yl)phenoxy)-N-methylacetamide (compound No. 59)

This compound can be synthesized in analogy to synthesis example No. 5.

$^1$H-NMR (400 MHz; DMSO-d$_6$, δ ppm): 8.25 (d, 1H, J=8.68 Hz), 8.15 (d, 1H, J=12.96 Hz), 7.96 (d, 1H, 3.64 Hz), 7.52-7.48 (m, 3H), 7.29 (t, 1H, J=8.76 Hz), 6.94 (d, 2H, J=3.72 Hz), 5.07 (s, 2H), 3.9 (s, 3H), 3.09 (q, 2H, J=7.48 Hz), 2.80-2.72 (m, 4H), 1.41 (t, 3H, J=7.56 Hz), 0.78-0.81 (m, 4H).

Synthesis Example No. 36 preparation of: N-ethyl-2-(3-(4-ethyl-2-(3-fluoro-4-methoxyphenyl)-5H-pyrrolo[2,3-d]pyrimidin-7(6H)-yl)phenoxy)acetamide (compound No. 60)

This compound can be synthesized in analogy to synthesis example No. 4.

$^1$H-NMR (400 MHz; DMSO-d$_6$, ☐☐ppm): 8.16 (d, 1H, J=8.4 Hz), 8.11-8.05 (m, 2H), 7.68 (s, 1H), 7.58-7.56 (m, 1H), 7.35 (t, 1H, J=8.2 Hz), 7.28 (t, 1H, J=8.72 Hz), 6.68 (dd, 1H, J=1.96 Hz & 8.24 Hz), 4.51 (s, 2H), 4.13 (t, 2H, J=8.6 Hz), 3.91 (s, 3H), 3.19-3.13 (m, 4H), 2.63-2.61 (m, 2H), 1.26 (t, 3H, J=7.52 Hz), 1.05 (t, 3H, J=7.2 Hz).

Synthesis Example No. 37 preparation of: 2-(3-(4-ethyl-2-(3-fluoro-4-methoxyphenyl)-7H-pyrrolo[2,3-d]pyrimidin-7-yl)phenoxy)-N-(oxetan-3-yl)acetamide (compound No. 61)

This compound can be synthesized in analogy to synthesis example No. 5.

$^1$H-NMR (400 MHz; DMSO-d$_6$, δ ppm): 8.88 (d, 1H, J=6.52 Hz), 8.26 (d, 1H, J=8.52 Hz), 8.16 (dd, 1H, J=13.04 Hz & 1.52 Hz), 7.97 (d, 1H, J=3.68 Hz), 7.63-7.61 (m, 2H), 7.54 (t, 1H, J=8.32 Hz), 7.3 (t, 1H, J=8.76 Hz), 7.02 (d, 1H, J=7.6 Hz), 6.96 (d, 1H, J=3.6 Hz), 4.92-4.87 (m, 1H), 4.69 (t, 2H, J=8 Hz), 4.64 (s, 2H), 4.52 (t, 2H, J=6.44 Hz), 3.91 (s, 3H), 3.11 (q, 2H, J=7.56 Hz), 1.41 (t, 3H, J=7.6 Hz).

Synthesis Example No. 39 preparation of: 2-(3-(4-ethyl-2-(3-fluoro-4-methoxyphenyl)-7H-pyrrolo[2,3-d]pyrimidin-7-yl)phenoxy) acetamide (compound No. 62)

This compound can be synthesized in analogy to synthesis example No. 5.

$^1$H-NMR (400 MHz; DMSO-d$_6$, δ ppm): 8.25 (d, 1H, J=8.68 Hz), 8.16 (d, 1H, J=12.76 Hz), 7.59-7.51 (m, 5H), 7.42 (bs, 1H), 7.31 (t, 1H, J=8 Hz), 7.0 (d, 1H, J=7.52 Hz), 6.96 (d, 1H, J=3.36 Hz), 4.57 (s, 2H), 3.91 (s, 3H), 3.13-3.07 (m, 2H), 1.41 (t, 3H, J=7.48 Hz).

Synthesis Example No. 40 preparation of: N-ethyl-2-(3-(4-ethyl-2-(3-fluoro-4-methoxyphenyl)-7H-pyrrolo[2,3-d]pyrimidin-7-yl) phenoxy)acetamide (compound No. 63)

This compound can be synthesized in analogy to synthesis example No. 5.

$^1$H-NMR (400 MHz; DMSO-d$_6$, δ ppm): 8.26 (d, 1H, J=8.32 Hz), 8.18-8.15 (m, 2H), 7.97 (d, 1H, J=3.68 Hz), 7.63-7.61 (m, 2H), 7.54 (t, 1H, J=8.52 Hz), 7.29 (t, 1H, J=8.8 Hz), 7.01 (bd, 1H, J=8.84 Hz), 6.96 (d, 1H, J=3.68 Hz), 4.59 (s, 2H), 3.91 (s, 3H), 3.2-3.07 (m, 4H), 1.41 (t, 3H, J=7.6 Hz), 1.04 (t, 3H, J=7.16 Hz).

Synthesis Example No. 41 preparation of: 2-(3-(4-ethyl-2-(3-fluoro-4-methoxyphenyl)-5H-pyrrolo[2,3-d]pyrimidin-7(6H)-yl)phenoxy)acetamide (compound No. 64)

This compound can be synthesized in analogy to synthesis example No. 4.

$^1$H-NMR (400 MHz; DMSO-d$_6$, δ ppm): 8.17 (d, 1H, J=8.44 Hz), 8.06 (dd, 1H, J=1.8 Hz & 13 Hz), 7.66 (s, 1H), 7.57-7.54 (m, 2H), 7.41 (bs, 1H), 7.35-7.27 (m, 2H), 6.67 (dd, 1H, J=2 Hz & 8.04 Hz), 4.49 (s, 2H), 4.13 (t, 2H, J=8.36 Hz), 3.91 (s, 3H), 3.15 (t, 2H, J=7.92 Hz), 2.65-2.6 (m, 2H), 1.26 (t, 3H, J=7.6 Hz).

Synthesis Example No. 42 preparation of: 2-(3-(4-ethyl-2-(3-fluoro-4-methoxyphenyl)-5H-pyrrolo[2,3-d]pyrimidin-7(6H)-yl)phenoxy)-N-methylacetamide (compound No. 65)

This compound can be synthesized in analogy to synthesis example No. 4.

$^1$H-NMR (400 MHz; DMSO-d$_6$, δ ppm): 8.17 (d, 1H, J=8.88 Hz), 8.09-8.05 (m, 2H), 7.66 (s, 1H), 7.58-7.56 (m, 1H), 7.35 (t, 1H, J=8.2 Hz), 7.29 (t, 1H, J=8.76 Hz), 6.67 (dd, 1H, J=2.04 Hz & 8.2 Hz), 4.53 (s, 2H), 4.12 (t, 2H, J=8.4 Hz), 3.91 (s, 3H), 3.15 (t, 2H, J=8.44 Hz), 2.67-2.59 (m, 5H), 1.26 (t, 3H, J=7.6 Hz).

Synthesis Example No. 43 preparation of: 2-(3-(4-ethyl-2-(3-fluoro-4-methoxyphenyl)-7H-pyrrolo[2,3-d]pyrimidin-7-yl)phenoxy)-N-methylacetamide (compound No. 66)

This compound can be synthesized in analogy to synthesis example No. 5.
$^1$H-NMR (400 MHz; DMSO-$d_6$, δ ppm): 8.25 (d, 1H, J=8.84 Hz), 8.18-8.1 (m, 2H), 7.97 (d, 1H, J=3.68 Hz), 7.62-7.6 (m, 2H), 7.54 (t, 1H, J=8.04 Hz), 7.3 (t, 1H, J=8.72 Hz), 7.01 (bd, 1H, J=8.56 Hz), 6.96 (d, 1H, J=3.64 Hz), 4.6 (s, 2H), 3.91 (s, 3H), 3.13-3.07 (m, 2H), 2.66 (d, 3H, J=4.52 Hz), 1.41 (t, 3H, J=7.56 Hz).

Synthesis Example No. 44 preparation of: 2-(3-(4-ethyl-2-(3-fluoro-4-methoxyphenyl)-7H-(compound No. 67)

This compound can be synthesized in analogy to synthesis example No. 5.
$^1$H-NMR (400 MHz; DMSO-$d_6$, δ ppm): 8.25 (d, 1H, J=8.88 Hz), 8.16 (d, 1H, J=13.2 Hz), 8.09 (bt, 1H, J=5.2 Hz), 7.98 (d, 1H, J=3.6 Hz), 7.64-7.61 (m, 2H), 7.54 (t, 1H, J=8 Hz), 7.3 (t, 1H, J=8 Hz), 7.01-7.04 (m, 2H), 6.96 (d, 1H, J=4 Hz), 4.72 (t, 1H, J=5.6 Hz), 4.62 (s, 2H), 3.91 (s, 3H), 3.46-3.42 (m, 2H), 3.25-3.22 (m, 2H), 3.13-3.07 (m, 2H), 1.41 (t, 3H, J=7.6 Hz).

Synthesis Example No. 45 preparation of: N-cyclopropyl-2-(3-(4-ethyl-2-(3-fluoro-4-methoxyphenyl)-5H-pyrrolo[2,3-d]pyrimidin-7(6H)-yl)phenoxy)-N-methylacetamide (compound No. 68)

This compound can be synthesized in analogy to synthesis example No. 4.
$^1$H-NMR (400 MHz; DMSO-$d_6$, δ ppm): 8.15 (d, 1H, J=8.76 Hz), 8.05 (d, 1H, J=12.92 Hz), 7.57 (s, 1H), 7.5-7.48 (m, 1H), 7.35-7.26 (m, 2H), 6.63-6.61 (m, 1H), 4.98 (s, 2H), 4.13 (t, 2H, J=8.6 Hz), 3.9 (s, 3H), 3.15 (t, 2H, J=8.32 Hz), 2.81 (s, 4H), 2.65-2.59 (m, 2H), 1.26 (t, 3H, J=7.52 Hz), 0.79-0.86 (m, 4H).

Synthesis Example No. 46 preparation of: 2-(4-(2-(3-fluoro-4-methoxyphenyl)-4-(methylthio)-7H-pyrrolo[2,3-d]pyrimidin-7-yl)phenyl)acetic acid (compound No. 69)

This compound can be synthesized in analogy to synthesis example No. 33.
$^1$H-NMR (600 MHz; DMSO-$d_6$, δ ppm): 2.80 (s, 3H), 3.70 (s, 2H), 3.91 (s, 3H), 6.75-6.76 (1H), 7.30-7.33 (1H), 7.50-7.51 (2H), 7.86-7.87 (2H), 7.90-7.91 (1H), 8.14-8.16 (1H), 8.25-8.26 (1H), 12.40 (s, 1H).

Synthesis Example No. 47 preparation of: 2-(3-(2-(3-fluoro-4-methoxyphenyl)-4-methyl-5-(methylsulfonyl)-7H-pyrrolo[2,3-d]pyrimidin-7-yl)phenoxy)-N,N-dimethylacetamide (compound No. 70)

47a): tert-butyl 2-chloro-4-methyl-7H-pyrrolo[2,3-d]pyrimidine-7-carboxylate

To a solution of tert-butyl 2,4-dichloro-7H-pyrrolo[2,3-d]pyrimidine-7-carboxylate (5.0 g, 17.42 mmol, 1 eq.) in tetrahydrofuran (52 ml) under argon atmosphere was added trimethylboroxine (5.46 g, 43.55 mmol, 2.5 eq.) and $K_3PO_4$ (7.38 g, 34.8 mmol, 2 eq.) followed by addition of $PdCl_2(PPh_3)_2$ (1.22 g, 1.74 mmol, 0.1 eq.) and the mixture was refluxed for 2 h. Reaction mass was cooled to RT, diluted with dichloromethane (100 ml), filtered through Celite® and the filtrate is concentrated to get crude product which was then purified by flash chromatography to afford tert-butyl 2-chloro-4-methyl-7H-pyrrolo[2,3-d]pyrimidine-7-carboxylate (2.0 g, 43%) as a white solid.

47b): tert-butyl 2-(3-fluoro-4-methoxyphenyl)-4-methyl-7H-pyrrolo[2,3-d]pyrimidine-7-carboxylate To a stirring solution of tert-butyl 2-chloro-4-methyl-7H-pyrrolo[2,3-d]pyrimidine-7-carboxylate (10.0 g, 37.4 mmol, 1 eq.) and 3-fluoro-4-methoxy-phenyl boronic acid (9.55 g, 56.17 mmol, 1.5 eq.) in a 1:1 mixture solvents of tetrahydrofuran and water (224 ml) under argon atmosphere was added $K_2CO_3$ (10.33 g, 74.9 mmol, 2.0 eq.) and $PdCl_2(PPh_3)_2$ (5.25 g, 7.49 mmol, 0.2 eq). The resulting reaction mixture was stirred for 2 h at 90° C. The reaction mixture was filtered over Celite®, filtrate was diluted with ethyl acetate (500 ml), the organic layer was washed with water (2×150 ml) and then by brine (150 ml). The organic layer was dried over anhydrous $Na_2SO_4$, filtered and concentrated under reduced pressure to give crude residue which was purified by column chromatography to afford tert-butyl 2-(3-fluoro-4-methoxyphenyl)-4-methyl-7H-pyrrolo[2,3-d]pyrimidine-7-carboxylate (6.8 g, 51%) as off white solid.

47c): 2-(3-fluoro-4-methoxyphenyl)-4-methyl-7H-pyrrolo[2,3-d]pyrimidine

To a solution of tert-butyl 2-(3-fluoro-4-methoxyphenyl)-4-methyl-7H-pyrrolo[2,3-d]pyrimidine-7-carboxylate (6.8 g, 19.04 mmol) in dichloromethane (190 ml) was added trifluoroacetic acid (38 ml) at 0° C. and then stirred at RT for 2 h. The reaction mixture was concentrated under reduced pressure. Then the concentrated mass was diluted with ethanol (150 ml) and Amberlyst-A-21 (30 g) was added and the reaction mixture was stirred at RT for 2 h. The reaction mixture was filtered through sintered and filtrate was concentrated and dried under reduce pressure to 2-(3-fluoro-4-methoxyphenyl)-4-methyl-7H-pyrrolo[2,3-d]pyrimidine (4.5 g, 92%) as off white solid.

47d): 2-(3-fluoro-4-methoxyphenyl)-5-iodo-4-methyl-7H-pyrrolo[2,3-d]pyrimidine

To a stirring solution of 2-(3-fluoro-4-methoxyphenyl)-4-methyl-7H-pyrrolo[2,3-d]pyrimidine (4.0 g, 15.56 mmol, 1 eq) in DMF (26 ml) was added KOH (2.17 g, 38.91 mmol, 2.5 eq) at RT under inert atmosphere and stirred for 20 min at RT. Then iodine (3.95 g, 15.56 mmol, 1 eq) dissolved in DMF (4.6 ml) was added at RT and the mixture was stirred for 2 h. Reaction mixture was poured onto crushed ice, the precipitate formed was filtered, washed with cold water (10 ml) and dried to get 2-(3-fluoro-4-methoxyphenyl)-5-iodo-4-methyl-7H-pyrrolo[2,3-d]pyrimidine (5.0 g, 84%) as off white solid.

47e): tert-butyl 2-(3-fluoro-4-methoxyphenyl)-5-iodo-4-methyl-7H-pyrrolo[2,3-d]pyrimidine-7-carboxylate To a stirring solution of 2-(3-fluoro-4-methoxyphenyl)-5-iodo-4-methyl-7H-pyrrolo[2,3-d]pyrimidine (0.1 g, 0.26 mmol, 1 eq) in tetrahydrofuran (2 ml), NaH (0.015 g, 0.39 mmol, 1.5 eq) was added portion wise at 0° C. and the mixture was stirred for 10 min. Then Boc-anhydride (0.085 g, 0.39 mmol, 1.5 eq) was added drop wise and the resulting reaction mixture was stirred for 1 h at RT. The reaction mixture was quenched with crushed ice, extracted with ethyl acetate (2×50 ml), the organic layer was washed with water (2×20 ml) and then with brine (20 ml). The organic layer was dried over anhydrous $Na_2SO_4$, filtered and concentrated under reduced pressure to give crude residue which was purified by column chromatography to afford tert-butyl 2-(3-fluoro-4-methoxyphenyl)-5-iodo-4-methyl-7H-pyrrolo[2,3-d]pyrimidine-7-carboxylate (0.11 g, 87%) as off white solid.

47f): 2-(3-fluoro-4-methoxyphenyl)-4-methyl-5-(methylsulfonyl)-7H-pyrrolo[2,3-d]pyrimidine A mixture of tert-butyl 2-(3-fluoro-4-methoxyphenyl)-5-iodo-4-methyl-7H-pyrrolo[2,3-d]pyrimidine-7-carboxylate (0.5 g, 0.03 mmol), methanesulfonic acid sodium salt (0.127 g, 1.2 eq, 1.24 mmol), L-proline sodium salt (0.028 g, 0.2 eq, 0.207 mmol), CuI (0.02 g, 0.1 eq, 0.103 mmol) and DMSO (2 ml) in a sealed tube was heated to 90° C. under argon atmosphere for 16 h. The cooled reaction mixture was diluted with water (50 ml) and extracted with ethyl acetate (3×50 ml). Combined organic layer was washed with brine (50 ml), dried over anhydrous $Na_2SO_4$ and evaporated under reduced pressure. The crude product was purified by column chromatography to afford 2-(3-fluoro-4-methoxyphenyl)-4-methyl-5-(methylsulfonyl)-7H-pyrrolo[2,3-d]pyrimidine (0.08 g, 18%) as off white solid.

47g): 2-(3-(2-(3-fluoro-4-methoxyphenyl)-4-methyl-5-(methylsulfonyl)-7H-pyrrolo[2,3-d]pyrimidin-7-yl)phenoxy)-N,N-dimethylacetamide To a stirring solution of 2-(3-fluoro-4-methoxyphenyl)-4-methyl-5-(methylsulfonyl)-7H-pyrrolo[2,3-d]pyrimidine (0.15 g, 0.44 mmol, 1 eq.) in dimethyl sulfoxide (2 ml) was added $K_3PO_4$ (0.189 g, 0.89 mmol, 2 eq.), 2-(3-iodo-phenoxy)-N,N-dimethyl-acetamide (0.204 g, 0.67 mmol, 1.5 eq.) and trans-N,N'-dimethylcyclohexane-1,2-diamine (0.05 ml, 0.313 mmol, 0.7 eq). The resulting reaction mixture was degassed with argon for a period of 10 min and CuI (0.034 g, 0.179 mmol, 0.4 eq.) was added and degassed again. The reaction mixture was then heated at 100° C. for 5 h. At completion, the reaction mixture was allowed to come to RT and filtered over Celite®, filtrate was diluted with ethyl acetate (50 ml), the organic layer was washed with water (2×10 ml) and then by brine (10 ml). The organic layer was dried over anhydrous $Na_2SO_4$, filtered and concentrated under reduced pressure to yield crude residue which was purified by column to afford 2-(3-(2-(3-fluoro-4-methoxyphenyl)-4-methyl-5-(methylsulfonyl)-7H-pyrrolo[2,3-d]pyrimidin-7-yl)phenoxy)-N,N-dimethylacetamide (0.083 g, 36%) as off white solid.

$^1$H-NMR (600 MHz; DMSO-$d_6$, δ ppm): 2.84 (s, 3H), 3.01 (s, 3H), 3.05 (s, 3H), 3.44 (s, 3H), 3.92 (s, 3H), 4.95 (s, 2H), 7.08-7.09 (1H), 7.29-7.32 (1H), 7.50-7.51 (2H), 7.53-7.56 (1H), 8.12-8.14 (1H), 8.23-8.24 (1H), 8.50 (s, 1H).

Synthesis Example No. 48 preparation of: 2-(4-(2-(3-fluoro-4-methoxyphenyl)-4-methyl-5-(methylsulfonyl)-7H-pyrrolo[2,3-d]pyrimidin-7-yl)phenyl)acetic acid (compound No. 71)

This compound can be synthesized in analogy to synthesis example No. 47.

$^1$H-NMR (600 MHz; DMSO-$d_6$, δ ppm): 3.05 (s, 3H), 3.44 (s, 3H), 3.73 (s, 2H), 3.91 (s, 3H), 7.31-7.34 (1H), 7.53-7.55 (2H), 7.86.7.87 (2H), 8.10-8.13 (1H), 8.21-8.23 (1H), 8.51 (s, 1H), 12.42 (bs, 1H).

Synthesis Example No. 49 preparation of: 2-(3-(2-(3-fluoro-4-methoxyphenyl)-4-methyl-5-(methylthio)-7H-pyrrolo[2,3-d]pyrimidin-7-yl)phenoxy)-N,N-dimethylacetamide (compound No. 72)

49a): methyl 3-((2-(3-fluoro-4-methoxyphenyl)-4-methyl-7H-pyrrolo[2,3-d]pyrimidin-5-yl)thio)propanoate To a stirring solution of tert-butyl 2-(3-fluoro-4-methoxyphenyl)-5-iodo-4-methyl-7H-pyrrolo[2,3-d]pyrimidine-7-carboxylate (3.5 g, 7.24 mmol, 1 eq.) in DMF (35 ml) was added $K_3PO_4$ (0.442 g, 1.56 mmol, 2 eq.), 3-mercapto-propionic acid methyl ester (4 ml, 36.23 mmol, 5 eq.) and L-proline (0.166 g, 1.44 mmol, 0.2 eq). The resulting reaction mixture was degassed with argon for a period of 10 min and CuI (0.137 g, 0.72 mmol, 0.1 eq.) was added and degassed again. The reaction mixture was then heated at 100° C. for 2 h. At completion, the reaction mixture was allowed to come RT and filtered over Celite®, filtrate was diluted with ethyl acetate (300 ml), the organic layer was washed with water (2×100 ml) and then by brine (100 ml). The organic layer was dried over anhydrous $Na_2SO_4$, filtered and concentrated under reduced pressure to yield crude residue which was purified by column chromatography to afford methyl 3-((2-(3-fluoro-4-methoxyphenyl)-4-methyl-7H-pyrrolo[2,3-d]pyrimidin-5-yl)thio)propanoate (0.12 g, 4%) as off white solid.

49b): methyl 3-((7-(3-(2-(dimethylamino)-2-oxoethoxy)phenyl)-2-(3-fluoro-4-methoxyphenyl)-4-methyl-7H-pyrrolo[2,3-d]pyrimidin-5-yl)thio)propanoate To a stirring solution of methyl 3-((2-(3-fluoro-4-methoxyphenyl)-4-methyl-7H-pyrrolo[2,3-d]pyrimidin-5-yl)thio)propanoate (0.1 g, 0.266 mmol, 1 eq.) in dimethyl sulfoxide (1 ml) was added $K_3PO_4$ (0.113 g, 0.533 mmol, 2 eq.), 2-(3-iodo-phenoxy)-N,N-dimethyl-acetamide (0.121 g, 0.399 mmol, 1.5 eq.) and trans-N,N'-dimethylcyclohexane-1,2-diamine (0.03 ml, 0.186 mmol, 0.7 eq). The resulting reaction mixture was degassed with argon for a period of 10 min and CuI (0.02 g, 0.106 mmol, 0.4 eq.) was added and degassed again. The reaction mixture was then heated at 60° C. for 30 min. At completion, the reaction mixture was allowed to come to RT and filtered over Celite®. The filtrate was diluted with ethyl acetate (50 ml), the organic layer was washed with water (2×10 ml) and then by brine (10 ml). The organic layer was dried over anhydrous $Na_2SO_4$, filtered and concentrated under reduced pressure to give crude product which was purified by column chromatography to afford methyl 3-((7-(3-(2-(dimethylamino)-2-oxoethoxy)phenyl)-

2-(3-fluoro-4-methoxyphenyl)-4-methyl-7H-pyrrolo[2,3-d]pyrimidin-5-yl)thio)propanoate (0.08 g, 54.4%).

49c): 2-(3-(2-(3-fluoro-4-methoxyphenyl)-4-methyl-5-(methylthio)-7H-pyrrolo[2,3-d]pyrimidin-7-yl)phenoxy)-N,N-dimethylacetamide To a stirring solution of methyl 3-((7-(3-(2-(dimethylamino)-2-oxoethoxy)phenyl)-2-(3-fluoro-4-methoxyphenyl)-4-methyl-7H-pyrrolo[2,3-d]pyrimidin-5-yl)thio)propanoate (0.2 g, 0.362 mmol) in dry THF under inert atmosphere was added t-BuOK (0.9 ml, 0.905 mmol, 1M in THF, 2.5 eq) drop wise at −78° C. and the mixture was stirred for 10 min at −78° C. The reaction mixture was quenched by addition of 1N HCl (4 ml) and allowed to come to RT. To this reaction mixture $K_2CO_3$ (0.4 g, 2.89 mmol, 8 eq) was added and after 10 min MeI (0.2 ml, 3.26 mmol, 9 eq) was added drop wise and the mixture was stirred for 15 min at 0° C. The reaction mixture was diluted with water (50 ml) and extracted with ethyl acetate (3×50 ml). Combined organic layer is washed with brine (50 ml), dried over anhydrous $Na_2SO_4$ and evaporated under reduced pressure to give crude product which was purified by column chromatography to afford 2-(3-(2-(3-fluoro-4-methoxyphenyl)-4-methyl-5-(methylthio)-7H-pyrrolo[2,3-d]pyrimidin-7-yl)phenoxy)-N,N-dimethylacetamide (0.1 g, 58%) as off white solid.

$^1$H-NMR (600 MHz; DMSO-$d_6$, δ ppm): 2.53 (s, 3H), 2.85 (s, 3H), 2.96 (s, 3H), 3.01 (s, 3H), 3.91 (s, 3H), 4.93 (s, 2H), 6.97-6.99 (1H), 7.27-7.31 (1H), 7.50-7.56 (3H), 7.92 (s, 1H), 8.11-8.15 (1H), 8.22-8.24 (1H).

Synthesis Example No. 50 preparation of: 2-((4-(4-ethyl-2-(3-fluoro-4-methoxyphenyl)-5H-pyrrolo[2,3-d]pyrimidin-7(6H)-yl)pyridin-2-yl)oxy)-N,N-dimethylacetamide (compound N. 73)

This compound can be synthesized in analogy to synthesis example No. 4.

$^1$H-NMR (600 MHz; DMSO-$d_6$, δ ppm): 1.25-1.28 (3H), 2.65-2.66 (2H), 2.86 (s, 3H), 3.07 (s, 3H), 3.13-3.15 (2H), 3.92 (3H), 4.06-4.07 (2H), 4.75 (s, 2H), 6.38-6.39 (1H), 7.28-7.30 (1H), 7.46-7.48 (1H), 7.55-7.56 (1H), 8.02-8.05 (1H), 8.14-8.16 (1H).

Synthesis Example No. 51 preparation of: 2-((4-(2-(5-chlorothiophen-2-yl)-4-ethyl-5H-pyrrolo[2,3-d]pyrimidin-7(6H)-yl)pyridin-2-yl)oxy)-N,N-dimethylacetamide (compound No. 74)

This compound can be synthesized in analogy to synthesis example No. 4.

$^1$H-NMR (600 MHz; DMSO-$d_6$, δ ppm): 1.21-1.24 (3H), 2.61-2.62 (2H), 2.86 (3H), 3.06 (3H), 3.13-3.15 (2H), 4.05-4.08 (2H), 4.75 (s, 2H), 6.33-6.34 (1H), 7.20-7.21 (1H), 7.42-7.44 (1H), 7.53-7.54 (1H), 7.70-7.71 (1H).

Synthesis Example No. 52 preparation of: 2-((4-(4-ethyl-2-(3-fluoro-4-methoxyphenyl)-7H-pyrrolo[2,3-d]pyrimidin-7-yl)pyridin-2-yl)oxy)-N,N-dimethylacetamide (compound No. 75)

This compound can be synthesized in analogy to synthesis example No. 5.

$^1$H-NMR (600 MHz; DMSO-$d_6$, δ ppm): 1.39-1.42 (3H), 2.88 (s, 3H), 3.08-3.13 (5H), 3.93 (s, 3H), 4.86 (s, 2H), 7.02-7.03 (1H), 7.24-7.26 (2H), 7.33-7.35 (1H), 7.78-7.79 (1H), 8.09-8.10 (1H), 8.16-8.18 (1H), 8.27.8.28 (1H).

Synthesis Example No. 53 preparation of: 2-(3-(4-cyclopropyl-2-(3-fluoro-4-methoxyphenyl)-7H-pyrrolo[2,3-d]pyrimidin-7-yl)phenoxy)-N,N-dimethylacetamide (compound No. 76)

This compound can be synthesized in analogy to synthesis example No. 5.

$^1$H-NMR (600 MHz; DMSO-$d_6$, δ ppm): 1.19-1.24 (2H), 1.34-1.37 (2H), 2.58-2.63 (1H), 2.85 (s, 3H), 3.02 (s, 3H), 3.91 (s, 3H), 4.94 (s, 2H), 6.98-7.00 (1H), 7.05-7.08 (1H), 7.26-7.28 (1H), 7.49-7.52 (1H), 7.57-7.58 (2H), 7.94-7.95 (1H), 8.08-8.11 (1H), 8.18-8.19 (1H).

Synthesis Example No. 59 preparation of: 2-(3-(4-ethyl-2-(6-methoxypyridin-3-yl)-7H-pyrrolo[2,3-d]pyrimidin-7-yl)phenoxy)-N,N-dimethylacetamide (compound No. 77)

This compound can be synthesized in analogy to synthesis example No. 5.

$^1$H-NMR (600 MHz; DMSO-$d_6$, δ ppm): 1.40-1.43 (3H), 2.86 (s, 3H), 3.02 (s, 3H), 3.09-3.12 (2H), 3.93 (s, 3H), 4.94 (s, 2H), 6.95-6.98 (3H), 7.49-7.51 (1H), 7.57-7.59 (2H), 7.97 (s, 1H), 8.64-8.65 (1H), 9.21 (s, 1H).

Synthesis Example No. 60 preparation of: 2-(3-(2'-(3-fluoro-4-methoxyphenyl)spiro[cyclopropane-1,5'-pyrrolo[2,3-d]pyrimidin]-7'(6'H)-yl)phenoxy)-N,N-dimethylacetamide (compound No. 78)

60a): 5,5-dibromo-2-chloro-5H-pyrrolo[2,3-d]pyrimidin-6(7H)-one

To stirred solution of 2-chloro-7H-pyrrolo[2,3-d]pyrimidine (5 g, 32.79 mmol, 1 eq) in t-BuOH (150 ml) was added Py.HBr.Br$_2$ (62.74 g, 196.07 mmol, 6 eq) portion wise at RT. The reaction mixture was stirred at RT for 1 h. The reaction mixture was cooled to 0° C. quenched with ice water (150 ml) and extracted with EtOAc (3×50 ml). The combined organic layer was washed with water (4×50 ml) and brine (50 ml), separated, dried (Na$_2$SO$_4$) and concentrated. The residue was co-distilled with pet-ether (3×50 ml) to afford 5,5-dibromo-2-chloro-5H-pyrrolo[2,3-d]pyrimidin-6(7H)-one (10.50 g; 99%) as a brown solid.

60b): 2-chloro-5H-pyrrolo[2,3-d]pyrimidin-6(7H)-one

To a stirred solution of 5,5-dibromo-2-chloro-5H-pyrrolo[2,3-d]pyrimidin-6(7H)-one (10.5 g, 32.20 mmol, 1 eq) in AcOH (150 ml) was added Zn-dust (20.93 g, 322.08 mmol, 10 eq) portion wise at RT, the reaction mixture was stirred at RT for 2 h. The reaction mixture was diluted with MeOH (150 ml) filtered through Celite®, washed with MeOH (50 ml) and the filtrate was concentrated. The residue was purified by column chromatography to afforded 2-chloro-5H-pyrrolo[2,3-d]pyrimidin-6(7H)-one (2 g; 36%) as a brown solid.

60c): 2'-chlorospiro[cyclopropane-1,5'-pyrrolo[2,3-d]pyrimidin]-6'(7'H)-one

To a stirred solution of 2-chloro-5H-pyrrolo[2,3-d]pyrimidin-6(7H)-one (5 g, 29.41 mmol, 1 eq) in dry THF (100 ml) at −20° C. was added diisopropylamine (8.64 ml, 61.76 mmol, 2.1 eq) followed by n-BuLi (47 ml, 2.5M in hexane, 117.64 mmol, 4 eq). The reaction mixture was allowed to warm to 0° C. and then 1,2-dibromoethane (7.6 ml, 88.23 mmol, 3 eq) was added. The reaction mixture was stirred at RT for 18 h. After completion, the reaction mixture was cooled to 0° C., quenched with sat. $NH_4Cl$ solution (60 ml) and extracted with EtOAc (3×60 ml). The combined organic layer was washed with water (2×50 ml) and brine (50 ml), dried ($Na_2SO_4$) and concentrated. The residue was purified by column chromatography to afforded 2'-chlorospiro[cyclopropane-1,5-pyrrolo[2,3-d]pyrimidin]-6(7'H)-one (1 g; 17%) as a yellow solid.

60d): 2'-(3-fluoro-4-hydroxyphenyl)spiro[cyclopropane-1,5'-pyrrolo[2,3-d]pyrimidin]-6'(7'H)-one The stirred solution of 2'-chlorospiro[cyclopropane-1,5'-pyrrolo[2,3-d]pyrimidin]-6'(7'H)-one (500 mg, 2.55 mmol, 1 eq), (3-fluoro-4-methoxyphenyl)boronic acid (650 mg, 3.82 mmol, 1.5 eq) and 1,4-dioxane (10 ml) in sealed tube was purged with argon for 15 min and added 2M aqueous $Cs_2CO_3$ (5.09 ml, 10.20 mmol, 4 eq). The reaction mixture was purged with argon for 15 min after which Pd(PPh$_3$)$_4$ (294 mg, 0.255 mmol, 0.1 eq) was added and the reaction mixture was again purged with argon for 15 min. The resulting suspension was heated at 100° C. for 18 h. The reaction mixture was cooled to RT, diluted with EtOAc (50 ml) and passed through Celite®. The filtrate was washed with water (2×50 ml), brine (50 ml), dried ($Na_2SO_4$), filtered and concentrated. The residue was purified by column chromatography to afforded 2'-(3-fluoro-4-hydroxyphenyl)spiro[cyclopropane-1,5'-pyrrolo[2,3-d]pyrimidin]-6'(7'H)-one (200 mg; 28%), as a brown solid.

60e): 2'-(3-fluoro-4-methoxyphenyl)-6',7'-dihydrospiro[cyclopropane-1,5'-pyrrolo[2,3-d]pyrimidine]

To a cold solution of LiAlH$_4$ (212 mg, 5.59 mmol, 3.2 eq) in THF (10 ml) was added a solution of 2'-(3-fluoro-4-hydroxyphenyl)spiro[cyclopropane-1,5'-pyrrolo[2,3-d]pyrimidin]-6'(7'H)-one (500 mg, 1.74 mmol, 1 eq) in THF (10 ml) drop wise at 0° C. The reaction mixture was stirred at RT for 4 h. The reaction mixture was cooled to 0° C. and quenched with ice water (5 ml), 2N NaOH solution (5 ml) and ice water (10 ml). The resulting mixture was filtered through Celite®, washed with EtOAc (60 ml). The filtrate was washed with water (2×20 ml) and brine solution (20 ml), dried ($Na_2SO_4$), filtered and concentrated. The residue was triturated with diethyl ether (20 ml) and filtered washed with diethyl ether (10 ml) dried under vacuum, to afford 2'-(3-fluoro-4-methoxyphenyl)-6',7'-dihydrospiro[cyclopropane-1,5'-pyrrolo[2,3-d]pyrimidine] (300 mg; 63%) as a brown solid.

60f): 2-(3-(2'-(3-fluoro-4-methoxyphenyl)spiro[cyclopropane-1,5'-pyrrolo[2,3-d]pyrimidin]-7'(6'H)-yl)phenoxy)-N,N-dimethylacetamide A solution of 2'-(3-fluoro-4-methoxyphenyl)-6',7'-dihydrospiro[cyclopropane-1,5'-pyrrolo[2,3-d]pyrimidine] (350 mg, 1.28 mmol, 1 eq) 2-(3-iodophenoxy)-N,N-dimethylacetamide (590 mg, 1.93 mmol, 1.5 eq) in 1,4-dioxane (25 ml) in sealed tube was purged with argon for 15 min and added CsF (586 mg, 3.86 mmol, 3 eq). The reaction mixture was purged with argon for 15 min after which CuI (122 mg, 0.643 mmol, 0.5 eq) was added to it and the reaction mixture was purged with argon for 15 min and added trans 1,2-diaminocyclohexyane (0.079 ml, 0.643 mmol, 0.5 eq). The reaction mixture was again purged with argon for 15 min. The resulting suspension was heated at 110° C. for 18 h. After completion, the reaction mixture was cooled to RT, diluted with EtOAc (100 ml) and passed through Celite®. The filtrate was washed with water (50 ml), brine (50 ml), dried ($Na_2SO_4$), filtered and concentrated. The residue was purified by column chromatography to afford 2-(3-(2'-(3-fluoro-4-methoxyphenyl)spiro[cyclopropane-1,5'-pyrrolo[2,3-d]pyrimidin]-7'(6'H)-yl)phenoxy)-N,N-dimethylacetamide (68 mg; 12%) as a pale yellow solid.

$^1$H-NMR (600 MHz; DMSO-d$_6$, δ ppm): 1.20-1.25 (4H), 2.84 (s, 3H), 3.01 (s, 3H), 3.91 (s, 3H), 4.15 (s, 2H), 4.85 (s, 2H), 6.68-6.69 (1H), 7.27-7.30 (1H), 7.34-7.37 (1H), 7.49-7.51 (1H), 7.62 (1H), 7.94 (s, 1H), 8.03-8.05 (1H), 8.14-8.16 (1H).

Synthesis Example No. 61 preparation of: 2-(3-(2'-(3-fluoro-4-methoxyphenyl)-4'-methylspiro-[cyclopropane-1,5'-pyrrolo[2,3-d]pyrimidin]-7'(6'H)-yl)phenoxy)-N,N-dimethylacetamide (compound No. 79)

61a): 2-(2-(3-fluoro-4-methoxyphenyl)-4-hydroxy-6-methylpyrimidin-5-yl)acetic acid Diethyl-2-acetylsuccinate (17.9 mL, 89.28 mmol) and 3-fluoro-4-methoxybenzimidamide (15 g, 89.28 mmol) were added successively to a suspension of freshly prepared sodium ethoxide (prepared by adding sodium in pieces to ethanol and concentration) in 1,4-dioxane (500 mL) and the mixture was heated at 145-150° C. for 20 h. The solvent was evaporated in vacuo, the residue was dissolved in ice water and acidified with 2N HCl till pH 2 was reached. The precipitated solid was filtered and washed with water followed by pet ether. The cake was co distilled with toluene and dried under reduced pressure to afford 2-(2-(3-fluoro-4-methoxyphenyl)-4-hydroxy-6-methylpyrimidin-5-yl)acetic acid (12 g) as pale pink solid which was used for the next step without further purification.

61b): methyl 2-(2-(3-fluoro-4-methoxyphenyl)-4-hydroxy-6-methylpyrimidin-5-yl)acetate Sulfuric acid (5 mL) was added to a suspension of 2-(2-(3-fluoro-4-methoxyphenyl)-4-hydroxy-6-methylpyrimidin-5-yl)acetic acid (12.8 g, 43.83 mmol) in methanol (100 mL) and heated at 70° C. for 2 h The solvent was evaporated in vacuo and the resulting residue was partitioned between water (100 mL) and dichloromethane (500 mL). The organic layer was separated and the aqueous layer was extracted with dichloromethane (3×500 mL). The combined organic layer was washed with brine (1×500 mL), dried over anhydrous sodium sulfate and concentrated in vacuo to afford crude product which was triturated with diethyl ether followed by pet ether and dried under reduced pressure to afford methyl 2-(2-(3-fluoro-4-methoxyphenyl)-4-hydroxy-6-methylpyrimidin-5-yl)acetate (9.82 g, 73%) as pale pink solid.

61c): methyl 2-(4-chloro-2-(3-fluoro-4-methoxyphenyl)-6-methylpyrimidin-5-yl)acetate N-Ethyldiisopropylamine (11.3 mL, 63.94 mmol) was added drop wise to a suspension of methyl 2-(2-(3-fluoro-4-methoxyphenyl)-4-hydroxy-6-methylpyrimidin-5-yl)acetate (9.8 g, 32.03 mmol) in phosphorus oxy chloride (12 mL) and heated at 100° C. for 20 h. The reaction mixture was cooled to 0° C. and poured into ice, stirred for 10 min and extracted with ethyl acetate (4×500 mL). The combined organic layers were washed successively with water (2×200 mL), brine (1×200 mL), dried over anhydrous sodium sulfate and concentrated in vacuo to afford crude product. Purification by column chromatography over silica gel afforded methyl 2-(4-chloro-2-(3-fluoro-4-methoxyphenyl)-6-methylpyrimidin-5-yl)acetate (7 g, 72%) as off white solid.

61d): 2-(3-fluoro-4-methoxyphenyl)-4-methyl-5H-pyrrolo[2,3-d]pyrimidin-6(7H)-one Ammonia gas was bubbled through a solution of methyl 2-(4-chloro-2-(3-fluoro-4-methoxyphenyl)-6-methylpyrimidin-5-yl)acetate (3.5 g, 10.80 mmol) in tetrahydrofuran (80 mL) and heated at 100° C. in a steel bomb for 20. The solvent was evaporated in vacuo to afford crude product. Purification by column chromatography over silica gel afforded 2-(3-fluoro-4-methoxyphenyl)-4-methyl-5H-pyrrolo[2,3-d]pyrimidin-6(7H)-one (1 g, 34%) as pale pink solid.

61e): 7-(3-(benzyloxy)phenyl)-2-(3-fluoro-4-methoxyphenyl)-4-methyl-5H-pyrrolo[2,3-d]pyrimidin-6(7H)-one A mixture of 2-(3-fluoro-4-methoxyphenyl)-4-methyl-5H-pyrrolo[2,3-d]pyrimidin-6(7H)-one (2 g, 7.33 mmol), 1-(benzyloxy)-3-iodobenzene (3.41 g, 10.99 mmol) and CsF (3.34 g, 21.99 mmol) in 1,4-dioxane (60 mL) in a sealed tube was purged with argon gas for 10 min. CuI (730 mg, 3.66 mmol) was added and the mixture was purged with argon gas for another 10 min. Then 1,2-diaminocyclohexane (417 mg, 3.66 mmol) was added to the reaction mixture and purging continued for another 10 min. The reaction mixture was stirred at 110° C. in a sealed tube for 20 h. The reaction mixture was filtered through Celite®, washed with dichloromethane and concentrated under reduced pressure to afford crude compound which was purified by column chromatography over silica gel to afford 7-(3-(benzyloxy)phenyl)-2-(3-fluoro-4-methoxyphenyl)-4-methyl-5H-pyrrolo[2,3-d]pyrimidin-6(7H)-one (2.5 g, 74%) as pale brown solid.

61f): 7'-(3-(benzyloxy)phenyl)-2'-(3-fluoro-4-methoxyphenyl)-4'-methylspiro[cyclopropane-1,5'-pyrrolo[2,3-d]pyrimidin]-6'(7'H)-one 1,2 Dibromo ethane (1.42 mL, 16.47 mmol) was added to a mixture of 7-(3-(benzyloxy)phenyl)-2-(3-fluoro-4-methoxyphenyl)-4-methyl-5H-pyrrolo[2,3-d]pyrimidin-6(7H)-one (2.5 g, 5.49 mmol) and potassium carbonate (7.59 g, 54.90 mmol) in dry DMF (40 mL) at 50° C. and stirred at 80° C. for 2 h The reaction mixture was cooled to RT, ice water was added and the reaction mixture was extracted with ethyl acetate (3×50 mL). The combined organic layer was washed successively with ice water (2×50 mL), brine (1×50 mL), dried over anhydrous sodium sulfate and concentrated in vacuo to afford crude compound which on purification by flash column chromatography over silica gel afforded 7'-(3-(benzyloxy)phenyl)-2'-(3-fluoro-4-methoxyphenyl)-4'-methylspiro[cyclopropane-1,5'-pyrrolo[2,3-d]pyrimidin]-6'(7'H)-one (1.8 g, 68%) as pale brown solid.

61g): 7'-(3-(benzyloxy)phenyl)-2'-(3-fluoro-4-methoxyphenyl)-4'-methyl-6',7'-dihydrospiro[cyclopropane-1,5'-pyrrolo[2,3-d]pyrimidine]

Borane dimethylsulfide complex (10.2M; 5.5 mL, 56.13 mmol) was added to a solution of 7'-(3-(benzyloxy)phenyl)-2'-(3-fluoro-4-methoxyphenyl)-4'-methylspiro[cyclopropane-1,5'-pyrrolo[2,3-d]pyrimidin]-6'(7'H)-one (1.8 g, 3.74 mmol) in THF (25 mL) and toluene (100 mL) and heated at 100° C. for 2 h. The reaction mixture was cooled to 0° C., quenched with methanol (125 mL) and refluxed for 1.5 h. The volatiles were evaporated in vacuo and the resulting crude was purified by column chromatography over silica gel to afford 7'-(3-(benzyloxy)phenyl)-2'-(3-fluoro-4-methoxyphenyl)-4'-methyl-6',7'-dihydrospiro[cyclopropane-1,5'-pyrrolo[2,3-d]pyrimidine] (1 g, 57%) as off white solid.

61h): 3-(2'-(3-fluoro-4-methoxyphenyl)-4'-methylspiro[cyclopropane-1,5'-pyrrolo[2,3-d]pyrimidin]-7'(6'H)-yl)phenol 10% Pd—C (300 mg) was added to a solution of 7'-(3-(benzyloxy)phenyl)-2'-(3-fluoro-4-methoxyphenyl)-4'-methyl-6',7'-dihydrospiro[cyclopropane-1,5'-pyrrolo[2,3-d]pyrimidine] (600 mg, 1.28 mmol) in methanol (30 mL) and THF (50 mL) and the mixture was hydrogenated in Parr apparatus under 45 psi pressure at RT for 20 h. The catalyst was filtered over Celite®, washed with methanol and the combined filtrate and washings were evaporated in vacuo to afford 3-(2'-(3-fluoro-4-methoxyphenyl)-4'-methylspiro[cyclopropane-1,5'-pyrrolo[2,3-d]pyrimidin]-7'(6'H)-yl)phenol (450 mg, 93%) as off white solid.

61i): 2-(3-(2'-(3-fluoro-4-methoxyphenyl)-4'-methylspiro[cyclopropane-1,5'-pyrrolo[2,3-d]pyrimidin]-7'(6'H)-yl)phenoxy)-N,N-dimethylacetamide 2-Chloro-N,N-dimethylacetamide (0.14 mL, 1.31 mmol) was added drop wise to a stirred solution of 3-(2'-(3-fluoro-4-methoxyphenyl)-4'-methylspiro[cyclopropane-1,5'-pyrrolo[2,3-d]pyrimidin]-7'(6'H)-yl)phenol (450 mg, 1.19 mmol) and potassium carbonate (330 mg, 2.38 mmol) in acetonitrile (40 mL) and the mixture was refluxed for 16 h. The volatiles were evaporated in vacuo and the resulting residue was partitioned between water (30 mL) and ethyl acetate (25 mL). The organic layer was separated and the aqueous layer was extracted with ethyl acetate. The combined organic layers were washed with brine, dried over anhydrous $Na_2SO_4$ and concentrated under reduced pressure to afford crude compound which was purified by column chromatography over silica gel to afford 2-(3-(2'-(3-fluoro-4-methoxyphenyl)-4'-methylspiro[cyclopropane-1,5'-pyrrolo[2,3-d]pyrimidin]-7'(6'H)-yl)phenoxy)-N,N-dimethylacetamide (220 mg, 40%) as off white solid.

$^1$H-NMR (600 MHz; DMSO-$d_6$, δ ppm): 1.07-1.09 (2H), 1.52-1.54 (2H), 2.19 (s, 3H), 2.84 (s, 3H), 3.01 (s, 3H), 3.91 (s, 3H), 4.04 (s, 2H), 4.83 (s, 2H), 6.66-6.67 (1H), 7.26-7.28 (1H), 7.33-7.35 (1H), 7.45-7.47 (1H), 7.59 (s, 1H), 8.02-8.04 (1H), 8.13-8.14 (1H).

Synthesis Example No. 62 preparation of: 2-(3-(4-ethyl-2-(2-methoxypyridin-3-yl)-7H-pyrrolo[2,3-d]pyrimidin-7-yl)phenoxy)-N,N-dimethylacetamide (compound No. 80)

This compound can be synthesized in analogy to synthesis example No. 5.

$^1$H-NMR (600 MHz; DMSO-$d_6$, δ ppm): 1.37-1.39 (3H), 2.83 (s, 3H), 2.99 (s, 3H), 3.09-3.11 (2H), 3.96 (s, 3H), 4.89 (s, 2H), 6.92-6.93 (1H), 6.98.6.99 (1H), 7.12-7.14 (1H), 7.44-7.46 (1H), 7.62-7.64 (1H), 7.72-7.74 (1H), 8.06 (1H), 8.22-8.24 (1H), 8.26-8.28 (1H).

Synthesis Example No. 63 preparation of: 2-(3-(4-ethyl-2-(3-(methylsulfonyl)phenyl)-7H-pyrrolo[2,3-d]pyrimidin-7-yl)phenoxy)-N,N-dimethylacetamide (compound No. 81)

This compound can be synthesized in analogy to synthesis example No. 5.

$^1$H-NMR (600 MHz; DMSO-$d_6$, δ ppm): 1.43-1.45 (3H), 2.83 (s, 3H), 3.00 (s, 3H), 3.15-3.18 (2H), 3.28 (s, 3H), 4.94 (s, 2H), 6.99-7.02 (2H), 7.49-7.58 (3H), 7.80-7.82 (1H), 8.03-8.04 (1H), 8.77-8.78 (1H), 8.97 (1H).

Synthesis Example No. 64 preparation of: 2-(3-(4-ethyl-2-(pyridin-4-yl)-7H-pyrrolo[2,3-d]pyrimidin-7-yl)phenoxy)-N,N-dimethylacetamide (compound No. 82)

This compound can be synthesized in analogy to synthesis example No. 5.

$^1$H-NMR (600 MHz; DMSO-$d_6$, δ ppm): 1.42-1.45 (3H), 2.85 (s, 3H), 3.02 (s, 3H), 3.14-3.18 (2H), 4.95 (s, 2H), 7.00-7.03 (2H), 7.51-7.58 (3H), 8.07 (1H), 8.33-8.34 (2H), 8.73.8.74 (2H).

Synthesis Example No. 65 preparation of: 2-(3-(4-ethyl-2-(pyridin-3-yl)-7H-pyrrolo[2,3-d]pyrimidin-7-yl)phenoxy)-N,N-dimethylacetamide (compound No. 83)

This compound can be synthesized in analogy to synthesis example No. 5.

$^1$H-NMR (600 MHz; DMSO-$d_6$, δ ppm): 1.42-1.45 (3H), 2.85 (s, 3H), 3.02 (s, 3H), 3.14-3.17 (2H), 4.95 (2H), 6.98-7.01 (2H), 7.50-7.59 (4H), 8.03 (1H), 8.66-8.67 (1H), 8.72-8.74 (1H), 9.59 (s, 1H).

The compounds Nos. 84 to 99 as given in below table 3 were synthesized according to following general procedures:

General Procedure (Method A)

The relevant 2-chloro-pyrimidine (1.0 mL of a 0.1 M solution of either tert-butyl 2-(4-(2-chloro-4-ethyl-5H-pyrrolo[2,3-d]pyrimidin-7(6H)-yl)phenyl)acetate or tert-butyl 4-(2-chloro-4-ethyl-5H-pyrrolo[2,3-d]pyrimidin-7(6H)-yl)benzoate in ethylene glycol) and boronic acid (1.5 mL of a 0.1 M solution in ethylene glycol) were placed together with sodium carbonate (0.305 mL of a 2.0 M solution in water) and tetrakis(triphenylphosphine)-palladium(0) (0.5 mL of a 0.0062 M solution in ethylene glycol) in a vial and the mixture was heated under an argon atmosphere for 1 h to 120° C. under microwave irradiation. The reaction mixture was diluted with water (2.5 mL) and dichloromethane (3 mL) and stirred for 30 minutes at room temperature. The aqueous phase was separated and extracted with dichloromethane (2×3 mL). The organic layers were combined, the solvent was evaprated in vacuo and the remaining product of the Suzuki coupling was treated with 0.5 mL trifluoroacetic acid for 10 min. Excess reagent was removed under reduced pressure and the remnant was purified by preparative HPLC.

General Procedure (Method B)

The general procedure A was followed using 2-(3-(2-chloro-4-ethyl-7H-pyrrolo[2,3-d]pyrimidin-7-yl)phenoxy)-N,N-dimethylacetamide instead of one of the above mentioned 2-chloro-pyrimidines. After removal of the dichloromethane, the product of the Suzuki coupling was directly purified by preparative HPLC.

TABLE 3

| Cpd. No. | Name | Method | Mass peak [M + H]$^+$ |
|---|---|---|---|
| 6 | 4-(4-Ethyl-2-(3-fluoro-4-methoxyphenyl)-5H-pyrrolo[2,3-d]pyrimidin-7(6H)-yl)benzoic acid | see above | 394.3 |
| 8 | 2-(4-Ethyl-2-(3-fluoro-4-methoxyphenyl)-5H-pyrrolo[2,3-d]pyrimidin-7(6H)-yl)phenyl)acetic acid | see above | 408.3 |
| 21 | 2-(4-(2-(3-Chloro-4-methoxyphenyl)-4-ethyl-5H-pyrrolo[2,3-d]pyrimidin-7(6H)-yl)phenyl)acetic acid | see above | 424.3 |
| 33 | 2-(4-(2-(3,4-Difluorophenyl)-4-ethyl-5H-pyrrolo[2,3-d]pyrimidin-7(6H)-yl)phenyl)acetic acid | see above | 396.3 |
| 80 | 2-(3-(4-Ethyl-2-(2-methoxypyridin-3-yl)-7H-pyrrolo[2,3-d]pyrimidin-7-yl)phenoxy)-N,N-dimethylacetamide | see above | 432.2 |
| 81 | 2-(3-(4-Ethyl-2-(3-(methylsulfonyl)phenyl)-7H-pyrrolo[2,3-d]pyrimidin-7-yl)phenoxy)-N,N-dimethylacetamide | see above | 479.2 |
| 82 | 2-(3-(4-Ethyl-2-(pyridin-4-yl)-7H-pyrrolo[2,3-d]pyrimidin-7-yl)phenoxy)-N,N-dimethylacetamide | see above | 402.2 |
| 83 | 2-(3-(4-Ethyl-2-(pyridin-3-yl)-7H-pyrrolo[2,3-d]pyrimidin-7-yl)phenoxy)-N,N-dimethylacetamide | see above | 402.2 |
| 84 | 4-(2-(Benzofuran-5-yl)-4-ethyl-5H-pyrrolo[2,3-d]pyrimidin-7(6H)-yl)benzoic acid | A | 386.3 |
| 85 | 2-(3-(4-Ethyl-2-(3-fluoro-4-methoxyphenyl)-7H-pyrrolo[2,3-d]pyrimidin-7-yl)phenoxy)-N,N-dimethylacetamide | B | 449.3 |
| 86 | 2-(4-(4-Ethyl-2-(4-fluoro-3-methoxyphenyl)-5H-pyrrolo[2,3-d]pyrimidin-7(6H)-yl)phenyl)acetic acid | A | 408.3 |

TABLE 3-continued

| Cpd. No. | Name | Method | Mass peak [M + H]+ |
|---|---|---|---|
| 87 | 2-(3-(2-(Benzo[d][1,3]dioxol-5-yl)-4-ethyl-7H-pyrrolo[2,3-d]pyrimidin-7-yl)phenoxy)-N,N-dimethylacetamide | B | 445.2 |
| 88 | 2-(3-(2-(Benzo[d]thiazol-6-yl)-4-ethyl-7H-pyrrolo[2,3-d]pyrimidin-7-yl)phenoxy)-N,N-dimethylacetamide | B | 458.2 |
| 89 | 2-(4-(2-(Benzofuran-5-yl)-4-ethyl-5H-pyrrolo[2,3-d]pyrimidin-7(6H)-yl)phenyl)acetic acid | A | 400.3 |
| 90 | 2-(4-(2-(4-(Difluoromethoxy)phenyl)-4-ethyl-5H-pyrrolo[2,3-d]pyrimidin-7(6H)-yl)phenyl)acetic acid | A | 426.3 |
| 91 | 2-(3-(4-Ethyl-2-(4-(methylsulfonyl)phenyl)-7H-pyrrolo[2,3-d]pyrimidin-7-yl)phenoxy)-N,N-dimethylacetamide | B | 479.2 |
| 92 | 2-(3-(2-(3-Chloro-4-methoxyphenyl)-4-ethyl-7H-pyrrolo[2,3-d]pyrimidin-7-yl)phenoxy)-N,N-dimethylacetamide | B | 465.2 |
| 93 | 2-(4-(2-(Benzo[d]thiazol-6-yl)-4-ethyl-5H-pyrrolo[2,3-d]pyrimidin-7(6H)-yl)phenyl)acetic acid | A | 417.3 |
| 94 | 2-(3-(4-Ethyl-2-(4-methoxyphenyl)-7H-pyrrolo[2,3-d]pyrimidin-7-yl)phenoxy)-N,N-dimethylacetamide | B | 431.3 |
| 95 | 2-(3-(2-(4-Ethoxyphenyl)-4-ethyl-7H-pyrrolo[2,3-d]pyrimidin-7-yl)phenoxy)-N,N-dimethylacetamide | B | 445.3 |
| 96 | 2-(4-(2-(4-Ethoxyphenyl)-4-ethyl-5H-pyrrolo[2,3-d]pyrimidin-7(6H)-yl)phenyl)acetic acid | A | 404.3 |
| 97 | 2-(3-(4-Ethyl-2-(pyrimidin-5-yl)-7H-pyrrolo[2,3-d]pyrimidin-7-yl)phenoxy)-N,N-dimethylacetamide | B | 403.2 |
| 98 | 4-(2-(3-Ethoxyphenyl)-4-ethyl-5H-pyrrolo[2,3-d]pyrimidin-7(6H)-yl)benzoic acid | A | 390.3 |
| 99 | 2-(4-(2-(3-Chloro-4-fluorophenyl)-4-ethyl-5H-pyrrolo[2,3-d]pyrimidin-7(6H)-yl)phenyl)acetic acid | A | 412.3 |

A: Determination of the PDE4B IC50 Values with a cAMP HRTF® Assay to Determine the Activity of hPDE4B1

The inhibiting effect of the compounds on the enzyme activity of human PDE4B1 is measured by the quantification of 5'-AMP, which is formed from 3',5'-adenosine monophosphate (cAMP). Human recombinant enzyme, expressed in Sf9 cells, and the HTRF (homogeneous time-resolved fluorescence) detection method are used in the assay.

The test compound or water (control) is mixed with the human recombinant PDE4B1 enzyme (4.8 U) in a buffer consisting of 44.4 mM tris-HCl, 5.28 mM MgCl2, 2.64 mM DTT and 0.044% Tween 20 (pH 7.8). After adding the cAMP enzyme substrate (final concentration 40 nM) the mixture is incubated for 30 minutes at room temperature. Then a fluorescence acceptor (Dye2 marked with cAMP), a fluorescence donor (anti-cAMP antibody marked with a europium cryptate) and the non-specific phosphodiesterase inhibitor IBMX (3-isobutyl-1-methylxanthine; final concentration 1 mM) are added. After 60 minutes the fluorescence transfer, which correlates with the amount of remaining cAMP, is measured with a microplate reader (Rubystar, BMG) at λex=337 nm, λem=620 nm and λem=665 nm. The enzyme activity is calculated from the quotient formed from the measured signal at 665 nm and that at 620 nm. The result is expressed as the percentage inhibition of enzyme activity of the control (without PDE4 inhibitor) (literature: N. Saldou et al., Comparison of recombinant human PDE4 isoforms: interaction with substrate and inhibitors, Cell. Signal. Vol. 10, No. 6, 427-440, 1998). The enzyme is omitted for measurement of the basal control. The averaged results are set out below:

In above test A the following compounds showed an IC50-value in the range from 1 to 10 μM (N=1-2, n=2). Compound Nos.: 6, 45, 47, 50, 51, 69, 76, 77, 78, 79, In above test A the following compounds showed an IC50-value<1 μM (N=1-2, n=2): Compound Nos.: 1, 2, 4, 7, 8, 9, 12, 14, 16, 20, 21, 24, 26, 38, 39, 40, 46, 80, 81, 82, 83

The compounds according to the invention were tested with above mentioned assay and the results are given in table 4 which shows the inhibition of PDE4B at a test substrate concentration of 3 μM in [%]:

TABLE 4

| Cpd. No. | Inhibition at 3 μM in % |
|---|---|
| 84 | 45 |
| 85 | 43 |
| 86 | 47 |
| 87 | 52 |
| 88 | 51 |
| 89 | 63 |
| 90 | 58 |
| 91 | 52 |
| 92 | 67 |
| 93 | 57 |
| 94 | 54 |
| 95 | 41 |
| 96 | 39 |
| 97 | 67 |
| 98 | 43 |
| 99 | 54 |

The invention claimed is:
1. A condensed pyrimidine compounds of general formula (I):

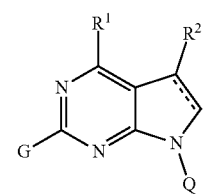

in which
G is a phenyl optionally substituted with at least one substituent Z or a 5- to 10-membered heteroaryl optionally substituted with at least one substituent Z;

Z independently of one another is ($(C_1-C_6)$-alkyl, $(C_1-C_6)$-hydroxyalkyl, $(C_1-C_6)$-alkoxy, $(C_1-C_6)$-haloalkyl, $(C_1-C_6)$-haloalkoxy, $S(C_1-C_6)$-alkyl, $SO(C_1-C_6)$-alkyl, $SO_2(C_1-C_6)$-alkyl, halogen, hydroxyl or cyano, wherein aforementioned alkyls are branched or straight-chain and can be substituted;

$R^1$ is $(C_1-C_4)$-alkyl, $(C_1-C_4)$-alkoxy, $(C_3-C_6)$-cycloalkyl, $S(O)_x(C_1-C_4)$-alkyl or $(C_1-C_4)$-alkyl-$S(O)_x(C_1-C_4)$ alkyl;

if the structural element ----- represents a double bond, then $R^2$ stands for hydrogen, $(C_1-C_4)$-alkyl, $S(O)_x(C_1-C_4)$-alkyl or $(C_1-C_4)$-alkyl-$S(O)_x(C_1-C_4)$alkyl;

if the structural element ----- represents a single bond, then $R^2$ stands for $R^{2a}$ and $R^{2b}$ which are independently of each other hydrogen, $(C_1-C_4)$-alkyl, $S(O)_x(C_1-C_4)$-alkyl or $(C_1-C_4)$-alkyl-$S(O)_x(C_1-C_4)$alkyl, under the proviso that only one of $R^{2a}$ and $R^{2b}$ is $S(O)-_x(C_1-C_4)$-alkyl or $(C_1-C_4)$-alkyl-$S(O)_x(C_1-C_4)$alkyl at the same time, or wherein $R^{2a}$ and $R^{2b}$ together with the carbon atom to which they are bound form a 3- to 6-membered saturated or unsaturated carbocycle or a 3- to 6-membered heterocycle containing at least one heteroatom selected from O, N and S wherein the sulphur atom may be oxidized to form a chemical grouping SO or $SO_2$;

x is 0, 1, or 2;

Q is phenyl substituted with a substituent $X^1$ and optionally with at least one substituent X;

$X^1$ is selected from the following chemical groupings $L-CO_2R^3$, $O-L-CO_2R^3$, $O-L-COR^4$, $NH-L-CO_2R^3$, and $N((C_1-C_4)\text{-alkyl})-L-CO_2R^3$;

$R^3$ is hydrogen or $(C_1-C_6)$-alkyl;

$R^4$ is $NH_2$, $NHR^5$, $NR^5R^6$, whereas $R^5$ and $R^6$ independently of one another is $(C_1-C_6)$-alkyl, $(C_1-C_6)$-hydroxyalkyl, $(C_3-C_6)$-cycloalkyl, $(C_1-C_4)$-alkyl-$(C_3-C_6)$-cycloalkyl, or a 3- to 6-membered heterocycle having at least one heteroatom selected from nitrogen, oxygen or sulphur, or $R^5$ and $R^6$, together with the nitrogen atom to which they are bound, form a saturated 3- to 6-membered heterocycle, which optionally contains at least one further heteroatom selected from nitrogen, oxygen or sulphur, and which heterocycle can be substituted with at least one substituent selected from branched or straight-chain $(C_1-C_6)$-alkyl or hydroxyl;

L is a bond, a branched or straight-chain $(C_1-C_4)$-alkyl or $(C_2-C_4)$-alkenyl group, which alkyl or alkenyl groups may be substituted with at least one substituent selected from $(C_1-C_6)$-alkyl, $(C_3-C_6)$-cycloalkyl, $(C_1-C_6)$-alkoxy, $(C_3-C_6)$-cycloalkoxy, $(C_1-C_6)$-haloalkyl, $(C_1-C_6)$-haloalkoxy, halogen, hydroxyl, amino or cyano; and X independently of one another is $(C_1-C_6)$-alkyl, $(C_3-C_6)$-cycloalkyl, $(C_1-C_6)$-alkoxy, $(C_3-C_6)$-cycloalkoxy, $(C_1-C_6)$-haloalkyl, $(C_1-C_6)$-haloalkoxy, halogen, hydroxyl, cyano, carboxyl, $-NH_2$, $-NH(C_1-C_6)$-alkyl, $-N((C_1-C_6)\text{-alkyl})_2$, N-pyrrolidinyl, N-piperidinyl, N-morpholinyl, $-NH-C(O)-(C_1-C_6)$-alkyl, $-C(O)-NH_2$, $-C(O)-NH(C_1-C_6)$-alkyl, $-C(O)-N((C_1-C_6)\text{-alkyl})_2$, $-S(O)_2-NH_2$, $-S(C_1-C_6)$-alkyl, $-S(O)-(C_1-C_6)$-alkyl, or $-S(O)_2-(C_1-C_6)$-alkyl, wherein the aforementioned alkyl chains are branched or straight-chain and can be substituted;

or a pharmacologically tolerable salt, diastereomer, enantiomer, racemate, hydrate or solvate thereof.

2. The condensed pyrimidine compound according to claim 1, wherein
G is selected from phenyl, thienyl, furanyl, thiazolyl, isothiazolyl, oxazolyl, isoxazolyl, pyridiyl, pyrimidinyl, benzofuranyl, benzodioxazolyl, benzothiazolyl, quinolinyl, benzodioxazolyl.

3. The condensed pyrimidine compounds according to claim 1, wherein
G is selected from the following groups G1 to G39

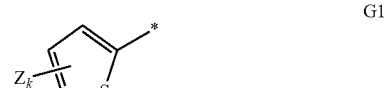
G1

G2

G3

G4

G5

G6

G7

G8

G9

G10

G11

G12

G13

-continued
| | |
|---|---|
| 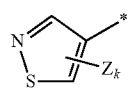 | G14 |
| 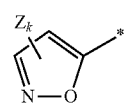 | G15 |
| 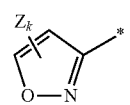 | G16 |
| 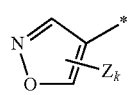 | G17 |
| 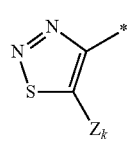 | G18 |
| 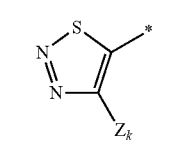 | G19 |
| 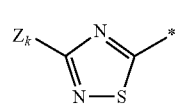 | G20 |
| 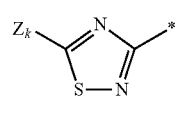 | G21 |
| 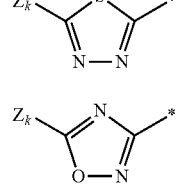 | G22 |
| 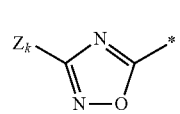 | G23 |
| 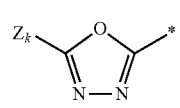 | G24 |
| 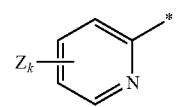 | G25 |
| 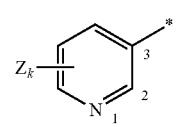 | G26 |
| 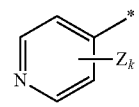 | G27 |
-continued
| | |
|---|---|
| 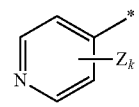 | G28 |
| 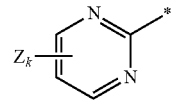 | G29 |
| 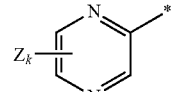 | G30 |
| 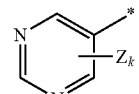 | G31 |
| 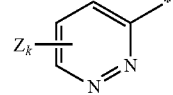 | G32 |
| 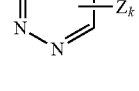 | G33 |
| 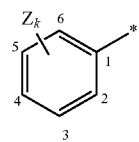 | G34 |
| 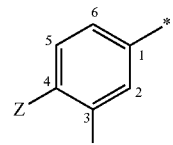 | G35 |
| 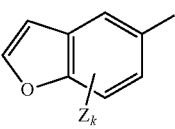 | G36 |
| 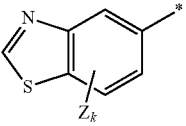 | G37 |
| | G38 or |

G39

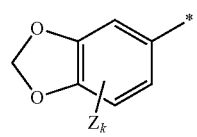

in which the site marked with an asterisk (*) indicates the binding site at position 2 of the pyrimidine ring; and k is 0, 1, 2, 3, 4, 5, 6.

4. The condensed pyrimidine compounds according to claim 3, wherein

G is selected from G1, G2, G3, G4, G5, G6, G7, G8, G9, G10, G11, G12, G13, G14, G15, G16, G17, G26, G27, G28, G34, G35, G36, G37 and G38;

Z independently of one another is $(C_1-C_4)$-alkoxy, Cl, F, Br, $(C_1-C_4)$-alkyl, $(C_1-C_4)$-haloalkyl, $(C_1-C_4)$-haloalkoxy, $S(C_1-C_4)$-alkyl, $SO(C_1-C_4)$-alkyl, $SO_2(C_1-C_4)$-alkyl;

Q is a phenyl substituted with a substituent $X^1$ and optionally with at least one substituent X.

5. The condensed pyrimidine compounds according to claim 1, wherein

Q is selected from the following groups Q1 to Q15, in which the site marked with an asterisk indicates the binding site at the nitrogen atom:

Q1

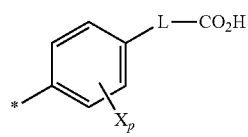

Q2

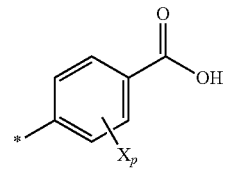

Q3

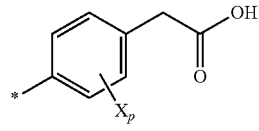

Q4

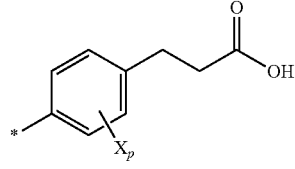

Q5

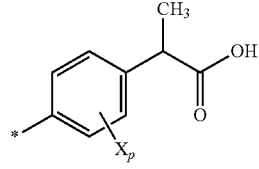

Q6

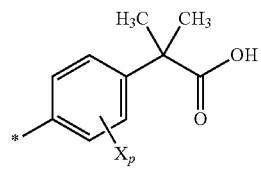

Q7

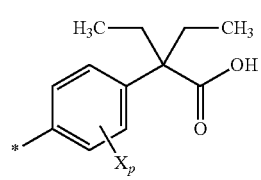

Q8

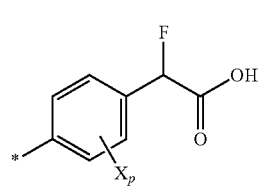

Q9

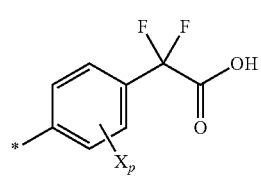

Q10

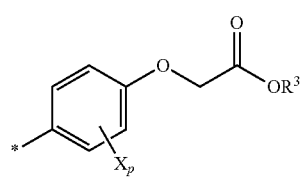

Q11

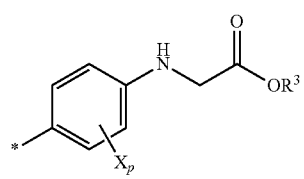

Q12

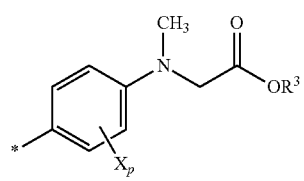

Q13

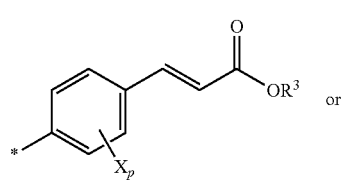

or

-continued

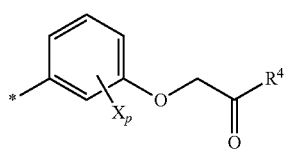
Q14 p is 0, 1, 2, 3 or 4;
$R^3$ is hydrogen or methyl or ethyl;
$R^4$ is $NH_2$, $NHCH_3$, $N(CH_3)_2$, $NHC_2H_5$, $NHCH(CH_3)_2$, $NHCH_2CH_2OH$ or one of the following groups $R^4$-1 to $R^4$-9

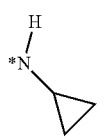
$R^4$-1

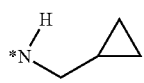
$R^4$-2

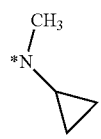
$R^4$-3

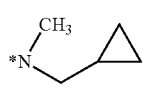
$R^4$-4

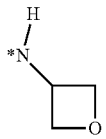
$R^4$-5

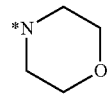
$R^4$-6

$R^4$-7

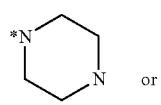
$R^4$-8 or

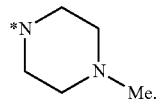
$R^4$-9

6. The pyrimidine compounds according to claim 1 having the following general formula (I-A):

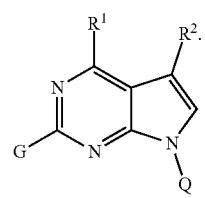
(I-A)

7. The pyrimidine compounds according to claim 1 having the following general formula (I-B)

(I-B)

8. The pyrimidine compounds according to claim 7 having one of the following general formulae
(I-B-1), (I-B-2) or (I-B-3):

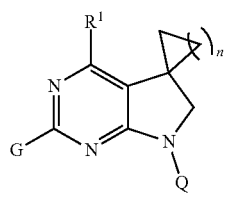
(I-B-1)

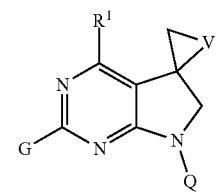
(I-B-2)

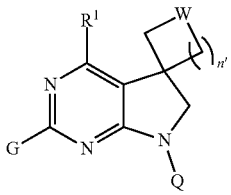
(I-B-3)

wherein
n stands for 1, 2, 3, or 4;
n' stands for 1, 2, or 3;
V stands for N or S(O)x';
W stands for O, N, or S(O)x'; and
x' is 0, 1, or 2.

9. A pharmaceutical composition comprising at least one compound according to claim 1.

10. A method for treating a disease or condition in a patient in need of such treating, wherein the disease or condition is selected from the following: psoriatic arthritis, psoriasis, acute and chronic inflammations of the gall bladder and bile ducts, pseudopolyps, juvenile polyps, COPD, asthma, cancers mediated by phosphodiesterase 4B, B-cell lymphoma, T-cell lymphoma, schizophrenia, depression, bipolar or manic depression, or generalised anxiety disorder, said method comprising administering to said patient an effective amount to treat said disease or condition of at least one compound according to claim 1.

* * * * *